(12) United States Patent
Yamniuk et al.

(10) Patent No.: US 10,787,498 B2
(45) Date of Patent: Sep. 29, 2020

(54) FIBRONECTIN TYPE III DOMAIN PROTEINS WITH ENHANCED SOLUBILITY

(71) Applicant: BRISTOL-MYERS SQUIBB COMPANY, Princeton, NJ (US)

(72) Inventors: Aaron P Yamniuk, Lawrenceville, NJ (US); Stanley R Krystek, Ringoes, NJ (US)

(73) Assignee: BRISTOL-MYERS SQUIBB COMPANY, Princeton, NJ (US)

(*) Notice: Subject to any disclaimer, the term of this patent is extended or adjusted under 35 U.S.C. 154(b) by 67 days.

(21) Appl. No.: 14/766,036

(22) PCT Filed: Feb. 5, 2014

(86) PCT No.: PCT/US2014/014887
§ 371 (c)(1),
(2) Date: Aug. 5, 2015

(87) PCT Pub. No.: WO2014/124017
PCT Pub. Date: Aug. 14, 2014

(65) Prior Publication Data
US 2015/0368319 A1 Dec. 24, 2015

Related U.S. Application Data

(60) Provisional application No. 61/761,452, filed on Feb. 6, 2013.

(51) Int. Cl.
*C07K 14/435* (2006.01)
*C07K 14/78* (2006.01)

(52) U.S. Cl.
CPC .................................. *C07K 14/78* (2013.01)

(58) Field of Classification Search
None
See application file for complete search history.

(56) References Cited

U.S. PATENT DOCUMENTS

| | | | |
|---|---|---|---|
| 6,818,418 B1 | 11/2004 | Lipovsek et al. | |
| 7,115,396 B2 | 10/2006 | Lipovsek et al. | |
| 7,556,925 B2 | 7/2009 | Koide et al. | |
| 7,598,352 B2 | 10/2009 | Koide | |
| 7,847,062 B2 | 12/2010 | Chen et al. | |
| 7,858,739 B2 | 12/2010 | Chen et al. | |
| 8,067,201 B2 | 11/2011 | Morin et al. | |
| 8,221,765 B2 | 7/2012 | Camphausen et al. | |
| 8,258,265 B2 | 9/2012 | Koide | |
| 8,263,741 B2 | 9/2012 | Koide | |
| 8,278,419 B2 | 10/2012 | Jacobs et al. | |
| 8,293,482 B2 | 10/2012 | Jacobs et al. | |
| 8,324,362 B2 | 12/2012 | Chen et al. | |
| 9,416,170 B2 | 8/2016 | Davis et al. | |
| 2002/0019517 A1 | 2/2002 | Koide | |
| 2003/0170753 A1 | 9/2003 | Koide | |
| 2003/0186385 A1 | 10/2003 | Koide | |
| 2005/0038229 A1 | 2/2005 | Lipovsek et al. | |
| 2005/0255548 A1 | 11/2005 | Lipovsek et al. | |
| 2006/0210604 A1 | 9/2006 | Dadey et al. | |
| 2006/0246059 A1 | 11/2006 | Lipovsek et al. | |
| 2006/0270604 A1 | 11/2006 | Lipovsek et al. | |
| 2007/0082365 A1 | 4/2007 | Lipovsek et al. | |
| 2008/0015339 A1 | 1/2008 | Lipovsek et al. | |
| 2008/0063651 A1 | 3/2008 | Lipovsek et al. | |
| 2008/0108798 A1 | 5/2008 | Lipovsek et al. | |
| 2008/0139791 A1 | 6/2008 | Lipovsek et al. | |
| 2008/0220049 A1 | 9/2008 | Chen et al. | |
| 2009/0176654 A1 | 7/2009 | Cappuccilli et al. | |
| 2010/0081792 A1 | 4/2010 | Grant et al. | |
| 2010/0144601 A1 | 6/2010 | Jacobs et al. | |
| 2010/0152063 A1 | 6/2010 | Cappuccilli et al. | |
| 2010/0273216 A1 | 10/2010 | Morin et al. | |
| 2010/0298541 A1 | 11/2010 | Wu et al. | |
| 2010/0322930 A1 | 12/2010 | Kolbinger et al. | |
| 2011/0021746 A1 | 1/2011 | Cappuccilli et al. | |
| 2011/0038866 A1 | 2/2011 | Hastewell et al. | |
| 2011/0123545 A1 | 5/2011 | Marsh et al. | |
| 2011/0124527 A1 | 5/2011 | Cappuccilli et al. | |

(Continued)

FOREIGN PATENT DOCUMENTS

| EP | 1137941 | 10/2001 |
|---|---|---|
| EP | 1266025 | 12/2002 |

(Continued)

OTHER PUBLICATIONS

Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Bork et al. Go hunting in sequence databases but watch out for the traps. Trends in Genetics. 12(10): 425-427, 1996.*
Bork, A. Powers and pitfalls in sequence analysis: the 70% hurdle. Genome Res 10: 398-400, 2000.*
Skolnick et al. From genes to protein structure and function: novel applications of computational approaches in the genomic era. Trends in Biotech 18(1): 34-39, 2000.*

(Continued)

*Primary Examiner* — Julie Ha
*Assistant Examiner* — Kristina M Hellman
(74) *Attorney, Agent, or Firm* — Nelson Mullins Riley & Scarborough LLP; Jane E. Remillard, Esq.; Christopher L. Frank

(57) ABSTRACT

Provided herein are polypeptides comprising a modified fibronectin type III (Fn3) domain, wherein the amino acid corresponding to residue 58 of SEQ ID NO: 1 is mutated, and wherein the solubility is enhanced relative to the solubility of a Fn3 domain in which the amino acid corresponding to residue 58 of SEQ ID NO: 1 is not mutated. Also provided are libraries comprising a plurality of the polypeptides and a method for identifying a polypeptide that binds to a target.

3 Claims, 23 Drawing Sheets
(9 of 23 Drawing Sheet(s) Filed in Color)
Specification includes a Sequence Listing.

(56) References Cited

U.S. PATENT DOCUMENTS

| | | |
|---|---|---|
| 2011/0274623 A1 | 11/2011 | Jacobs |
| 2011/0275535 A1 | 11/2011 | Loew |
| 2011/0284623 A1 | 11/2011 | Jones et al. |
| 2012/0208704 A1 | 8/2012 | Loew et al. |
| 2012/0270797 A1 | 10/2012 | Wittrup et al. |
| 2013/0079243 A1 | 3/2013 | Diem et al. |
| 2013/0079280 A1 | 3/2013 | Baca et al. |
| 2013/0096019 A1 | 4/2013 | Jacobs et al. |
| 2013/0096058 A1 | 4/2013 | Baca et al. |
| 2013/0196871 A1 | 8/2013 | Davis et al. |
| 2013/0237684 A1 | 9/2013 | Koide |
| 2013/0245238 A1 | 9/2013 | Davis et al. |
| 2013/0267676 A1 | 10/2013 | Koide |
| 2014/0057807 A1 | 2/2014 | Loew et al. |

FOREIGN PATENT DOCUMENTS

| | | |
|---|---|---|
| EP | 2141243 | 1/2010 |
| EP | 2154535 | 2/2010 |
| EP | 2379718 | 10/2011 |
| EP | 2385067 | 11/2011 |
| EP | 2439212 | 4/2012 |
| WO | WO 98/31700 | 7/1998 |
| WO | WO 98/56915 | 12/1998 |
| WO | WO 99/51773 | 10/1999 |
| WO | WO 00/34784 | 6/2000 |
| WO | WO 01/64942 | 9/2001 |
| WO | WO 02/04523 | 1/2002 |
| WO | WO 02/32925 | 4/2002 |
| WO | WO 02/081497 | 10/2002 |
| WO | WO 03/104418 | 12/2003 |
| WO | WO 2005/056764 | 6/2005 |
| WO | WO 2008/031098 | 3/2008 |
| WO | WO 2008/066752 | 6/2008 |
| WO | WO 2008/097497 | 8/2008 |
| WO | WO 2008/153745 A2 | 12/2008 |
| WO | WO 2009/023184 | 2/2009 |
| WO | WO 2009/025806 | 2/2009 |
| WO | WO 2009/058379 | 5/2009 |
| WO | WO 2009/073115 | 6/2009 |
| WO | WO 2009/083804 | 7/2009 |
| WO | WO 2009/086116 | 7/2009 |
| WO | WO 2009/102421 | 8/2009 |
| WO | WO 2009/133208 | 11/2009 |
| WO | WO 2009/142773 | 11/2009 |
| WO | WO 2009/142773 A2 | 11/2009 |
| WO | WO 2010/051274 | 5/2010 |
| WO | WO 2010/051310 | 5/2010 |
| WO | WO 2010/060095 | 5/2010 |
| WO | WO 2010/069913 | 6/2010 |
| WO | WO 2010/093627 | 8/2010 |
| WO | WO 2010/093627 A2 | 8/2010 |
| WO | WO 2010/093771 | 8/2010 |
| WO | WO 2011/020033 | 2/2011 |
| WO | WO 2011/035202 | 3/2011 |
| WO | WO 2011/051333 | 5/2011 |
| WO | WO 2011/051466 | 5/2011 |
| WO | WO 2011/092233 | 8/2011 |
| WO | WO 2011/100700 | 8/2011 |
| WO | WO 2011/103105 | 8/2011 |
| WO | WO 2011/103105 A1 | 8/2011 |
| WO | WO 2011/130324 | 10/2011 |
| WO | WO 2011/130328 | 10/2011 |
| WO | WO 2011/130354 | 10/2011 |
| WO | WO 2011/137319 | 11/2011 |
| WO | WO 2011/140086 | 11/2011 |
| WO | WO 2011/150133 | 12/2011 |
| WO | WO 2012/016245 | 2/2012 |
| WO | WO 2012/088006 | 6/2012 |
| WO | WO 2012/094653 | 7/2012 |
| WO | WO 2012/142515 | 10/2012 |
| WO | WO 2012/158678 | 11/2012 |
| WO | WO 2012/158678 A1 | 11/2012 |
| WO | WO 2012/158739 | 11/2012 |
| WO | WO 2013/049275 | 4/2013 |
| WO | WO 2013/067029 | 5/2013 |
| WO | WO2014/043344 | 3/2014 |
| WO | WO2014/120891 | 8/2014 |

OTHER PUBLICATIONS

Smith et al. The challenges of genome sequence annotation or "The devil is in the details". Nature Biotech 15: 1222-1223, 1997.*

Doerks et al. Protein annotation: detective work for function prediction. Trends in Genetics 14(6): 248-250, 1998.*

Brenner, S.E. Errors in genome function. Trends in Genetics 15(4): 132-133, 1999.*

Batori, Vincent, et al., "Exploring the potential of the monobody scaffold: effects of loop elongation on the stability of a fibronectin type III domain", Protein Engineering, 2002, vol. 15, No. 12, pp. 1015-1020.

Ackermann, Maximilian et al., "Anti-VEGFR2 and anti-IGF-1R-Adnectins inhibit Ewing's sarcoma A673-xenograft growth and normalize tumor vascular architecture," Angiogenesis, vol. 15:685-695 (2012).

Batori, Vincent et al., "Exploring the potential of the monobody scaffold: effects of loop elongation on the stability of a fibronectin type III domain," Protein Engineering, vol. 15(12):1015-1020 (2002).

Cota, Ernesto et al., "Folding of beta-sandwich proteins: Three-state transition of a fibronectin type III module," Protein Science, vol. 9:112-120 (2000).

Cota, Ernesto et al., "Two Proteins with the Same Structure Respond very Differently to Mutation: The Role of Plasticity in Protein Stability," J. Mol. Biol., vol. 302:713-725 (2000).

Dickinson, Craig D. et al., "Crystals of the Cell-binding Module of Fibronectin Obtained from a Series of Recombinant Fragments Differing in Length," J. Mol. Biol., vol. 238:123-127 (1994).

Dickinson, Craig D. et al., "Crystal Structure of the Tenth Type III Cell Adhesion Module of Human Fibronectin," J. Mol. Biol., vol. 236:1079-1092 (1994).

Dutta, Sanjib et al., "High-affinity fragment complementation of a fibronectin type III domain and its application to stability enhancement," Protein Science, vol. 14:2838-2848 (2005).

Dutta, Sanjib et al., "High-throughput analysis of the protein sequence-stability landscape using a quantitative 'yeast surface two-hybrid' system and fragment reconstitution," J. Mol. Biol., vol. 382(3):721-733 (2008).

Getmanova, Elena V. et al., "Antagonists to Human and Mouse Vascular Endothelial Growth Factor Receptor 2 Generated by Directed Protein Evolution In Vitro," Chemistry & Biology, vol. 13:549-556 (2006).

Gilbreth, Ryan N. et al., "A Dominant Conformational Role for Amino Acid Diversity in Minimalist Protein-Protein Interfaces," J. Mol. Biol., vol. 381(2):407-418 (2008).

Gilbreth, Ryan N. et al., "Isoform-specific monobody inhibitors of small ubiquitin-related modifiers engineered using structure-guided library design," PNAS, vol. 108(19):7751-7756 (2011).

Hackel, Benjamin J. et al., "Picomolar Affinity Fibronectin Domains Engineered Utilizing Loop Length Diversity, Recursive Mutagenesis, and Loop Shuffling," J. Mol. Biol., vol. 381:1238-1252 (2008).

Hackel, Benjamin J. et al., "The full amino acid repertoire is superior to serine/tyrosine for selection of high affinity immunoglobulin G binders from the fibronectin scaffold," Protein Engineering, Design & Selection, vol. 23(4):211-219 (2010).

Jacobs, Steven A. et al., "Design of novel FN3 domain with high stability by a consensus sequence approach," Protein Engineering, Design & Selection, vol. 25(3):107-117 (2012).

Jacobs, Steven A. et al., "FN3 Domain Engineering," Protein Engineering, Prof. Pravin Kaumaya (Ed.), www.intechopen.com, Chapter 7, pp. 145-162 (2012).

Karatan, Ece et al., "Molecular Recognition Properties of FN3 Monobodies that Bind the Src SH3 Domain," Chemistry & Biology, vol. 11:835-844 (2004).

Koide, Akiko et al., "Accelerating phage-display library selection by reversible and site-specific biotinylation," Protein Engineering, Design & Selection, vol. 22(11):685-690 (2009).

(56) References Cited

OTHER PUBLICATIONS

Koide, Shohei et al., "Directed Evolution of Fibronectin Type III Domain to Novel Ligand Binding Proteins," The Faseb Journal., vol. 11(9 Suppl.), Poster No. M40, p. A837, (1997).
Koide, Shohei et al., "Directed Evolution of Fibronectin Type III Domain to Novel Ligand Binding Proteins," The Faseb Journal, vol. 11(9):A1155, Poster No. 1739 (1997).
Koide, Akiko et al., "The Fibronectin Type III Domain as a Scaffold for Novel Binding Proteins", The Faseb Journal, J. Mol. Biol. 284: 1141-1151 (1998).
Koide, Shohei, "Engineerintg of recombinant crystallization chaperones," Curr. Opin. Struct. Biol., vol. 19(4):449-457 (2009).
Koide, Akiko et al., "High-affinity single-domain binding proteins with a binary-code interface," PNAS, vol. 104(16):6632-6637 (2007).
Koide, Akiko et al., "Probing protein conformational changes in living cells by using designer binding proteins: Application to the estrogen receptor," PNAS, vol. 99(3):1253-1258 (2002).
Koide, Akiko et al., "Stabilization of a Fibronectin Type III Domain by the Removal of Unfavorable Electrostatic Interactions on the Protein Surface," Biochemistry, vol. 40:10326-10333 (2001).
Koide, Shohei et al., "Target-Binding Proteins Based on the 10th Human Fibronectin Type III Domain ($^{10}$FN3)," Methods in Enzymology, vol. 503:135-156 (2012).
Koide, Akiko et al., "Teaching an old scaffold new tricks: Monobodies constructed using alternative surfaces of the FN3 scaffold," J. Mol. Biol., vol. 415(2):393-405 (2012).
Lipovsek, D., "Adnectins: engineered target-binding protein therapeutics," Protein Engineering, Design & Selection, vol. 24(1-2):3-9 (2011).
Lipovsek, Dasa et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J. Mol. Biol., vol. 368:1024-1041 (2007).
Lipovsek, Dasa et al., "In-vitro protein evolution by ribosome display and mRNA display," Journal of Immunological Methods, vol. 290:51-67 (2004).
Main, Alison L. et al., "The Three-Dimensional Structure of the Tenth Type III Module of Fibronectin: An Insight into RGD-Mediated Interactions," Cell, vol. 71:671-678 (1992).
Mamluk, Roni et al., "Anti-tumor effect of CT-322 as an adnectin inhibitor of vascular endothelial growth factor receptor-2," mAbs, Landes Bioscience vol. 2(2):199-208 (2010).
Olson, C. Anders at el., "Design, expression, and stability of a diverse protein library based on the human fibronectin type III domain," Protein Science, vol. 16:476-484 (2007).
Parker, M.H. et al., "Antibody mimics based on human fibronectin type three domain engineered for thermostability and high-affinity binding to vascular endothelial growth factor receptor two," Protein Engineering, Design & Selection, vol. 18(9):435-444 (2005).
Plaxco, Kevin W. et al., "Rapid refolding of a proline-rich all-beta-sheet fibronectin type III module," Proc. Natl. Acad. Sci. USA, vol. 93:10703-10706 (1996).
Ramamurthy, Vidhyashankar et al., "Structures of Adnectin/Protein Complexes Reveal an Expanded Binding Footprint," Structure, vol. 20:259-269 (2012).
Tolcher, Anthony W. et al., "Phase I and Pharmacokinetic Study of CT-322 (BMS-844203), a Targeted Adnectin Inhibitor of VEGFR-2 Based on a Domain of Human Fibronectin," Clinical Cancer Research, vol. 17(2):363-371 (2011).
Xu, Lihui et al., "Directed Evolution of High-Affinity Antibody Mimics Using mRNA Display," Chemistry & Biology, vol. 9:933-942 (2002).
Skerra, A. et al., "Alternative non-antibody scaffolds for molecular recognition," Current Opinion in Biotechnology, vol. 18, pp. 295-304 (2007).
International Search Report for Application No. PCT/US2014/014887; 7 pages; dated Aug. 11, 2015.
Database Geneseq [Online] "Human wild-type serum albumin binding adnectin polypeptide SEQ: 1.," Jan. 5, 2012, XP002784600, retrieved from EBI accession No. GSP:AZP63010 Database accession No. AZP63010.
Extended European Search Report, European Application No. EP18184239.4, dated Sep. 25, 2018, 11 pages.
Williams, M. et al., "Total Chemical Synthesis of a Folded Beta-Sandwich Protein Domain: An Analog of the Tenth Fibronectin Type 3 Module," J. Am. Chem. Soc., vol. 116:10797-10798 (1994).

\* cited by examiner

```
14Fn3  01  NVSPPRRARVTDATET-TITISWR-IKTETITGFQVDAVPANGQ--TP  44
10Fn3  01  VSDVPRDLEVVAATPT-SLLISWD-APAVTVRYYRITYGETGGN-SPV  45
 7Fn3  01  PLSPPTNLHLEANPDTGVLTVSWERSTTPDITGYRITTTPTNGQQGNS  44
              A      AB     B       BC      C       CD

14Fn3  45  IQRTIKPDVRSYTITGLQPGTDYKIYLYTLNDNARS----SPVVIDAST  89
10Fn3  46  QEFTVPGSKSTATISGLKPGVDYTITVYAVTGRGDSPASSKPISINYRT  94
 7Fn3  49  LEEVVHADQSSCTFDNLSPGLEYNVSVYTVKDDKES----VPISDTIIP  93
              D    DE   E    EF     F       FG         G
```

Figure 1

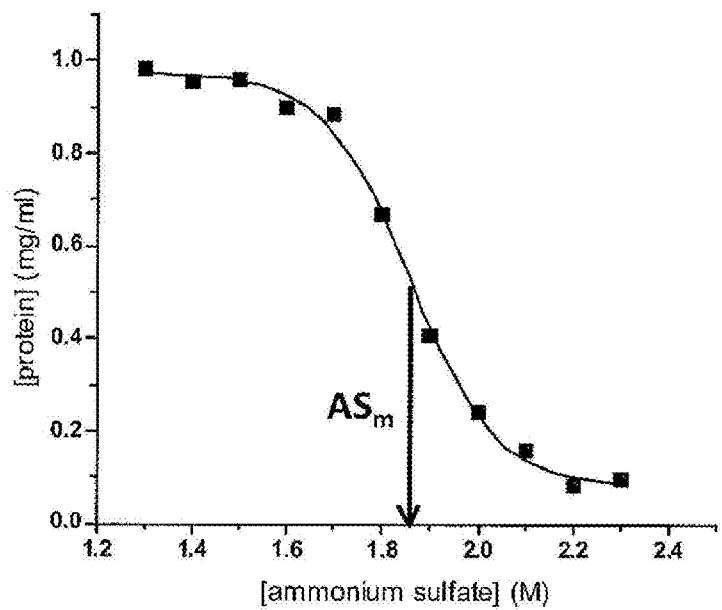

Figure 2

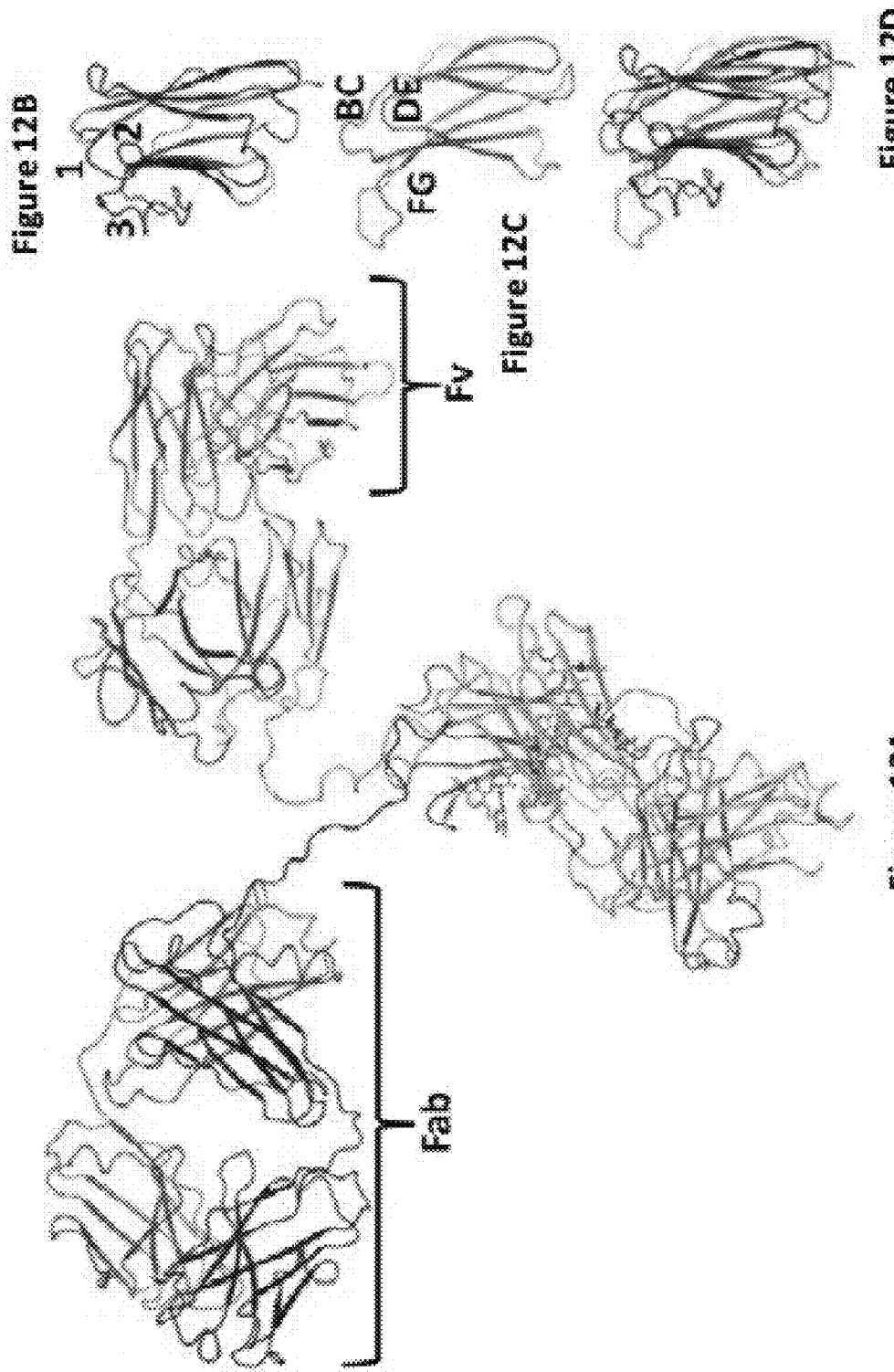

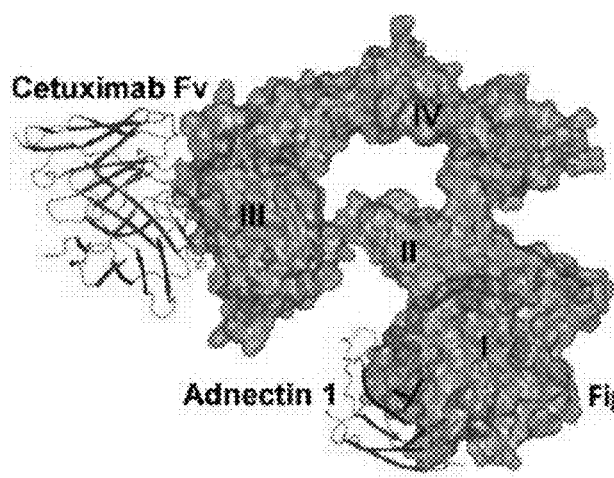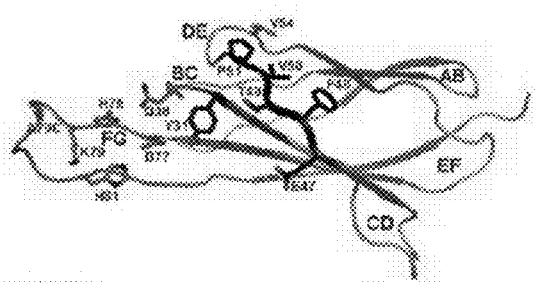
Figure 13A
Figure 13B
Figure 13C
Figure 13D
Figure 13E

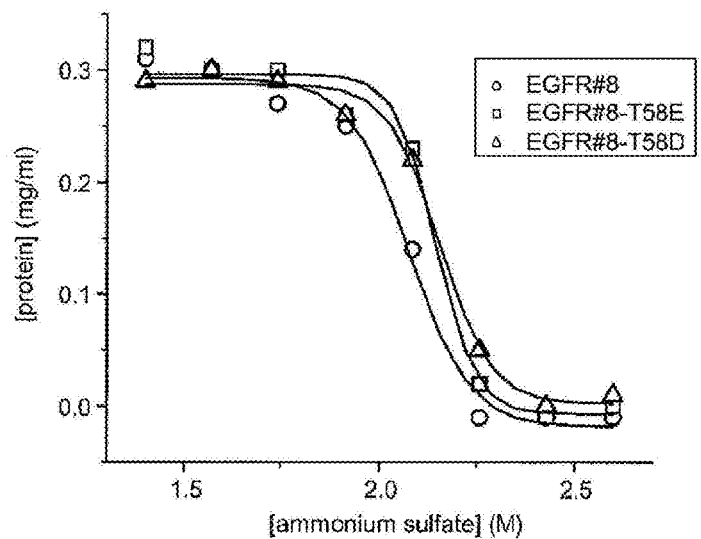
Figure 21
Figure 22A
Figure 22B
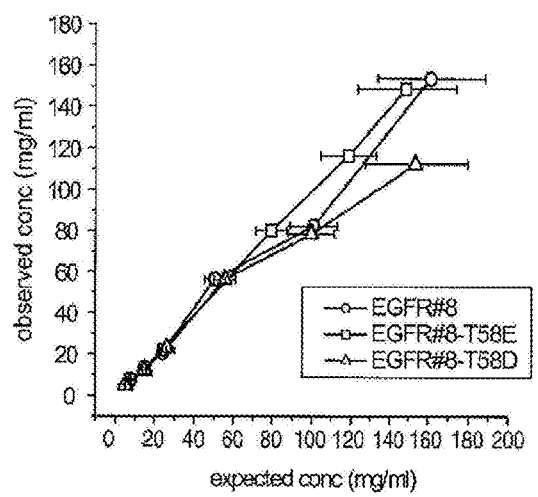
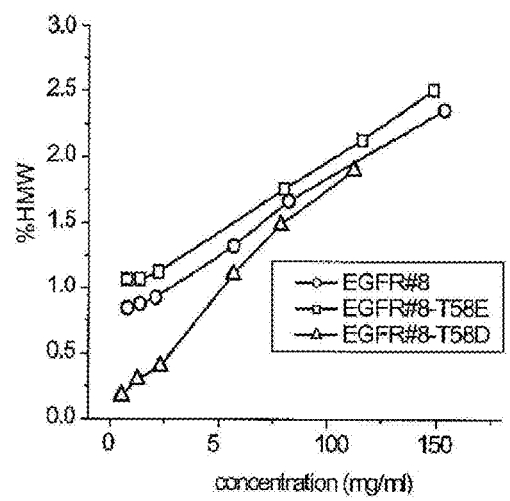

Figure 23A

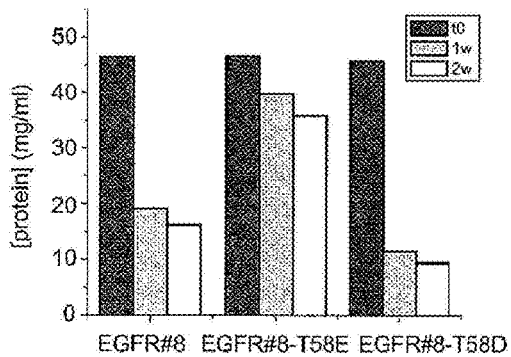

Figure 23B

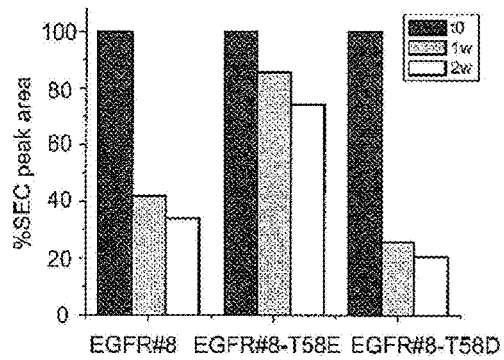

Figure 23C

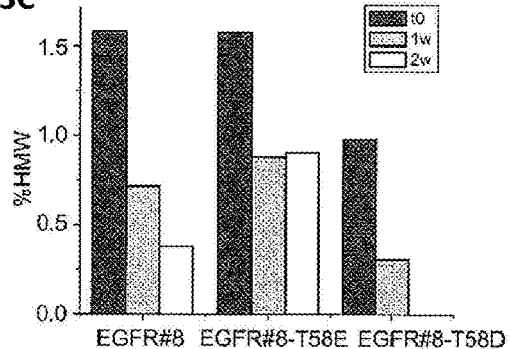

```
                        1                    BC                           DE      60
EGFR#4    (1)  VSDVPRDLEVVAATPTSLLISWYWEGLPYQYYRITYGETGGNSPVQEFTVPRDVNTATIS
EGFR#8    (1)  VSDVPRDLEVVAATPTSLLISWDSGRGSYQYYRITYGETGGNSPVQEFTVPGPVNTATIS
Consensus (1)  VSDVPRDLEVVAATPTSLLISW      YQYYRITYGETGGNSPVQEFTVP  V TATIS 61                    FG                         112
EGFR#4   (61)  GLKPGVDYTITVYAVTWYNPDTHEYIYHTIPISINYRTEIDKPSQHHHHHH
EGFR#8   (61)  GLKPGVDYTITVYAVTHKPHADGPHTYHESPISINYRTEIDKPSQHHHHHH
Consensus(61)  GLKPGVDYTITVYAVT        H YH PISINYRTEIDKPSQHHHHHH
```

Figure 24

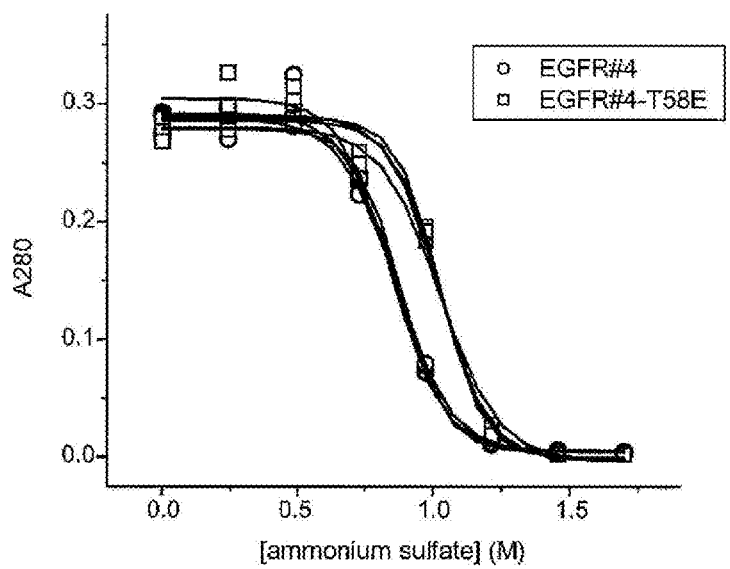
Figure 26
Figure 27A
Figure 27B
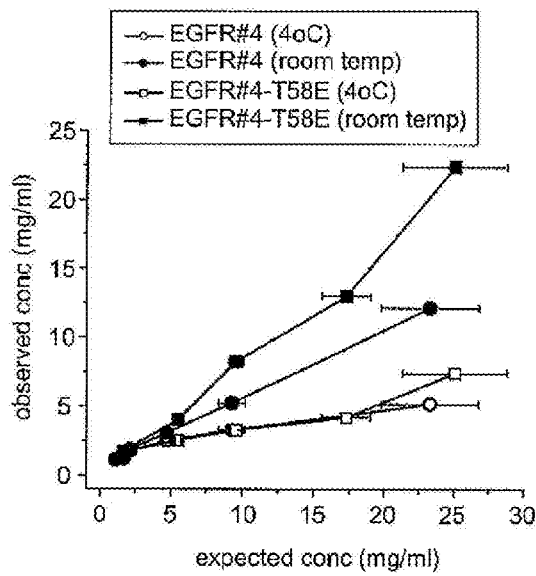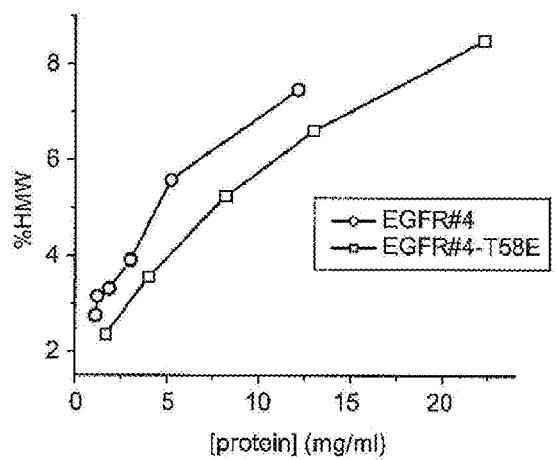

SEQUENCE LISTING

```
<160> NUMBER OF SEQ ID NOS: 87

<210> SEQ ID NO 1
<211> LENGTH: 101
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60
```

```
Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr Glu Ile
                 85                  90                  95

Asp Lys Pro Ser Gln
            100
```

<210> SEQ ID NO 2
<211> LENGTH: 101
<212> TYPE: PRT
<213> ORGANISM: Artificial Sequence
<220> FEATURE:
<223> OTHER INFORMATION: Synthetic polypeptide

<400> SEQUENCE: 2

```
Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr Glu Ile
                 85                  90                  95

Glu Lys Pro Ser Gln
            100
```

<210> SEQ ID NO 3
<211> LENGTH: 85
<212> TYPE: PRT
<213> ORGANISM: Homo sapiens

<400> SEQUENCE: 3

```
Leu Glu Val Val Ala Ala Thr Pro Thr Ser Leu Leu Ile Ser Trp Asp
  1               5                  10                  15

Ala Pro Ala Val Thr Val Arg Tyr Tyr Arg Ile Thr Tyr Gly Glu Thr
                 20                  25                  30

Gly Gly Asn Ser Pro Val Gln Glu Phe Thr Val Pro Gly Ser Lys Ser
             35                  40                  45

Thr Ala Thr Ile Ser Gly Leu Lys Pro Gly Val Asp Tyr Thr Ile Thr
 50                  55                  60

Val Tyr Ala Val Thr Gly Arg Gly Asp Ser Pro Ala Ser Ser Lys Pro
 65                  70                  75                  80

Ile Ser Ile Asn Tyr
             85
```

<210> SEQ ID NO 4
<211> LENGTH: 86
<212> TYPE: PRT
<213> ORGANISM: Homo sapiens

<400> SEQUENCE: 4

```
Glu Val Val Ala Ala Thr Pro Thr Ser Leu Leu Ile Ser Trp Asp Ala
  1               5                  10                  15

Pro Ala Val Thr Val Arg Tyr Tyr Arg Ile Thr Tyr Gly Glu Thr Gly
```

```
            20                  25                  30

Gly Asn Ser Pro Val Gln Glu Phe Thr Val Pro Gly Ser Lys Ser Thr
            35                  40                  45

Ala Thr Ile Ser Gly Leu Lys Pro Gly Val Asp Tyr Thr Ile Thr Val
 50                  55                  60

Tyr Ala Val Thr Gly Arg Gly Asp Ser Pro Ala Ser Ser Lys Pro Ile
 65                  70                  75                  80

Ser Ile Asn Tyr Arg Thr
                     85
```

<210> SEQ ID NO 5
<211> LENGTH: 94
<212> TYPE: PRT
<213> ORGANISM: Homo sapiens

<400> SEQUENCE: 5

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr
                    85                  90
```

<210> SEQ ID NO 6
<211> LENGTH: 95
<212> TYPE: PRT
<213> ORGANISM: Homo sapiens

<400> SEQUENCE: 6

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr Glu
                    85                  90                  95
```

<210> SEQ ID NO 7
<211> LENGTH: 96
<212> TYPE: PRT
<213> ORGANISM: Homo sapiens

<400> SEQUENCE: 7

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
            20                  25                  30
```

-continued

Arg Ile Thr Tyr Gly Glu Thr Gly Asn Ser Pro Val Gln Glu Phe
             35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                 85                  90                  95

<210> SEQ ID NO 8
<211> LENGTH: 97
<212> TYPE: PRT
<213> ORGANISM: Homo sapiens

<400> SEQUENCE: 8

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
             20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                 85                  90                  95

Asp

<210> SEQ ID NO 9
<211> LENGTH: 97
<212> TYPE: PRT
<213> ORGANISM: Homo sapiens

<400> SEQUENCE: 9

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
             20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                 85                  90                  95

Glu

<210> SEQ ID NO 10
<211> LENGTH: 98
<212> TYPE: PRT
<213> ORGANISM: Homo sapiens

<400> SEQUENCE: 10

Val Ser Asp Val Pro Arg Asp Leu Glu Val Val Ala Ala Thr Pro Thr
1               5                   10                  15

```
Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys

<210> SEQ ID NO 11
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 11

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Glu Lys

<210> SEQ ID NO 12
<211> LENGTH: 99
<212> TYPE: PRT
<213> ORGANISM: Homo sapiens

<400> SEQUENCE: 12

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro

<210> SEQ ID NO 13
<211> LENGTH: 99
```

```
<212> TYPE: PRT
<213> ORGANISM: Artificial Sequence
<220> FEATURE:
<223> OTHER INFORMATION: Synthetic polypeptide

<400> SEQUENCE: 13

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Glu Lys Pro

<210> SEQ ID NO 14
<211> LENGTH: 100
<212> TYPE: PRT
<213> ORGANISM: Homo sapiens

<400> SEQUENCE: 14

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser
            100

<210> SEQ ID NO 15
<211> LENGTH: 100
<212> TYPE: PRT
<213> ORGANISM: Artificial Sequence
<220> FEATURE:
<223> OTHER INFORMATION: Synthetic polypeptide

<400> SEQUENCE: 15

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
```

```
                65                  70                  75                  80
Ser Pro Ala Ser Ser Lys Pro Ile Ser Ile Asn Tyr Arg Thr Glu Ile
                    85                  90                  95

Glu Lys Pro Ser
            100

<210> SEQ ID NO 16
<211> LENGTH: 101
<212> TYPE: PRT
<213> ORGANISM: Homo sapiens

<400> SEQUENCE: 16

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
            50                  55                  60

Gly Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Thr Glu Ile
                    85                  90                  95

Asp Lys Pro Ser Gln
            100

<210> SEQ ID NO 17
<211> LENGTH: 166
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(166)
<223> OTHER INFORMATION: /note="see specification as filed for detailed
      description of substitutions and preferred embodiments"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
```

<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 17

```
Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
    130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr
                165
```

<210> SEQ ID NO 18
<211> LENGTH: 167
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)

```
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 18

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
            85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu
                165

<210> SEQ ID NO 19
<211> LENGTH: 168
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
```

```
           2-20, 2-15, 2-10, 2-8, 5-20, 5-15, 5-10, 5-8, 6-20, 6-15, 6-10,
           6-8, 2-7, 5-7, or 6-7 residues, wherein some positions may be
           absent
<220> FEATURE:
<221> NAME/KEY: MOD_RES
<222> LOCATION: (87)..(106)
<223> OTHER INFORMATION: Any amino acid and this region may encompass
           2-20, 2-15, 2-10, 2-8, 5-20, 5-15, 5-10, 5-8, 6-20, 6-15, 6-10,
           6-8, 2-7, 5-7, or 6-7 residues, wherein some positions may be
           absent
<220> FEATURE:
<221> NAME/KEY: MOD_RES
<222> LOCATION: (113)..(132)
<223> OTHER INFORMATION: Any amino acid and this region may encompass
           2-20, 2-15, 2-10, 2-8, 5-20, 5-15, 5-10, 5-8, 6-20, 6-15, 6-10,
           6-8, 2-7, 5-7, or 6-7 residues, wherein some positions may be
           absent
<220> FEATURE:
<221> NAME/KEY: MOD_RES
<222> LOCATION: (140)..(159)
<223> OTHER INFORMATION: Any amino acid and this region may encompass
           2-20, 2-15, 2-10, 2-8, 5-20, 5-15, 5-10, 5-8, 6-20, 6-15, 6-10,
           6-8, 2-7, 5-7, or 6-7 residues, wherein some positions may be
           absent

<400> SEQUENCE: 19

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile
                165

<210> SEQ ID NO 20
<211> LENGTH: 169
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
           2-20, 2-15, 2-10, 2-8, 5-20, 5-15, 5-10, 5-8, 6-20, 6-15, 6-10,
           6-8, 2-7, 5-7, or 6-7 residues, wherein some positions may be
           absent
<220> FEATURE:
<221> NAME/KEY: MOD_RES
<222> LOCATION: (39)..(58)
<223> OTHER INFORMATION: Any amino acid and this region may encompass
           2-20, 2-15, 2-10, 2-8, 5-20, 5-15, 5-10, 5-8, 6-20, 6-15, 6-10,
```

-continued

```
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 20

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp
                165

<210> SEQ ID NO 21
<211> LENGTH: 169
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
```

```
                    absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or
      6-7 residues, wherein some positions may be absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 21

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu
                165

<210> SEQ ID NO 22
<211> LENGTH: 170
<212> TYPE: PRT
<213> ORGANISM: Artificial Sequence
<220> FEATURE:
<223> OTHER INFORMATION: Synthetic polypeptide
```

```
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-

```
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 23

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
            35                  40                  45

Xaa Xaa Xaa Xaa Xaa Xaa Xaa Xaa Xaa Xaa Tyr Arg Ile Thr Tyr Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
            85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa
            130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys
```

<210> SEQ ID NO 24
<211> LENGTH: 171
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (39)..(58)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (64)..(83)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (87)..(106)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (113)..(132)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (140)..(159)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent

<400> SEQUENCE: 24

Val Ser Asp Val Pro Arg Asp Leu Glu Val Val Ala Ala Xaa Xaa Xaa
1               5                  10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Tyr Arg Ile Thr Tyr Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa

```
                130             135             140
Xaa Xaa Xaa Xaa Xaa Xaa Xaa Xaa Xaa Xaa Xaa Xaa Xaa Xaa Ile
145                 150             155             160

Ser Ile Asn Tyr Arg Thr Glu Ile Asp Lys Pro
                165             170

<210> SEQ ID NO 25
<211> LENGTH: 171
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 25

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa
            35                  40                  45

Xaa Xaa Xaa Xaa Xaa Xaa Xaa Xaa Xaa Tyr Arg Ile Thr Tyr Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa
            85                  90                  95

Xaa Xaa Xaa Xaa Xaa Xaa Xaa Xaa Xaa Xaa Ala Thr Ile Ser Gly Leu
```

```
            100                 105                 110
Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
        130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys Pro
                165                 170

<210> SEQ ID NO 26
<211> LENGTH: 172
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 26

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
            35                  40                  45

Xaa Xaa Xaa Xaa Xaa Xaa Xaa Xaa Xaa Tyr Arg Ile Thr Tyr Xaa
            50                  55                  60

Xaa Xaa Xaa Xaa Xaa Xaa Xaa Xaa Xaa Xaa Xaa Xaa Xaa Xaa Xaa
```

-continued

```
                65                  70                  75                  80
Xaa Xaa Xaa Phe Thr Val Xaa Xaa Xaa Xaa Xaa Xaa Xaa Xaa
                    85                  90                  95
Xaa Xaa Xaa Xaa Xaa Xaa Xaa Xaa Xaa Ala Thr Ile Ser Gly Leu
                    100                 105                 110
Xaa Xaa Xaa Xaa Xaa Xaa Xaa Xaa Xaa Xaa Xaa Xaa Xaa Xaa Xaa
                    115                 120                 125
Xaa Xaa Xaa Xaa Tyr Thr Ile Thr Val Tyr Ala Xaa Xaa Xaa Xaa
                130                 135                 140
Xaa Xaa Xaa Xaa Xaa Xaa Xaa Xaa Xaa Xaa Xaa Xaa Xaa Xaa Ile
            145                 150                 155                 160
Ser Ile Asn Tyr Arg Thr Glu Ile Asp Lys Pro Ser
                    165                 170

<210> SEQ ID NO 27
<211> LENGTH: 172
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 27

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Leu Leu Ile Ser Trp Xaa Xaa Xaa Xaa Xaa Xaa Xaa Xaa Xaa
```

```
            35                  40                  45
Xaa Xaa Xaa Xaa Xaa Xaa Xaa Xaa Xaa Xaa Tyr Arg Ile Thr Tyr Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Phe Thr Val Xaa Xaa Xaa Xaa Xaa Xaa Xaa Xaa Xaa Xaa
             85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys Pro Ser
            165                 170

<210> SEQ ID NO 28
<211> LENGTH: 173
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 28

Val Ser Asp Val Pro Arg Asp Leu Glu Val Val Ala Ala Xaa Xaa Xaa
```

```
1               5                   10                  15
Xaa Xaa Xaa Xaa Xaa Xaa Xaa Xaa Xaa Xaa Xaa Xaa Xaa Xaa Xaa
            20                  25                  30
Xaa Leu Leu Ile Ser Trp Xaa Xaa Xaa Xaa Xaa Xaa Xaa Xaa Xaa
            35                  40                  45
Xaa Xaa Xaa Xaa Xaa Xaa Xaa Xaa Xaa Tyr Arg Ile Thr Tyr Xaa
        50                  55                  60
Xaa Xaa Xaa Xaa Xaa Xaa Xaa Xaa Xaa Xaa Xaa Xaa Xaa Xaa Xaa
65                  70                  75                  80
Xaa Xaa Xaa Phe Thr Val Xaa Xaa Xaa Xaa Xaa Xaa Xaa Xaa Xaa
                85                  90                  95
Xaa Xaa Xaa Xaa Xaa Xaa Xaa Xaa Xaa Ala Thr Ile Ser Gly Leu
            100                 105                 110
Xaa Xaa Xaa Xaa Xaa Xaa Xaa Xaa Xaa Xaa Xaa Xaa Xaa Xaa Xaa
            115                 120                 125
Xaa Xaa Xaa Xaa Tyr Thr Ile Thr Val Tyr Ala Xaa Xaa Xaa Xaa
        130                 135                 140
Xaa Xaa Xaa Xaa Xaa Xaa Xaa Xaa Xaa Xaa Xaa Xaa Xaa Xaa Ile
145                 150                 155                 160
Ser Ile Asn Tyr Arg Thr Glu Ile Asp Lys Pro Ser Gln
                165                 170

<210> SEQ ID NO 29
<211> LENGTH: 173
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
```

6-8, 2-7, 5-7, or 6-7 residues, wherein some positions may be
        absent

<400> SEQUENCE: 29

Val Ser Asp Val Pro Arg Asp Leu Glu Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
        35                  40                  45

Xaa Xaa Xaa Xaa Xaa Xaa Xaa Xaa Xaa Tyr Arg Ile Thr Tyr Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
            85                  90                  95

Xaa Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys Pro Ser Gln
                165                 170

<210> SEQ ID NO 30
<211> LENGTH: 10
<212> TYPE: PRT
<213> ORGANISM: Artificial Sequence
<220> FEATURE:
<223> OTHER INFORMATION: Synthetic peptide

<400> SEQUENCE: 30

Met Gly Val Ser Asp Val Pro Arg Asp Leu
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide

<400> SEQUENCE: 31

Gly Val Ser Asp Val Pro Arg Asp Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be absent
<220> FEATURE:
<221> NAME/KEY: VARIANT
<222> LOCATION: (1)..(2)

```
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 32

Met Gly Ser Asp Val Pro Arg Asp Leu
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 33

Met Gly Asp Val Pro Arg Asp Leu
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"
```

```
<400> SEQUENCE: 34

Met Gly Val Pro Arg Asp Leu
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 35

Met Gly Pro Arg Asp Leu
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 36

Met Gly Arg Asp Leu
1               5

<210> SEQ ID NO 37
<211> LENGTH: 4
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 37

Met Gly Asp Leu
1

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide

<400> SEQUENCE: 38

Met Ala Ser Thr Ser Gly
1               5

<210> SEQ ID NO 39
<211> LENGTH: 4
<212> TYPE: PRT
<213> ORGANISM: Artificial Sequence
<220> FEATURE:
<223> OTHER INFORMATION: Synthetic peptide

<400> SEQUENCE: 39

Glu Ile Glu Lys
1

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide

<400> SEQUENCE: 40

Glu Gly Ser Gly Cys
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide

<400> SEQUENCE: 41

Glu Ile Glu Lys Pro Cys Gln
1               5

<210> SEQ ID NO 42
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

Glu Ile Glu Lys Pro Ser Gln
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic peptide

<400> SEQUENCE: 43

Glu Ile Glu Lys Pro
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide

<400> SEQUENCE: 44

Glu Ile Glu Lys Pro Ser
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide

<400> SEQUENCE: 45

Glu Ile Glu Lys Pro Cys
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 46

His His His His His His
1               5

<210> SEQ ID NO 47
<211> LENGTH: 4
<212> TYPE: PRT
<213> ORGANISM: Artificial Sequence
<220> FEATURE:
<223> OTHER INFORMATION: Synthetic peptide

<400> SEQUENCE: 47

Glu Ile Asp Lys
1

<210> SEQ ID NO 48
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 48

Glu Ile Asp Lys Pro Cys Gln
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide

<400> SEQUENCE: 49

Glu Ile Asp Lys Pro Ser Gln
1               5

<210> SEQ ID NO 50
<211> LENGTH: 91
<212> TYPE: PRT
<213> ORGANISM: Artificial Sequence
<220> FEATURE:
<223> OTHER INFORMATION: Synthetic polypeptide

<400> SEQUENCE: 50

Met Pro Ala Pro Thr Asp Leu Arg Phe Thr Asn Glu Thr Pro Ser Ser
1               5                   10                  15

Leu Leu Ile Ser Trp Thr Pro Pro Arg Val Gln Ile Thr Gly Tyr Ile
            20                  25                  30

Ile Arg Tyr Gly Pro Val Gly Ser Asp Gly Arg Val Lys Glu Phe Thr
        35                  40                  45

Val Pro Pro Ser Val Ser Ser Ala Thr Ile Thr Gly Leu Lys Pro Gly
    50                  55                  60

Thr Glu Tyr Thr Ile Ser Val Ile Ala Leu Lys Asp Asn Gln Glu Ser
65                  70                  75                  80

Glu Pro Leu Arg Gly Arg Val Thr Thr Gly Gly
                85                  90

<210> SEQ ID NO 51
<211> LENGTH: 4
<212> TYPE: PRT
<213> ORGANISM: Artificial Sequence
<220> FEATURE:
<223> OTHER INFORMATION: Synthetic peptide

<400> SEQUENCE: 51

Thr Pro Ser Ser
1

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Thr Pro Pro Arg Val Gln Ile
1               5

<210> SEQ ID NO 53
```

```
<211> LENGTH: 6
<212> TYPE: PRT
<213> ORGANISM: Artificial Sequence
<220> FEATURE:
<223> OTHER INFORMATION: Synthetic peptide

<400> SEQUENCE: 53

Val Gly Ser Asp Gly Arg
1               5

<210> SEQ ID NO 54
<211> LENGTH: 4
<212> TYPE: PRT
<213> ORGANISM: Artificial Sequence
<220> FEATURE:
<223> OTHER INFORMATION: Synthetic peptide

<400> SEQUENCE: 54

Pro Ser Val Ser
1

<210> SEQ ID NO 55
<211> LENGTH: 5
<212> TYPE: PRT
<213> ORGANISM: Artificial Sequence
<220> FEATURE:
<223> OTHER INFORMATION: Synthetic peptide

<400> SEQUENCE: 55

Gly Leu Lys Pro Gly
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic peptide

<400> SEQUENCE: 56

Lys Asp Asn Gln Glu Ser Glu Pro
1               5

<210> SEQ ID NO 57
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 57

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
                20                  25                  30

Ile Thr Tyr Thr Pro Ser Asn Gly Pro Gly Glu Pro Lys Glu Leu Thr
            35                  40                  45

Val Pro Pro Ser Ser Thr Ser Val Thr Ile Thr Gly Ile Thr Pro Gly
        50                  55                  60

Val Glu Tyr Val Val Ser Val Tyr Ala Leu Lys Asp Asn Gln Glu Ser
65                  70                  75                  80

Pro Pro Leu Val Gly Thr Cys Thr Thr
                85
```

```
<210> SEQ ID NO 58
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 58

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85

<210> SEQ ID NO 59
<211> LENGTH: 4
<212> TYPE: PRT
<213> ORGANISM: Artificial Sequence
<220> FEATURE:
<223> OTHER INFORMATION: Synthetic peptide

<400> SEQUENCE: 59

Thr Glu Asp Ser
1

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Thr Ala Pro Asp Ala Ala Phe
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic peptide

<400> SEQUENCE: 61

Ser Glu Lys Val Gly Glu
1               5

<210> SEQ ID NO 62
<211> LENGTH: 4
<212> TYPE: PRT
<213> ORGANISM: Artificial Sequence
<220> FEATURE:
<223> OTHER INFORMATION: Synthetic peptide

<400> SEQUENCE: 62

Gly Ser Glu Arg
1
```

<210> SEQ ID NO 63
<211> LENGTH: 5
<212> TYPE: PRT
<213> ORGANISM: Artificial Sequence
<220> FEATURE:
<223> OTHER INFORMATION: Synthetic peptide

<400> SEQUENCE: 63

Gly Leu Lys Pro Gly
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Lys Gly Gly His Arg Ser Asn
1               5

<210> SEQ ID NO 65
<211> LENGTH: 93
<212> TYPE: PRT
<213> ORGANISM: Homo sapiens

<400> SEQUENCE: 65

Pro Leu Ser Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
        35                  40                  45

Leu Glu Glu Val Val His Ala Asp Gln Ser Ser Cys Thr Phe Asp Asn
50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro
                85                  90

<210> SEQ ID NO 66
<211> LENGTH: 89
<212> TYPE: PRT
<213> ORGANISM: Homo sapiens

<400> SEQUENCE: 66

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

-continued

```
<210> SEQ ID NO 67
<211> LENGTH: 108
<212> TYPE: PRT
<213> ORGANISM: Homo sapiens

<400> SEQUENCE: 67
```

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Pro Val His Thr Ala Thr Ile Ser Gly Leu
    50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln
            100                 105

```
<210> SEQ ID NO 68
<211> LENGTH: 108
<212> TYPE: PRT
<213> ORGANISM: Homo sapiens

<400> SEQUENCE: 68
```

Met Gly Val Ser Asp Val Pro Arg Asp Leu Glu Val Val Ala Ala Thr
1               5                   10                  15

Pro Thr Ser Leu Leu Ile Ser Trp Tyr Trp Glu Gly Leu Pro Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Arg Asp Val Asn Thr Ala Thr Ile Ser Gly Leu
    50                  55                  60

Lys Pro Gly Val Asp Tyr Thr Ile Thr Val Tyr Ala Val Thr Asp Trp
65                  70                  75                  80

Tyr Asn Pro Asp Thr His Glu Tyr Ile Tyr His Thr Ile Pro Ile Ser
                85                  90                  95

Ile Asn Tyr Arg Thr Glu Ile Asp Lys Pro Ser Gln
            100                 105

```
<210> SEQ ID NO 69
<211> LENGTH: 108
<212> TYPE: PRT
<213> ORGANISM: Homo sapiens

<400> SEQUENCE: 69
```

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
        35                  40                  45

Glu Phe Thr Val Pro Gly Pro Val His Thr Ala Glu Ile Ser Gly Leu
    50                  55                  60

Lys Pro Gly Val Asp Tyr Thr Ile Thr Val Tyr Ala Val Thr Asp His
65                  70                  75                  80

-continued

Lys Pro His Ala Asp Gly Pro His Thr Tyr His Glu Ser Pro Ile Ser
            85                  90                  95

Ile Asn Tyr Arg Thr Glu Ile Asp Lys Pro Ser Gln
            100                 105

<210> SEQ ID NO 70
<211> LENGTH: 108
<212> TYPE: PRT
<213> ORGANISM: Homo sapiens

<400> SEQUENCE: 70

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Pro Val His Thr Ala Asp Ile Ser Gly Leu
        50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Ser Pro Ile Ser
            85                  90                  95

Ile Asn Tyr Arg Thr Glu Ile Asp Lys Pro Ser Gln
            100                 105

<210> SEQ ID NO 71
<211> LENGTH: 108
<212> TYPE: PRT
<213> ORGANISM: Homo sapiens

<400> SEQUENCE: 71

Met Gly Val Ser Asp Val Pro Arg Asp Leu Glu Val Val Ala Ala Thr
1               5                   10                  15

Pro Thr Ser Leu Leu Ile Ser Trp Tyr Trp Glu Gly Leu Pro Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Arg Asp Val Asn Thr Ala Glu Ile Ser Gly Leu
        50                  55                  60

Lys Pro Gly Val Asp Tyr Thr Ile Thr Val Tyr Ala Val Thr Asp Trp
65                  70                  75                  80

Tyr Asn Pro Asp Thr His Glu Tyr Ile Tyr His Thr Ile Pro Ile Ser
            85                  90                  95

Ile Asn Tyr Arg Thr Glu Ile Asp Lys Pro Ser Gln
            100                 105

<210> SEQ ID NO 72
<211> LENGTH: 5
<212> TYPE: PRT
<213> ORGANISM: Homo sapiens

<400> SEQUENCE: 72

Glu Phe Thr Val Pro
1               5

<210> SEQ ID NO 73
<211> LENGTH: 5

<212> TYPE: PRT
<213> ORGANISM: Homo sapiens

<400> SEQUENCE: 73

Thr Asp His Lys Pro
1               5

<210> SEQ ID NO 74
<211> LENGTH: 4
<212> TYPE: PRT
<213> ORGANISM: Homo sapiens

<400> SEQUENCE: 74

Thr Gln Leu Gly
1

<210> SEQ ID NO 75
<211> LENGTH: 5
<212> TYPE: PRT
<213> ORGANISM: Homo sapiens

<400> SEQUENCE: 75

His Asp Tyr Pro Tyr
1               5

<210> SEQ ID NO 76
<211> LENGTH: 10
<212> TYPE: PRT
<213> ORGANISM: Homo sapiens

<400> SEQUENCE: 76

Ser Tyr Lys Tyr Asp Met Gln Tyr Ser Pro
1               5                   10

<210> SEQ ID NO 77
<211> LENGTH: 8
<212> TYPE: PRT
<213> ORGANISM: Homo sapiens

<400> SEQUENCE: 77

Ser Trp Glu His Asp Tyr Pro Tyr
1               5

<210> SEQ ID NO 78
<211> LENGTH: 11
<212> TYPE: PRT
<213> ORGANISM: Homo sapiens

<400> SEQUENCE: 78

Val Thr Ser Ser Tyr Lys Tyr Asp Met Gln Tyr
1               5                   10

<210> SEQ ID NO 79
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 79

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Pro Val His Thr Ala Thr Ile Ser Gly Leu
 50                  55                  60

Lys Pro Gly Val Asp Tyr Thr Ile Thr Val Tyr Ala Val Thr Asp Asp
 65                  70                  75                  80

His Lys Pro His Ala Asp Gly Pro His Thr Tyr His Glu Ser Pro Ile
                 85                  90                  95

Ser Ile Asn Tyr Arg Thr Glu Ile Asp Lys Pro Ser Gln His His
            100                 105                 110

His His His
       115

<210> SEQ ID NO 80
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 80

Met Gly Val Ser Asp Val Pro Arg Asp Leu Glu Val Val Ala Ala Thr
 1               5                  10                  15

Pro Thr Ser Leu Leu Ile Ser Trp Glu His Asp Tyr Pro Tyr Arg Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asp Val Asp Thr Ala Thr Ile Ser Gly Leu
 50                  55                  60

Lys Pro Gly Val Asp Tyr Thr Ile Thr Val Tyr Ala Val Thr Ser Ser
 65                  70                  75                  80

Tyr Lys Tyr Asp Met Gln Tyr Ser Pro Ile Ser Ile Asn Tyr Arg Thr
                 85                  90                  95

Glu Ile Asp Lys Pro Ser Gln His His His His His His
            100                 105

<210> SEQ ID NO 81
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 81

Val Ser Asp Val Pro Arg Asp Leu Glu Val Val Ala Ala Thr Pro Thr
 1               5                  10                  15

Ser Leu Leu Ile Ser Trp Tyr Trp Glu Gly Leu Pro Tyr Gln Tyr Tyr
                20                  25                  30

Arg Ile Thr Tyr Gly Glu Thr Gly Gly Asn Ser Pro Val Gln Glu Phe
            35                  40                  45

Thr Val Pro Arg Asp Val Asn Thr Ala Thr Ile Ser Gly Leu Lys Pro
 50                  55                  60

Gly Val Asp Tyr Thr Ile Thr Val Tyr Ala Val Thr Asp Trp Tyr Asn
 65                  70                  75                  80

Pro Asp Thr His Glu Tyr Ile Tyr Thr Ile Pro Ile Ser Ile Asn
                 85                  90                  95

Tyr Arg Thr Glu Ile Asp Lys Pro Ser Gln His His His His His His
            100                 105                 110

```
<210> SEQ ID NO 82
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 82

Val Ser Asp Val Pro Arg Asp Leu Glu Val Val Ala Ala Thr Pro Thr
1               5                   10                  15

Ser Leu Leu Ile Ser Trp Asp Ser Gly Arg Gly Ser Tyr Gln Tyr Tyr
            20                  25                  30

Arg Ile Thr Tyr Gly Glu Thr Gly Gly Asn Ser Pro Val Gln Glu Phe
        35                  40                  45

Thr Val Pro Gly Pro Val His Thr Ala Thr Ile Ser Gly Leu Lys Pro
    50                  55                  60

Gly Val Asp Tyr Thr Ile Thr Val Tyr Ala Val Thr Asp His Lys Pro
65                  70                  75                  80

His Ala Asp Gly Pro His Thr Tyr His Glu Ser Pro Ile Ser Ile Asn
                85                  90                  95

Tyr Arg Thr Glu Ile Asp Lys Pro Ser Gln His His His His His His
            100                 105                 110

<210> SEQ ID NO 83
<211> LENGTH: 5
<212> TYPE: PRT
<213> ORGANISM: Homo sapiens

<400> SEQUENCE: 83

Glu Phe Thr Val Pro
1               5

<210> SEQ ID NO 84
<211> LENGTH: 6
<212> TYPE: PRT
<213> ORGANISM: Homo sapiens

<400> SEQUENCE: 84

Glu His Asp Tyr Pro Tyr
1               5

<210> SEQ ID NO 85
<211> LENGTH: 10
<212> TYPE: PRT
<213> ORGANISM: Homo sapiens

<400> SEQUENCE: 85

Thr Ser Ser Tyr Lys Tyr Asp Met Gln Tyr
1               5                   10

<210> SEQ ID NO 86
<211> LENGTH: 114
<212> TYPE: PRT
<213> ORGANISM: Artificial Sequence
<220> FEATURE:
<223> OTHER INFORMATION: Synthetic

<400> SEQUENCE: 86

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
```

```
                  20                  25                  30
Tyr Tyr Arg Ile Thr Tyr Gly Glu Thr Gly Gly Asn Ser Pro Val Gln
            35                  40                  45
Glu Phe Thr Val Pro Gly Pro Val His Thr Ala Thr Ile Ser Gly Leu
 50                  55                  60
Lys Pro Gly Val Asp Tyr Thr Ile Thr Val Tyr Ala Val Thr Asp His
 65                  70                  75                  80
Lys Pro His Ala Asp Gly Pro His Thr Tyr His Glu Ser Pro Ile Ser
                85                  90                  95
Ile Asn Tyr Arg Thr Glu Ile Asp Lys Pro Ser Gln His His His His
            100                 105                 110
His His

<210> SEQ ID NO 87
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(28)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (78)..(85)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid

<400> SEQUENCE: 87

Val Ser Asp Val Pro Arg Asp Leu Glu Val Val Ala Ala Thr Pro Thr
 1               5                  10                  15
Ser Leu Leu Ile Ser Trp Xaa Xaa Xaa Xaa Xaa Xaa Tyr Gln Tyr Tyr
            20                  25                  30
Arg Ile Thr Tyr Gly Glu Thr Gly Gly Asn Ser Pro Val Gln Glu Phe
            35                  40                  45
Thr Val Pro Xaa Xaa Val Xaa Thr Ala Thr Ile Ser Gly Leu Lys Pro
 50                  55                  60
Gly Val Asp Tyr Thr Ile Thr Val Tyr Ala Val Thr Asp Xaa Xaa Xaa
 65                  70                  75                  80
Xaa Xaa Xaa Xaa Xaa His Xaa Tyr His Xaa Xaa Pro Ile Ser Ile Asn
                85                  90                  95
Tyr Arg Thr Glu Ile Asp Lys Pro Ser Gln His His His His His His
            100                 105                 110
```

FIBRONECTIN TYPE III DOMAIN PROTEINS WITH ENHANCED SOLUBILITY

REFERENCE TO RELATED APPLICATIONS

This application is a 35 U.S.C. 371 national stage filing of International Application No. PCT/US2014/014887, filed Feb. 5, 2014, which claims the benefit of U.S. Provisional Application No. 61/761,452. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on May 23, 2017, is named MXI_557US_Sequence_Listing.txt and is 81,268 bytes in size.

BACKGROUND

Fibronectin is a large protein which plays essential roles in the formation of extracellular matrix and cell-cell interactions; it consists of many repeats of three types (types I, II, and III) of small domains. Fibronectin type III (Fn3) domains are frequently found as portions of cell adhesion molecules, cell surface hormone and cytokine receptors, chaperones, and carbohydrate-binding domains. A wildtype Fn3 domain is small, monomeric, soluble, and stable. It lacks disulfide bonds and, therefore, is stable under reducing conditions. For reviews see Bork & Doolittle, 1992, Proc Natl Acad Sci USA 89(19):8990-4; Bork et al., 1994, J Mol Biol. 242(4):309-20; Campbell & Spitzfaden, Structure 2(5):333-7 (1994); Harpez & Chothia, 1994, J Mol Biol. 238(4):528-39.

Fibronectin based scaffolds are a family of proteins having an immunoglobulin like fold. These proteins, which generally make use of a scaffold derived from a fibronectin type III (Fn3) or Fn3-like domain, function in a manner characteristic of natural or engineered antibodies (e.g., polyclonal, monoclonal, or single-chain antibodies) and contain loops that are analogously located to the complementarity determining regions (CDRs) of an antibody variable domain. In addition, fibronectin based scaffolds possess structural advantages. Specifically, the structures of these antibody mimics have frequently been optimized for optimal folding, stability, and solubility, even under conditions that normally lead to the loss of structure and function in antibodies. An example of fibronectin-based scaffold proteins are Adnectins (by Adnexus, a wholly owned subsidiary of Bristol-Myers Squibb), which are a class of targeted biologics derived from the tenth type III domain ($^{10}$Fn3) of human fibronectin. It has been shown that the CDR-like loop regions of the fibronectin based scaffolds can be modified to evolve a protein capable of binding to a target of interest. For example, U.S. Pat. No. 7,115,396 describes Fn3 domain proteins wherein alterations to the BC, DE, and FG loops result in high affinity TNFα binders. U.S. Pat. No. 7,858,739 describes Fn3 domain proteins wherein alterations to the BC, DE, and FG loops result in high affinity VEGFR2 binders. The first Adnectin tested in a clinical trial, CT-322, targets vascular endothelial growth factor receptor-2 (VEGFR-2). Pre-clinical (Mamluk, R. et al., 2010, mAbs 2, 199-208) and Phase I studies on CT-322 (Bloom, L. & Calabro, V., 2009, Drug Discov. Today 14, 949-955; Molckovsky, A. & Siu, L. L., 2008, J. Hematol. Oncol. 1, 20; Tolcher, A. W. et al., 2011, Clin. Cancer Res. 17, 363-371) demonstrated that it was well tolerated and produced pharmacological effects expected from the inhibition of the VEGFR-2 pathway.

Protein aggregation can be a challenge for protein based therapeutics, such as fibronectin based scaffolds, in particular where high protein concentration formulations are desirable for drug delivery. In addition, aggregation can cause challenges with production and manufacturing, lead to undesirable activities such as unintended receptor agonism, and potentially impact drug safety by induction of an immune response. See Shire, S. J. et al., 2004, J Pharm Sci. 93: 1390-402; Vazquez-Rey, M. and Lang, D. A., 2011, Biotechnol Bioeng 108: 1494-508; and Barker, M. P. et al., 2010, Self Nonself 1: 314-322. Consequently, it is desirable to generate and/or select protein therapeutics, such as fibronectin based scaffolds, that have enhanced solubility or reduced aggregation propensity.

SUMMARY

Provided herein are polypeptides comprising a modified fibronectin type III (Fn3) domain, wherein the modified Fn3 domain comprises an amino acid sequence wherein the amino acid corresponding to residue 58 of SEQ ID NO: 1 is mutated, and wherein the solubility of the modified Fn3 domain is enhanced relative to the solubility of a Fn3 domain wherein the amino acid corresponding to residue 58 of SEQ ID NO: 1 is not mutated, provided that in the modified Fn3 domain,
  (i) the amino acid corresponding to residue 58 of SEQ ID NO: 1 is not mutated to Ala (A) or Ile (I);
  (ii) if the amino acid corresponding to residue 58 of SEQ ID NO: 1 is mutated to Ile (I), at least one of the amino acids corresponding to residues 23-29, 52-54 and 56 of SEQ ID NO:1 is the same as the corresponding residue of SEQ ID NO: 1;
  (iii) if the amino acid corresponding to residue 58 of SEQ ID NO: 1 is mutated to Ala (A), at least one of the amino acids corresponding to residues 23, 24, 26, 29, 52-54, and 56 of SEQ ID NO:1 is the same as the corresponding residue of SEQ ID NO: 1; or
  (iv) if the amino acid corresponding to residue 58 of SEQ ID NO: 1 is mutated to Ala (A), three residues of the BC loop are the same as the corresponding residues in the BC loop of SEQ ID NO:1, or two residues of the DE loop are the same as the corresponding residues in the DE loop of SEQ ID NO:1.

Also provided herein are libraries comprising a plurality of the polypeptides described herein, methods for identifying a polypeptide that binds to a target comprising screening a library described herein, and isolated polypeptides identified by such a method.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1. shows an alignment of human wildtype $^{7}$Fn3 (SEQ ID NO. 65), $^{10}$Fn3 (SEQ ID NO. 5), and $^{14}$Fn3 (SEQ ID NO. 66) domains. The beta-strands are shown in bold and underlined. The Thr residues corresponding to T58 of the human wildtype $^{10}$Fn3 are boxed.

FIG. 2 shows an example salting out curve for 1 mg/ml adnectin IGFR #1. The data are fit to a sigmoidal curve function from which the midpoint of the salting out transition ($AS_m$) is determined.

FIG. 3A) EGFR #1-7 and IGFR #1 adnectins. FIG. 3B) EI-tandem adnectins. FIG. 3C) PEGylated EI-tandem adnectins (EI-tandem-PEG), where the inset shows the data with an expanded x-axis. Symbols correspond to the identity of the anti-EGFR adnectin domain in each molecule as follows: EGFR #1 (open up-triangle Δ), EGFR #2 (closed up-triangle ▲), EGFR #3 (open square □), EGFR #4 (closed square ■), EGFR #5 (closed circle ●), EGFR #6 (closed down triangle ▼), EGFR #7 (open circle ○). IGF1R #1 is indicated by (cross x) in FIG. 3A). FIG. 3D) Correlation between ASm values for anti EGFR monoadnectins and EI-tandems (closed triangles ▲ with solid line fit) or with PEGylated EI-tandem adnectins (closed circles with dashed line fit).

FIG. 5A) Assay reproducibility is demonstrated with 3-4 replicate experiments for Adn-Fc-A (open circle ○), Adn-Fc-B (open square □) and Adn-Fc-K (open up-triangle Δ). FIG. 5B) Ammonium sulfate salting out data for 2.1, 1.5, 0.9, 0.45, 0.3, 0.15 and 0.075 mg/ml Adn-Fc-K as detected by A280 or by FIG. 5C) intrinsic fluoresence. FIG. 5D) Logrithmic dependence of ASm values on the protein concentration tested, as demonstrated for Adn-Fc-K (closed circle ●), dAb3-1-IgG1* (open up-triangle Δ) and dAb5-4-IgG1* (open square □).

FIG. 6A) Change in high molecular weight species (% HMW) over time for 1 mg/ml Adn-Fc molecules following exposure to 30-37° C. thermal stress, as measured by SEC. FIG. 6B) % HMW for Adn-Fc molecules at elevated protein concentrations as determined by SEC. FIG. 6C) Example salting out data for Adn-Fc proteins. Symbols in panels A-C are as follows: Adn-Fc-a (open star ☆), Adn-Fc-A (closed star ★), Adn-Fc-B (open circle ○), Adn-Fc-b (closed circle ●), Adn-Fc-C (open square □), Adn-Fc-D (closed square ■), Adn-Fc-E (closed diamond ♦), Adn-Fc-F (cross x), Adn-Fc-G (plus +), Adn-Fc-H (open down triangle ▽), Adn-Fc-I (open up triangle Δ), Adn-Fc-J (closed up triangle ▲), Adn-Fc-K (closed down triangle ▼), Adn-Fc-L (open diamond ◇). FIG. 6D) ASm values for Adn-Fc molecules, sorted from left to right by increasing ASm value at 0.45 mg/ml [protein]. Error bars represent the standard deviation of 3-4 independent experiments.

FIG. 7A) Example salting out data for dAb-Fc proteins. FIG. 7B) Concentration-dependence of Rh for selected dAb-Fcs as measured by DLS. The symbols in panels A and B are as follows: dAb2-2-IgG1 (open down-triangle ▽), dAb2-3-IgG1 (closed circle ●), dAb3-1-IgG1* (open up-triangle Δ), dAb5-4-IgG1*-CHO (closed down-triangle ▼), dAb6-2-IgG1* (closed up-triangle ▲), dAb8-1-IgG1* (closed diamond ♦), dAb8-3-IgG1* (open circle ○), dAb8-2-IgG4 (closed square ■), dAb9-1-IgG1* (open square □). Error bars in FIG. 7B represent the standard deviation of 3-4 measurements. FIG. 7C) Overlay of ASm values (closed up-triangle ▲) and hydrodynamic radius values (○) for all dAb-Fc molecules tested.

FIG. 11A) Solubility of wild type and mutant EGFR #8 proteins in 2.0 M AS (light grey bars) or 2.2 M AS (dark grey bars). Data for wild type EGFR #8 represent the average with standard deviation error bars from three independent measurements. FIG. 11B) Spatial-aggregation-propensity (SAP) values for all EGFR #8 adnectin mutants, at R=5 Å (light grey bars) and R=10 Å (dark grey bars).

FIGS. 12A-12D. Comparison of antibody, VH fragment, and Adnectin showing relative size of the molecules. Cartoon diagrams of (FIG. 12A) IgG1 (PDB ID 1IGT), (FIG. 12B) VHH (1F2X) with the CDRs marked 1, 2, 3, (FIG. 12C) an Adnectin, with the diversified loops marked BC, DE, and FG, and (FIG. 12D) superposition of an Adnectin and VHH showing that the positions of BC, DE, and FG loops are similar to those CDRs 1, 2, and 3.

FIGS. 13A-13E. Binding of Adnectin 1 to EGFR. (FIG. 13A) The EGFR is represented as a gray surface and shown bound to Adnectin 1 on domain I and the Fv portion of cetuximab on domain III (PDB 1YY9; Li et al., 2005). Adnectin and cetuximab are shown as cartoons with β-strands (red), and non-repetitive secondary structure (cyan). (FIG. 13B) Residues of Adnectin 1 involved in contacts with EGFR. The Adnectin backbone is shown as a cartoon with the following color scheme: β-strands (red), non-repetitive secondary structure (orange), and diversified loops (magenta). Residues involved in contacts from the diversified loops are shown with magenta carbon atoms. Residues involved in contacts from the remainder of the Adnectin are shown with black carbon atoms and black regions on the secondary structure cartoon. Note the sequential stretch in the D strand that contacts EGFR. (FIG. 13C) Interaction between Adnectin and EGFR domain I. Adnectin is in magenta and EGFR cartoon is in cyan. The interacting surface on EGFR shows the stricter definition of contacting residues in orange and the relaxed definition of buried residues in yellow. (FIG. 13D) Overlap of Adnectin 1 and EGF contacting surfaces on EGFR domain I are shown. Adnectin 1 (cyan) and EGF (orange) are represented as cartoons. The unique contacting surfaces and overlapping surface are shown as Adnectin 1 (yellow), EGF (red), and for both (magenta). (FIG. 13E). β-strand-like interactions between EGFR residue 15-18 and Adnectin 1 residues 76-79 with N . . . O═C hydrogen bonds formed between Q16 N and D77 O, K79 N and Q16 O, and L17 N and K79 O, and a side-chain hydrogen bond between T16 OG1 and D77 OD1.

(FIG. 14A) The IL-23 is represented as a gray surface and shown bound to Adnectin 2 at the interface between the p40 and p19 subunits and the Fv portion of 7G10 is shown bound to p19 subunit (PDB 3D85; Beyer et al., 2008). Adnectin and 7G10 are shown as cartoons with the same color coding as FIG. 2A. (FIG. 14B) Adnectin 2 residues involved in contacts with IL-23. Adnectins 1 (FIG. 2B) and 2 are oriented identically to allow comparison of the differing shapes by inspection. Color coding the same as in FIG. 2B. In Adnectin 2 the following regions make contact with IL-23: the N-terminal region, the C strand, the CD loop, the E strand and the F strand. (FIG. 14C) Interaction between Adnectin and IL-23 with the color coding of the surface and the Adnectin the same as FIG. 2C. The p40 domain (chain A) is shown in a lighter cyan and the p19 domain (chain B) is shown in a darker cyan. (FIG. 14D) A view of the Adnectin 2/IL-23 interaction involving only the diversified loops and N-terminal region. Same color coding as part (FIG. 14C). (FIG. 14E) A view showing only residues 76-85 of the FG loop of Adnectin 2 bound to IL-23.

(FIG. 15A) Amino 25 acid sequences of the two Adnectins vs. the parent $^{10}$Fn3 domain. The parts of BC, DE, and FG loops that were diversified are underlined in the figure, encompassing residues 23-29, 52-55, and 77-86, respectively. (FIG. 15B, FIG. 15C) Two orthogonal views superimposed on PDB 1FNF residues 1416 to 1509. Color code: 1FNF (blue), Adnectin 1 (red), and Adnectin 2 (cyan). Note the excellent superposition of the core β-strands and the AB and EF loops. The DE loop, which is quite short, shows little variation in these structures. The BC loop shows modest variation. In contrast, the FG loop shows dramatic variation in position even between the equal-length Adnectin 2 and $^{10}$Fn3 loops. In Adnectin 1, the F and G β-strands extend farther into the diversified region; however, to highlight the diversified region those residues were drawn as non-repetitive secondary structure. Although the N-termini of the $^{10}$Fn3 and Adnectin 1 are similar, that of Adnectin 2 differs considerably.

FIG. 17A. Interaction between Adnectin 1 and EGFR domain I. Cartoons of Adnectin is in magenta and EGFR is in cyan. The interacting surface on EGFR shows contacting residues in orange and buried residues in yellow. FIG. 17B. Overlap of Adnectin 1 and EGF contacting surfaces on EGFR domain I are shown. Adnectin 1 (cyan) and EGF (blue) are represented as cartoons. The contacting surfaces are shown Adnectin 1 (yellow), EGF (red), and the overlapping surface (magenta).

FIGS. 18A and 18B are rotated 90° in z from their representation in FIG. 14 to accommodate an interocular distance of ~60 mm for stereo viewing. FIG. 18A. Interaction between Adnectin and IL-23. The Adnectin is shown as a cartoon (magenta). The cartoons of the p40 domain (chain A) is shown in a lighter cyan and the p19 domain (chain B) is shown in a darker cyan. The interacting surface on IL-23 shows contacting residues in orange and buried residues in yellow. FIG. 18B. A view of the Adnectin 2/IL-23 interaction involving only the diversified loops and N-terminal region. Same color coding as FIG. 18A. FIG. 18C. A view of the Adnectin 2/IL-23 interaction involving only the FG loop. Same color coding as FIG. 18A.

FIG. 19A. Stereo view of superposition of the $^{10}$Fn3-based domains of 2OCF (orange), 3CSB (pink), 3CSG (raspberry), 3K2M (chain C) (green), 3QHT (chain B) (slate), 3QWQ (red), and 3QWR (cyan) on domain 10 1FNF (blue). This view is rotated 90° in z compared to FIG. 15B to accommodate an interocular distance of ~60 mm. FIG. 19B. Stereo view of superposition of the $^{10}$Fn3-based domains of 2OCF (orange), 3CSB (pink), 3CSG (raspberry), 3K2M (chain C) (green), 3QHT (chain B) (slate), 3QWQ (red), and 3QWR (cyan) on domain 10 1FNF (blue). This view is the same orientation as FIG. 15C, but compared to the A (above) rotated 90° in z and then 90° in y. These figures emphasize that the core of the $^{10}$Fn3-based domains is maintained, but diversified loops can vary in conformation to accommodate binding to target.

FIG. 20A) SEC chromatograms for EGFR #8 (75 ug load), EGFR #8-T58E (73 ug load) and EGFR #8-T58D (52 ug load). FIG. 20B) DSC thermogram data for 1 mg/ml samples of EGFR #8 Adnectins in PBS pH 7.1. FIG. 20C) Fit DSC data for EGFR #8. FIG. 20D) Fit DSC data for EGFR #8-T58E. FIG. 20E) Fit DSC data for EGFR #8-T58D.

FIG. 21. Ammonium sulfate salting out curves for EGFR #8 proteins tested at 0.33 mg/ml. Symbols represent the data for wild type EGFR #8, $AS_m$=2.08 M (open circle ○), EGFR #8-T58E, $AS_m$=2.15 M (open square □), and EGFR #8-T58D, $AS_m$=2.16 M (open up-triangle △).

FIGS. 22A and 22B. Aggregation propensity of EGFR #8 Adnectins. FIG. 22A) Relationship between measured protein concentration versus expected protein concentration (based on visual volume estimates) for Adnectins concentrated at small scale using ultrafiltration. FIG. 22B) Percentage of high molecular weight (% HMW) species in the soluble fraction of the concentrated Adnectin samples as measured by SEC.

FIGS. 23A-23C. Accelerated stability data for EGFR #8 Adnectins in PBS pH 7.1. FIG. 23A) Adnectin protein concentration at time zero (t0) and after 1 week (1w) or 2 weeks (2w) at 40° C. as measured by $A_{280}$. FIG. 23B) Changes in soluble protein concentration as measured by integration of SEC peaks. FIG. 23C) Percentage of high molecular weight (% HMW) species in the soluble fraction as measured by SEC after 1 week (1w) or 2 weeks (2w) at 40° C.

FIG. 24. Amino acid sequence alignment of EGFR #4 (SEQ ID NO. 81) and EGFR #8 (SEQ ID NO. 82) with the "BC", "DE" and "FG" target binding loop sequences indicated. The consensus sequence corresponds to SEQ ID NO. 87.

FIG. 23A) SEC chromatograms for EGFR #4 (50 ug load) or EGFR #4-T58E (50 ug load). FIG. 23B) DSC thermogram data for 1 mg/ml samples of EGFR #4 Adnectins in PBS pH 7.1. FIG. 23C) Fit DSC data for EGFR #4. FIG. 23D) Fit DSC data for EGFR #4-T58E.

FIG. 26. Ammonium sulfate salting out curves for EGFR #4 Adnectins tested at 0.3 mg/ml. Symbols represent the data for wild type EGFR #4, $AS_m$=0.865±0.014 M (open circle ○), EGFR #4-T58E, ASm=1.024±0.003 (open square □).

FIGS. 27A and 27B. Aggregation propensity of EGFR #4 Adnectins. FIG. 27A) Relationship between measured protein concentration versus expected protein concentration (based on visual volume estimates) for Adnectins concentrated at small scale using ultrafiltration. FIG. 27B) Percentage of high molecular weight (% HMW) species in the soluble fraction of the concentrated Adnectin samples incubated overnight at room temperature as measured by SEC.

DETAILED DESCRIPTION

Definitions

Figure 3A:
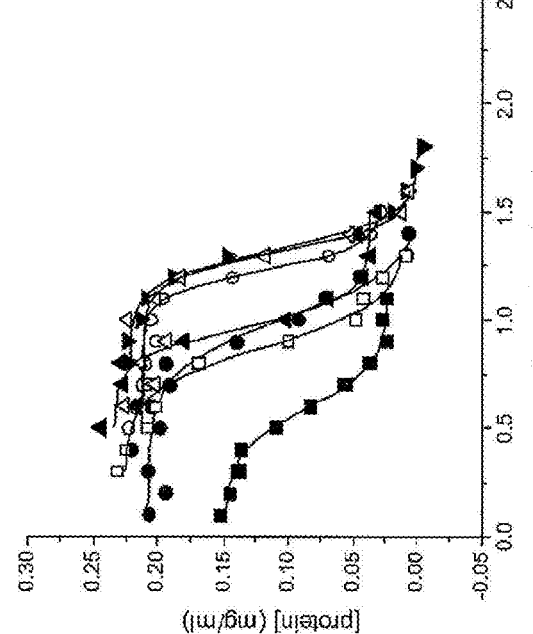
FIGS. 3A-3D show ammonium sulfate salting out data for adnectins.

The term "polypeptide" refers to any sequence of two or more amino acids, regardless of length, post-translation modification, or function. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

As used herein, a "fibronectin based scaffold" or "FBS" protein or moiety refers to proteins or moieties that are based on a domain in fibronectin, e.g., fibronectin type III ("Fn3") repeat. A protein or a domain (of a protein) that is based on an Fn3 repeat is referred to herein as "Fn3 protein," "Fn3 domain protein" or "Fn3 domain." Fn3 is a small (about 10 kDa) domain that has the structure of an immunoglobulin (Ig) fold (i.e., an Ig-like β-sandwich structure, consisting of seven β-strands and six loops). Fibronectin has 18 Fn3 repeats, and while the sequence homology between the repeats is low, they all share a high similarity in tertiary structure. Fn3 domains are also present in many proteins other than fibronectin, such as adhesion molecules, cell surface molecules, e.g., cytokine receptors, and carbohydrate binding domains. The term "fibronectin based scaffold" protein or moiety or "Fn3 protein" or "Fn3 domain" or "Fn3 domain protein" is intended to include proteins or domains based on Fn3 domains from these other (i.e., non fibronectin) proteins. Exemplary Fn3 domains include the $7^{th}$, $10^{th}$ and $14^{th}$ fibronectin type III domain, which are referred to herein as $^7$Fn3, $^{10}$Fn3 and $^{14}$Fn3, respectively. As used herein, a "Fn3 domain" or "Fn3 moiety" or "Fn3 domain protein" refers to wildtype Fn3 (e.g., SEQ ID NOs: 1-8, 10, 12, 14 or 16, 65 or 66) and biologically active variants thereof, e.g., biologically active variants that may specifically bind to a target, such as EGFR, IL23 and IGF1R. For example, $^{10}$Fn3 molecules binding to specific targets may be selected from $^{10}$Fn3 libraries using the PROfusion technique, which is described, e.g., in WO02/32925. A wild type $^{10}$Fn3 domain may comprise one of the amino acid sequences set forth in SEQ ID NOs: 1-8, 10, 12, 14, 16. The amino acid sequence of wildtype human $^{10}$Fn3 is set forth in SEQ ID NO: 1. A wild type $^7$Fn3 domain may comprise the amino acid sequence set forth in SEQ ID NO: 65. A wild type $^{14}$Fn3 domain may comprise the amino acid sequence set forth in SEQ ID NO: 66. Biologically active variants of a Fn3 domain include Fn3 domains that comprise at least, at most or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid variations, i.e., substitutions, additions or deletions, relative to a Fn3 domain comprising an amino acid sequence selected from SEQ ID NOs:1-16, and 65-71. A biologically active variant of a Fn3 domain may also comprise, or comprise at most, 1-3, 1-5, 1-10, 1-15, 1-20, 1-25, 1-30, or 1-40 amino acid changes relative to a Fn3 domain comprising an amino acid sequence selected from SEQ ID NOs:1-16, and 65-71. In certain embodiments, a biologically active variant of a Fn3 domain does not comprise more than 1, 2, 3, 4, 5, 6, 7, 8, 9, 10, 11, 1,2, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid variations, i.e., substitutions, additions or deletions, relative to an Fn3 domain comprising an amino acid sequence selected from SEQ ID NOs:1-16, and 65-71. An amino acid change(s) may be in a loop region and/or in a non-loop region, e.g., a β-strand. Exemplary degenerate $^{10}$Fn3 amino acid sequences are provided herein as SEQ ID NOs: 17-29.

The phrase "comprising an amino acid sequence based on" a specific or first sequence is intended to include amino acid sequences that are derived from the specific or first amino acid sequence, e.g., by amino acid substitutions, additions or deletions. For example, a protein comprising an amino acid sequence based on an amino acid sequence selected from SEQ ID NOs:1-29 and 65-66 refers to a protein comprising an amino acid sequence that is derived from any of SEQ ID NOs: 1-29 and 65-66, including, e.g., a protein comprising an amino acid sequence that differs from one or more of SEQ ID NOs: 1-29 and 65-66 in one or more loop or non-loop sequences, such as to obtain binding to a desired target.

A "region" of a Fn3 domain (or moiety) as used herein refers to either a loop (AB, BC, CD, DE, EF and FG), a β-strand (A, B, C, D, E, F and G), the N-terminus (e.g. amino acid residues 1-7 of SEQ ID NO: 1 or 6), or the C-terminus (e.g. amino acid residues 93-101 of SEQ ID NO: 1 or amino acid residues 93-95 of SEQ ID NO: 6) of a Fn3 domain.

An Fn3 domain may comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole"). Any or all of loops AB, BC, CD, DE, EF and FG may participate in or contribute to ligand binding.

The term "non-loop region" of a Fn3 domain refers to a β-strand, the N-terminus, or the C-terminus of a Fn3 domain. A non-loop region of a Fn3 domain may also be referred to as a "scaffold region."

A "north pole loop" refers to any one of the BC, DE and FG loops of a Fn3 domain.

A "south pole loop" refers to any one of the AB, CD and EF loops of a Fn3 domain.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by a sequence alignment program, such as BLAST, BLAST-2, ALIGN, ALIGN-2 or Megalign (DNASTAR), in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

As used herein, an amino acid residue in a polypeptide is considered to "contribute to binding" a target if (1) any of the non-hydrogen atoms of the residue's side chain or main chain is found to be within five angstroms of any atom of the binding target based on an experimentally determined three-dimensional structure of the complex, and/or (2) mutation of the residue to its equivalent in wildtype Fn3 (e.g., SEQ ID NO: 1), to alanine, or to a residue having a similarly sized or smaller side chain than the residue in question, leads to a measured increase of the equilibrium dissociation constant to the target (e.g., an increase in the $k_{on}$).

As used herein, "Fc" encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination. The term "Fc moiety" or "Fc domain" as used herein refers to any of the combination of CH1, hinge, CH2, CH3 and CH4 domains. Thus, an "Fc domain" or moiety may or may not comprise a hinge.

"Moiety" refers to a portion of a protein. For example, a fusion protein may comprise several moieties. In one embodiment, a fusion protein comprises a fibronectin (Fn) based scaffold moiety and an Fc moiety.

The term "enhanced solubility" may mean higher proportion (e.g. concentration, molality, mole fraction, or mole ratio) of a protein solute in a designated solvent, under saturated solution conditions, as compared to another protein. This may also be expressed as higher solubility limit of a protein. "Enhanced solubility" may also mean decreased protein aggregation, or lower proportion (e.g. percentage, fraction, or ratio) of aggregated protein species at a given protein concentration in a designated solvent, as compared to another protein. This may be alternatively expressed as decreased aggregation propensity of a protein. The term "aggregation" may refer to interaction or association between two or more protein molecules, for example, proteins in their native conformation or misfolded protein molecules. The interacting or associating molecules may be referred to as, for example, an "aggregate", "oligomer" (such as, dimer, trimer, tetramer, or higher order oligomers), "high molecular weight species", "higher order species", or other related terms which are commonly understood by one of ordinary skill in the art. The solubility of a protein may be analyzed by any suitable techniques. In some embodiments, the solubility of a protein may be analyzed by ammonium sulfate solubility assay. In some embodiments, the solubility of a protein may be analyzed by ultrafiltration. In some embodiments, the solubility of a protein may be analyzed under accelerated stress conditions.

In some embodiments, the solubility of a protein may be regarded as enhanced if the solubility of a protein in a solvent is enhanced by at least 1%, 2%, 5%, 10%, 15%, 20%, 30%, or 50% or more as compared to the solubility of another protein in the solvent. In some embodiments, the solubility of a protein may be regarded as enhanced if the solubility limit of a protein in a solvent is at least 0.01 mg/ml, 0.1 mg/ml, 0.5 mg/ml, 1 mg/ml, 2 mg/ml, 5 mg/ml, 10 mg/ml, 20 mg/ml, 50 mg/ml, 100 mg/ml, 200 mg/ml, or 500 mg/ml higher than the solubility limit of another protein in the solvent. In some embodiments, the solubility of a protein may be regarded as enhanced if the percentage of aggregated protein species at a given concentration is lower by at least 0.5%, 1%, 2%, 5%, 10%, 20%, 50% or more as compared to the percentage of aggregated protein species of another protein at the concentration.

Overview of Protein Solubility and Assays

Protein aggregation is a complex process that may originate by several different mechanisms (Morris, A. M. et al., 2009, Biochim Biophys Acta. 1794, 375-97; Joubert, M. K. et al., 2011, J Biol Chem 286, 25118-33; Weiss, W. F. et al., 2009, J Pharm Sci. 98, 1246-77; Roberts, C. J. 2007, Biotechnol Bioeng. 98, 927-38; Hawe, A. et al., 2009, Eur J Pharm Sci. 38, 79-87; Mahler, H. C. et al., 2009, J Pharm Sci. 98, 2909-34; Philo, J. S. and Arakawa, T., 2009, Curr Pharm Biotechnol. 10, 348-51). Aggregates may form, for example, due to self-association of the native conformation, or structurally altered states such as a molten globule, denatured, degraded, or chemically modified structures. Protein aggregation or solubility may also be influenced by solution conditions, the presence of contaminants, as well as a variety of external factors such as temperature, mechanical stress, or freeze/thaw stress. Moreover, the types of aggregate may be covalent or non-covalent, and may differ in morphology ranging from soluble dimers or higher order oligomers, to insoluble amorphous precipitates, or more regular amyloid structures.

A number of techniques may be used to analyze protein solubility and to detect aggregates of different sizes and morphologies, as well as to characterize the mechanisms of aggregation (Wang, W. 2005, Int J Pharm 289, 1-30; Singh, S. K. et al., 2010, J Pharm Sci. 99, 3302-21; Kamerzell, T. J. et al., 2011, Adv Drug Deliv Rev. 63, 1118-59; Zolls, S. et al., 2012, J Pharm Sci. 101, 914-35). Techniques based on the principles of light scattering, spectroscopy, electrophoresis, chromatography and many others may be used to characterize protein aggregation, stability and solubility, or to compare the aggregation propensity or solubility of different protein molecules to each other, or one molecule under different solution conditions. The proteins may be concentrated prior to analysis using methods such as ultrafiltration or lyophilization. Or smaller scale methods may be used to concentrate proteins for solubility and aggregation analysis, including the use of osmotic-pressure, freeze/thaw, and solvent evaporation (Shire, S. J. et al., 2004, J Pharm Sci. 93, 1390-402). Aggregation may also be studied at lower protein concentrations under accelerated stress conditions such as elevated temperature, shear or mixing stress (Hawe, A. et al., 2012, J Pharm Sci. 101, 895-913), using high throughput fluorescent dye binding assays (Kayser, V. et al., 2012, Biotechnol J. 7, 127-32; He, F. et al., 2010, J Pharm Sci. 99, 1707-20), or even predicted using in silico methods (Caflisch, A., 2006, Curr Opin Chem Biol. 10, 437-44; Fernandez-Escamilla, A. M. et al., 2004, Nat Biotechnol. 22, 1302-6; Cellmer, T. et al., 2007, Trends Biotechnol. 25, 254-61).

Protein aggregation propensity may also be analyzed based on their relative solubility in the presence of one or more kosmotropic agents, for example, ammonium sulfate (AS) or other kosmotropes such as phosphate ($PO_4^3$), or fluoride (F), or in the presence of volume excluding polymers such as polyethylene glycol (PEG). The mechanism of AS-induced protein precipitation or "salting out", may involve the strong binding of water molecules by the polar kosmotropic sulfate anion, which dehydrates the protein surfaces, increases the chemical potential of the protein and causes the protein molecules to aggregate into an amorphous precipitate (Baldwin, R L., 1996, Biophys J. 71, 2056-63). Because the hydrophobic surfaces on the protein are preferentially dehydrated over the polar surfaces, AS-induced protein self-association may be driven by the interaction of exposed hydrophobic surfaces, similar to the forces that drive aggregation in the absence of AS (Young, L. et al., 1994, Protein Sci. 3, 717-29; Arunachalam, J. and Gautham, N., 2008, Proteins. 71, 2012-25; Fink, A. L., 1998, Fold Des. 3, R9-23). The theory of relative protein solubility determination using AS is reviewed by Trevino et al (2008, J Pharm Sci. 97, 4155-66), who also described its application in the relative solubility determination of a series of RNAse variants (Trevino, S. R. et al., 2007, J Mol Biol. 366, 449-60). A manual bench scale method as well as a titration-based automated method around this concept are described herein and may be used to determine relative protein solubility.

Modified Fibronectin Type III (Fn3) Domains with Enhanced Solubility

Provided herein are polypeptides comprising a modified Fn3 domain, wherein the modified Fn3 domain comprises an amino acid modification that enhances the solubility of the polypeptide relative to a polypeptide (or Fn3 domain) that does not comprise the amino acid modification. The amino acid modification may be in a loop, or a β-strand, e.g., β-strand E, of the Fn3 domain. Provided herein are, e.g., polypeptides comprising a modified Fn3 domain, wherein the modified Fn3 domain comprises an amino acid sequence wherein the amino acid corresponding to residue selected 58 of SEQ ID NO: 1 is mutated, and wherein the solubility of the modified Fn3 domain is enhanced relative to the solubility of a Fn3 domain wherein the amino acid corresponding to residue 58 of SEQ ID NO: 1 is not mutated.

SEQ ID NO: 1 is the sequence of the wildtype human $^{10}$Fn3 domain set forth in:

(SEQ ID NO: 1)
VSDVPRDLEVVAA<u>TPTSLLISW</u>DAPAVTVRYYRITY<u>GETGGNSPVQEFT</u>

VPGSKSTATISGL<u>KPGVD</u>YTITVYA<u>VTGRGDSPASSKP</u>ISINY*RTEIDK*

*PSQ*

(the AB, CD and EF loops are underlined; the BC, DE, and FG loops are emphasized in bold; the β-strands are located between each of the loop regions; and the N-terminal and C-terminal regions are shown in italics). In SEQ ID NO:1, the AB loop refers to residues 14-17, the BC loop refers to residues 23-31, the CD loop refers to residues 37-47, the DE loop refers to residues 51-56, the EF loop refers to residues 63-67, and the FG loop refers to residues 75-87. The BC, DE and FG loops align along one face of the molecule, i.e. the "north pole", and the AB, CD and EF loops align along the opposite face of the molecule, i.e. the "south pole". In SEQ ID NO: 1, β-strand A refers to residues 8-13, β-strand B refers to residues 18-22, β-strand C refers to residues 32-36, beta strand D refers to residues 48-50, β-strand E refers to residues 57-62, β-strand F refers to residues 68-74, and β-strand G refers to residues 88-92. The β-strands are connected to each other through the corresponding loop, e.g., strands A and B are connected via loop AB in the formation β-strand A, loop AB, β-strand B, etc. The N-terminal and/or C-terminal regions of SEQ ID NO: 1 (italicized above), may be removed or altered to generate a molecule retaining biological activity or to introduce target-binding activity.

Binders Having a North Pole and South Pole Loop Modified

In some embodiments, the polypeptides comprising a solubility enhancing mutation, e.g., a T58 mutation, comprise a Fn3, e.g., $^{10}$Fn3 domain having (i) a modification in the amino acid sequence of at least one north pole loop selected from the BC, DE and FG loops relative to the corresponding loop of the wildtype human Fn3 domain, e.g., $^{10}$Fn3 domain (SEQ ID NO: 1 or 5), and (ii) a modification in the amino acid sequence of at least one south pole loop selected from the AB, CD and EF loops relative to the corresponding loop of the wildtype human Fn3 domain, e.g., $^{10}$Fn3 domain (SEQ ID NO: 1 or 5). The modified north pole and south pole loops may contribute to binding to the same target. Various combinations of modified north pole and south pole loops are contemplated. For example, a Fn3, e.g., $^{10}$Fn3 may comprise one modified north pole loop and one modified south pole, one modified north pole loop and two modified south pole loops, two modified north pole loops and one modified south pole loop, two modified north pole loops and two modified south pole loops, three modified north pole loops and one modified south pool loop, etc., wherein each of the modified loops contributes to binding to the same target. Exemplary combinations of north pole and south pole loops that may be modified include, for example, the CD loop (south pole) and the FG loop (north pole), the CD loop (south pole) and the DE loop (north pole), the EF loop (south pole) and FG loop (north pole), the AB loop (south pole) and the FG loop (north pole), or the DE loop (north pole) and the EF loop (south pole). Another exemplary loop combination is the CD loop (south pole), the DE loop (north pole) and the EF loop (south pole). Yet another exemplary loop combination is the DE loop (north pole) and one of more of the AB, CD and EF loops (south pole). The modified loops may have sequence modifications across an entire loop or only in a portion of the loop. Additionally, one or more of the modified loops may have insertions or deletions such that the length of the loop is varied relative to the length of the corresponding loop of the wildtype sequence. In certain embodiments, additional regions in the Fn3 domain (i.e., in addition to the north and south pole loops), such as β-strand, N-terminal and/or C-terminal regions, may also be modified in sequence relative to the wildtype Fn3 domain, and such additional modifications may also contribute to binding to the target.

In certain embodiments, the fibronectin based scaffold moiety comprises a $^{10}$Fn3 domain that is defined generally by following the sequence:

(SEQ ID NO: 17)
VSDVPRD<u>LEVVAA</u>(X)$_u$<u>LLISW</u>(X)$_v$<u>YRITY</u>(X)$_w$FTV(X)$_x$<u>ATISGL</u>
(X)$_y$<u>YTITVYA</u>(X)$_z$<u>ISINYRT</u>, or by the sequence having SEQ ID NO: 18-29. In SEQ ID NOs: 17-29, the AB loop is represented by (X)$_u$, the BC loop is represented by (X)$_v$, the CD loop is represented by (X)$_w$, the DE loop is represented by (X)$_x$, the EF loop is represented by (X)$_y$, and the FG loop is represented by X$_z$. X represents, independently, any amino acid and the subscript following the X represents an integer of the number of amino acids. For example, u, v, w, x, y and z may each be an integer selected, independently, from 2-20, 2-15, 2-10, 2-8, 5-20, 5-15, 5-10, 5-8, 6-20, 6-15, 6-10, 6-8, 2-7, 5-7, and 6-7. The sequences of the beta strands (underlined) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NOs: 17-29. In some embodiments, the sequences of the beta strands may have anywhere from 0 to 10, from 0 to 8, from 0 to 6, from 0 to 5, from 0 to 4, from 0 to 3, from 0 to 2, or from 0 to 1 substitutions, e.g., conservative substitutions, across all 7 scaffold regions relative to the corresponding amino acids shown in SEQ ID NO: 17-29. In certain embodiments, the hydrophobic core amino acid residues (bolded residues in SEQ ID NO: 17 above) are fixed, and any substitutions, conservative substitutions, deletions or additions occur at residues other than the hydrophobic core amino acid residues. In some embodiments, the hydrophobic core residues of the polypeptides provided herein have not been modified relative to the wildtype human $^{10}$Fn3 domain (e.g., SEQ ID NO: 1).

In some embodiments, the amino acid sequence of the modified Fn3 domain may be at least 40%, 50%, 60%, 65%, 70%, 75%, 80%, 85%, 90%, 95%, 97%, 98%, or 99% identical to that of a wildtype Fn3 domain, for example, a human Fn3 domain of SEQ ID NO:1-16, 65, or 66. In some embodiments, the amino acid sequence of the modified Fn3 domain may be at least 50% identical to that of a wildtype Fn3 domain. In some embodiments, the amino acid sequence of the modified Fn3 domain may be at least 65% identical to that of a wildtype Fn3 domain. In some embodiments, the amino acid sequence of the modified Fn3 domain may be at least 80% identical to that of a wildtype Fn3 domain. In some embodiments, the amino acid sequence of the modified Fn3 domain may be at least 90% identical to that of a wildtype Fn3 domain. In certain embodiments, one or more of the loops will not be modified relative to the sequence of the corresponding loop of the wildtype sequence and/or one or more of the β-strands will not be modified relative to the sequence of the corresponding β-strand of the wildtype sequence. In certain embodiments, each of the beta or beta-like strands of a $^{10}$Fn3 domain in a Fn3 moiety may comprise, consist essentially of, or consist of an amino acid sequence that is at least 80%, 85%, 90%, 95% or 100% identical to the sequence of a corresponding beta or beta-like strand of SEQ ID NO: 1. In some embodiments, variations in the β-strand regions may not disrupt the stability of the polypeptide in physiological conditions.

In some embodiments, the non-loop region of the Fn3, e.g., $^{10}$Fn3, domain may be modified by one or more conservative substitutions. As many as 3%, 5%, 10%, 20% or even 30% or more of the amino acids in the Fn3, e.g., $_{10}$Fn3, domain may be altered by a conservative substitution without substantially altering the affinity of the $^{10}$Fn3 for a ligand. In certain embodiments, the non-loop regions, e.g., the β-strands may comprise anywhere from 0-15, 0-10, 0-8, 0-6, 0-5, 0-4, 0-3, 1-15, 1-10, 1-8, 1-6, 1-5, 1-4, 1-3, 2-15, 2-10, 2-8, 2-6, 2-5, 2-4, 5-15, or 5-10 conservative amino acid substitutions. In exemplary embodiments, the scaffold modification may reduce the binding affinity of the Fn3, e.g., $^{10}$Fn3, binder for a ligand by less than 100-fold, 50-fold, 25-fold, 10-fold, 5-fold, or 2-fold. It may be that such changes may alter the immunogenicity of the Fn3 in vivo, and where the immunogenicity is decreased, such changes may be desirable. As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Exemplary conservative substitutions include those fulfilling the criteria defined for an accepted point mutation in Dayhoff et al., Atlas of Protein Sequence and Structure 5:345-352 (1978 & Supp.). Examples of conservative substitutions include substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

In some embodiments, the amino acid sequence of the modified Fn3 domain may differ from a wildtype Fn3, e.g., $^{10}$Fn3, domain in at most 50, 45, 40, 35, 30, 25, 20, 15, 10 or 5 amino acids. In some embodiments, the amino acid sequence of the modified Fn3 domain may differ from a wildtype Fn3 domain in at most 30 amino acids. In some embodiments, the amino acid sequence of the modified Fn3 domain may differ from a wildtype Fn3 domain in at most 20 amino acids. In some embodiments, the amino acid sequence of the modified Fn3 domain may differ from a wildtype Fn3 domain in at most 10 amino acids.

In some embodiments, the modified Fn3 domain may comprise at least one amino acid variation selected from a substitution, deletion and addition in at least one loop as compared to a wildtype Fn3 domain, for example, a human $^{10}$Fn3 domain of SEQ ID NO:1-16, 65, or 66. In some embodiments, the modified Fn3 domain may comprise at least one amino acid variation in each of at least two loops as compared to a wildtype Fn3 domain. In some embodiments, the modified Fn3 domain may comprise at least one amino acid variation in each of at least three loops as compared to a wildtype Fn3 domain. In some embodiments, the modified Fn3 domain may comprise at least one amino acid variation in at least one loop selected from north pole loops (BC, DE and FG loops), as compared to a wildtype Fn3 domain. In some embodiments, the modified Fn3 domain may comprise at least one amino acid variation in at least one loop selected from south pole loops (AB, CD and EF loops), as compared to a wildtype Fn3 domain. In some embodiments, the modified Fn3 domain may comprise at least one amino acid variation selected from substitution, deletion and addition, in at least one non-loop region and at least one loop, as compared to a wildtype Fn3 domain. In some embodiments, the modified Fn3 domain may comprise at least one amino acid variation in a β-strand as compared to a wildtype Fn3 domain. In some embodiments, the modified Fn3 domain may comprise at least one amino acid variation in each of at least two β-strands as compared to a wildtype Fn3 domain. In some embodiments, the modified Fn3 domain may comprise at least one amino acid variation in each of at least three β-strands as compared to a wildtype Fn3 domain.

In some embodiments, Fn3 domain comprises a loop, AB; a loop, BC; a loop, CD; a loop, DE; a loop, EF; and a loop, FG; and has at least one loop selected from loop AB, BC, CD, DE, EF and FG with an altered amino acid sequence relative to the sequence of the corresponding loop of the human $^{10}$Fn3 domain of SEQ ID NO: 1-16. In some embodiments, the BC, DE and FG loops are altered. In certain embodiments, the AB, CD and EF loops are altered. In certain embodiments, the FG loop is the only loop that is altered. In other embodiments, the CD and FG loops are both altered, and optionally, no other loops are altered. In certain embodiments, the CD and EF loops are both altered, and optionally, no other loops are altered. In some embodiments, one or more specific scaffold alterations are combined with one or more loop alterations. By "altered" is meant one or more amino acid sequence alterations relative to a template sequence (i.e., the corresponding wildtype human fibronectin domain) and includes amino acid additions, deletions, and substitutions.

In some embodiments, the polypeptides may comprise a modified Fn3 domain wherein the non-loop regions comprise an amino acid sequence that is at least 80, 85, 90, 95, 98, or 100% identical to the non-loop regions of a wildtype Fn3 domain (e.g. a human Fn3 domain of SEQ ID NO:1-16, 65, or 66), wherein at least one loop selected from AB, BC, CD, DE, EF and FG may be altered. For example, in certain embodiments, the AB loop may have up to 4 amino acid substitutions, up to 10 amino acid insertions, up to 3 amino acid deletions, or a combination thereof the BC loop may have up to 10 amino acid substitutions, up to 4 amino acid deletions, up to 10 amino acid insertions, or a combination thereof the CD loop may have up to 6 amino acid substitutions, up to 10 amino acid insertions, up to 4 amino acid deletions, or a combination thereof the DE loop may have up to 6 amino acid substitutions, up to 4 amino acid deletions, up to 13 amino acid insertions, or a combination thereof the EF loop may have up to 5 amino acid substitutions, up to 10 amino acid insertions, up to 3 amino acid deletions, or a combination thereof and/or the FG loop may have up to 12 amino acid substitutions, up to 11 amino acid deletions, up to 25 amino acid insertions, or a combination thereof.

It should be understood that not every residue within a loop or non-loop region needs to be modified in order to achieve a Fn3 binding domain having strong affinity for a desired target. Additionally, insertions and deletions in the loop regions may also be made while still producing high affinity Fn3 binding domains. Accordingly, in some embodiments, one or more loops selected from AB, BC, CD, DE, EF and FG may be extended or shortened in length relative to the corresponding loop a wildtype Fn3. In any given polypeptide, one or more loops may be extended in length, one or more loops may be reduced in length, or combinations thereof. In some embodiments, the length of a given loop may be extended by 2-25, 2-20, 2-15, 2-10, 2-5, 5-25, 5-20, 5-15, 5-10, 10-25, 10-20, or 10-15 amino acids. In some embodiments, the length of a given loop may be reduced by 1-15, 1-12, 1-10, 1-5, 1-3, 1-2, 2-10, or 2-5 amino acids. In particular, the FG loop of $^{10}$Fn3 is 13 residues long, whereas the corresponding loop in antibody heavy chains ranges from 4-28 residues. To optimize antigen binding in polypeptides relying on the FG for target binding, therefore, the length of the FG loop of Fn3 may be altered in length as well as in sequence to obtain the greatest possible flexibility and affinity in target binding.

In some embodiments, the amino acid sequences of the N-terminal and/or C-terminal regions of the modified Fn3 domain may be modified by deletion, substitution or insertion relative to the amino acid sequences of the corresponding regions of a wildtype Fn3 domain (e.g. a human Fn3 domain of SEQ ID NO:1-16, 65, or 66). Additional sequences may also be added to the N- or C-terminus of the modified Fn3 domain. For example, in some embodiments, the N-terminal extension may comprise an amino acid sequence selected from the group consisting of: M, MG, and G. In some embodiments, the amino acid sequence of the C-terminal tail of the modified Fn3 domain may be modified or truncated relative to the amino acid sequence of the C-terminal tail of a wildtype Fn3 domain (e.g., a human Fn3 domain of SEQ ID NO:1-16, 65, or 66). In some embodiments, the amino acid sequence of the N-terminus of the modified Fn3 domain may be modified or truncated relative to the amino acid sequence of the N-terminus of a wildtype Fn3 domain.

In certain embodiments, the amino acid sequence of the first 1, 2, 3, 4, 5, 6, 7, 8 or 9 residues of the modified Fn3 domain may be modified or deleted in the polypeptides provided herein relative to the sequence of the corresponding amino acids in a wildtype Fn3 domain. In some embodiments, the amino acids corresponding to amino acids 1-8 of SEQ ID NO: 1 may be replaced with an alternative N-terminal region having from 1-20, 1-15, 1-10, 1-8, 1-5, 1-4, 1-3, 1-2, or 1 amino acids in length. Exemplary alternative N-terminal regions include M, MG, G, MGVSDVPRDL (SEQ ID NO: 30) and GVSDVPRDL (SEQ ID NO: 31), or N-terminal truncations of any one of SEQ ID NOs: 30 and 31. Other suitable alternative N-terminal regions include, for example, $X_n$SDVPRDL (SEQ ID NO: 32), $X_n$DVPRDL (SEQ ID NO: 33), $X_n$PRDL (SEQ ID NO: 34), $X_n$PRDL (SEQ ID NO: 35), $X_n$RDL (SEQ ID NO: 36), $X_n$DL (SEQ ID NO: 37), or $X_n$L, wherein n=0, 1 amino acids, wherein when n=1, X is Met or Gly, and when n=2, X is Met-Gly. When a Met-Gly sequence is added to the N-terminus of a $^{10}$Fn3 domain, the M may be cleaved off, leaving a G at the N-terminus. In other embodiments, the alternative N-terminal region comprises the amino acid sequence MASTSG (SEQ ID NO: 38).

In certain embodiments, the amino acid sequence corresponding to amino acids 93-101, 94-101, 95-101, 96-101, 97-101, 98-101, 99-101, 100-101, or 101 of SEQ ID NO: 1 may be deleted or modified in the polypeptides provided herein relative to the sequence of the corresponding amino acids in the wildtype human $^{10}$Fn3 domain (SEQ ID NO: 1). In exemplary embodiments, the amino acids corresponding to amino acids 95-101 of SEQ ID NO: 1 may be replaced with an alternative C-terminal region having from 1-20, 1-15, 1-10, 1-8, 1-5, 1-4, 1-3, 1-2, or 1 amino acids in length. Specific examples of alternative C-terminal region sequences include, for example, polypeptides comprising, consisting essentially of, or consisting of, EIEK (SEQ ID NO: 39), EGSGC (SEQ ID NO: 40), EIEKPCQ (SEQ ID NO: 41), EIEKPSQ (SEQ ID NO: 42), EIEKP (SEQ ID NO: 43), EIEKPS (SEQ ID NO: 44), EIEKPC (SEQ ID NO: 45), or HHHHHH (SEQ ID NO: 46). In some embodiments, the alternative C-terminal region comprises EIDK (SEQ ID NO: 47), and in particular embodiments, the alternative C-terminal region is either EIDKPCQ (SEQ ID NO: 48) or EIDKPSQ (SEQ ID NO: 49).

In certain embodiments, the modified Fn3 domain may have both an alternative N-terminal region sequence and an alternative C-terminal region sequence.

In some embodiments, at least one residue of the integrin-binding motif "arginine-glycine-aspartic acid" (RGD) (e.g. amino acids 78-80 of SEQ ID NO:1) may be mutated or deleted so as to disrupt integrin binding. In some embodiments, the FG loop of the polypeptides provided herein does not contain an RGD integrin binding site. In one embodiment, the RGD sequence may be replaced by a polar amino acid-neutral amino acid-acidic amino acid sequence (in the N-terminal to C-terminal direction). In another embodiment, the RGD sequence may be replaced with SGE. In yet another embodiment, the RGD sequence is replaced with RGE (see, e.g., SEQ ID NO: 16). In some embodiments, the polypeptide binds specifically to a target that is not bound by a wildtype Fn3 domain, particularly the wildtype human Fn3 domain having, e.g., SEQ ID NO: 1-16, 65, or 66.

In some embodiments, the polypeptide may bind to a desired target with a $K_d$ of less than 500 nM, 400 nM, 300 nM, 200 nM, 100 nM, 50 nM, 20 nM, 10 nM, 5 nM, 1 nM, 500 pM, 100 pM or less. In some embodiments, the polypeptide binds to a desired target with a $K_d$ between 1 pM and 1 µM, between 100 pM and 500 nM, between 1 nM and 500 nM, or between 1 nM and 100 nM. In some embodiments, the polypeptide binds to a desired target with a $K_d$ of less than 500 nM. In some embodiments, the polypeptide binds to a desired target with a $K_d$ of less than 100 nM.

In some embodiments, a polypeptide may comprise an amino acid sequence that is at least 40%, 50%, 60%, 70%, 75%, 80%, 85%, 90%, 95%, 97%, 98%, or 99% identical to an amino acid sequence selected from the group of sequences consisting of SEQ ID NOs: 1-16, and the polypeptide binds specifically to a target, e.g., with a $K_d$ of less than 1000 nM, 500 nM, 100 nM, 50 nM, 10 nM, 5 nM, 1 nM, 500 pM, 100 pM or less. The polypeptide may comprise amino acid changes (or alterations) in one or more loops and one or more strands.

Binders Having Loop and Scaffold Region Modifications

Also provided herein are Fn3, e.g., $^{10}$Fn-3, domains having a solubility enhancing mutation, e.g., a T58 mutation, and having combinations of loop and scaffold modifications. In particular, the application provides polypeptides comprising a solubility enhancing mutation and a Fn3, e.g., $^{10}$Fn3, domain comprising (i) a modification in the amino acid sequence of at least one of loops AB, BC, CD, DE, EF, or FG, and (ii) a modification in the amino acid sequence of at least one scaffold region (i.e., a modification in at least one β-strand, the N-terminal region, and/or the C-terminal region), wherein the modified loop(s) and modified scaffold region(s) both contribute to binding the same target. In exemplary embodiments, the scaffold region modifications are located adjacent to modifications in a loop region, e.g., if the AB loop is modified, scaffold mutations may tend to be located in β-strand A and/or β-strand B, which are adjacent to the AB loop in the linear sequence of the $^{10}$Fn3 domain. In other embodiments, a cluster of modifications may be found together in loop and scaffold regions that are adjacent to one another in the linear sequence of the Fn3 domain. For example, Fn3 binders having both loop and scaffold modifications, may have clusters of amino acid modifications in the following combinations of loop and scaffold regions that are adjacent to each other in the linear sequence of the Fn3 domain: β-strand/loop/β-strand, loop/β-strand/loop, loop/β-strand/loop/β-strand, terminal region/β-strand/loop, or loop/β-strand/terminal region, etc. For example, Fn3 domains having novel combinations of loop and scaffold modifications may have clusters of modifications such that over a stretch of 20 contiguous amino acids at least 15 of the amino acids are modified relative to wildtype. In other embodiments, at least 17 out of 20, 18 out of 20, 17 out of 25, 20 out of 25, or 25 out of 30 residues in a contiguous stretch are modified relative to the wildtype Fn3 domain sequence over the corresponding stretch of amino acids. In certain embodiments, a given Fn3 domain may have two or three clusters of modifications separated by stretches of unmodified (i.e., wildtype) sequence. For any given region (i.e., a loop, β-strand or terminal region) that is modified, all or only a portion of the region may be modified relative to the wildtype sequence. When a β-strand region is modified, preferably the hydrophobic core residues remain unmodified (i.e., wildtype) and one or more of the non-core residues in the β-strand are modified.

"West-Side" Binders

In some embodiments, the application provides Fn3, e.g., $^{10}$Fn3 domains comprising a solubility enhancing mutation, e.g., a mutation at T58, and having a binding face along the "west-side" of the molecule ("West-side binders" or "WS binders"). WS binders as described herein comprise a Fn3, e.g., $^{10}$Fn3, domain that has a modified CD loop and a modified FG loop, as compared to the corresponding CD and FG loop sequences set forth in SEQ ID NO: 1 or 5. The CD loop and the FG loop both contribute to binding to the same target. In certain embodiments, the WS binders may comprise additional modifications at one or more regions within the Fn3 domain. For example, WS binders may comprise scaffold modifications in one or more of the β-strand regions adjacent to the CD and/or FG loops. In particular, WS binders may comprise sequence modifications in one or more of β-strand C, β-strand D, β-strand F, and/or β-strand G. Exemplary scaffold modifications include modifications at one or more scaffold region positions corresponding to the amino acid positions: 33, 35, 49, 69, 71, 73, 89 and/or 91 of SEQ ID NO: 1 or 5. The WS binders may also comprise modifications in the BC loop, particularly in the C-terminal portion of the BC loop. In one embodiment, the last two residues of the BC loop (i.e., corresponding to amino acids 30 and 31 in the wildtype $^{10}$Fn3 domain) are modified relative to the wildtype sequence. All or a portion of the additional loop and scaffold modifications may contribute to binding to the target in conjunction with the modified CD and FG loops. Preferably, the hydrophobic core residues are not modified relative to the wildtype sequence.

In certain embodiments, a WS binder has a CD loop that is about 3-11, 4-9 or 5 residues long; an FG loop that is about 1-10, e.g., 6 or 5, residues long; a C strand that is about 6-14, 8-11, or 9 residues long; and/or an F strand that is about 9-11 or 10 residues long. Positions 31, 33, 35 and 37-39 of the beta strand C may be altered relative to the wildtype sequence. Positions 32, 34 and 36 of the beta strand C may be hydrophobic residues. Positions 67, 69, 71 and 73 of the beta strand F may be altered relative to the wildtype sequence. Positions 68, 70, and 72 of the beta strand F may be hydrophobic residues. A WS binder may comprise amino acid substitutions at positions 30, 31, 32, 33, 34, 35, 36, 37, 38 and/or 39, such as positions 31, 33, 35, 37, 38 and/or 39, e.g., positions 31 and/or 33, of SEQ ID NO: 1 or 5. A WS binder may comprise amino acid substitutions at positions 44, 45, 46, 47, 48, 49, 50 and/or 51, such as positions 44, 45, 47 and/or 49, of SEQ ID NO: 1 or 5. A WS binder may comprise amino acid substitutions at positions 40, 41, 42, 43, 44 and/or 45 of SEQ ID NO: 1 or 5. A WS binder may comprise amino acid substitutions at positions 67, 68, 69, 70, 71, 72, 73, 74, 75 and/or 76, such as positions 67, 69, 71, 73 and/or 76 or positions 71, 73, 75 and/or 76, of SEQ ID NO: 1 or 5. A WS binder may comprise amino acid substitutions at positions 76, 77, 78, 79, 81, 82, 83, 84, 85 and/or 86, such as positions 84 and/or 85 of SEQ ID NO: 1 or 5. A WS binder may comprise amino acid substitutions at positions 85, 86, 87, 88, 89, 90, 91, 92, 93 and/or 94 of SEQ ID NO: 1 or 5. A WS binder may comprise amino acid substitutions at positions 31, 33, 47, 49, 73 and/or 75 of SEQ ID NO: 1 or 5. A WS binder may comprise a loop C comprising from 4-9 varied, e.g., non wildtype amino acids; an FG loop comprising from 5-6 varied, e.g., non wildtype amino acids; and wherein amino acids 31, 33, 35, 37-39, 67, 69, 71, 73 and 76 are not wildtype. "Not wildtype" amino acids are amino acids that are not those found at the same position in the wildtype human $^{10}$Fn3 molecule (having, e.g., SEQ ID NO: 1 or 5).

Exemplary WS binders include those having a wildtype or mutated amino acid at positions 30, 31, 33, 35, 37, 38, 46, 47, 49, 50, 67, 69, 71, 73, 75, 76, 84, 85, 86, 87, 89 or 91. For example, a WS binder design may comprise one or more amino acid modifications in amino acids 39-45 of the CD loop and one or more amino acid modification in amino acids 77-83 in loop FG (WS-LI1 design), and wherein a $^{10}$Fn3 molecule having that design binds specifically to a target molecule (and optionally does not comprise an RGD sequence). A WS binder design may comprise the design of WS-ill and at most 1, 2, 3, 4, 5, 6, 7, 8, 9, 10, 12, 15, 17, 20 or 25 additional amino acid modifications in the loops or strands. For example, a WS binder design may comprise the design of WS-LI1 and at most 1, 2, 3, 4, 5, 6, 7, 8, 9, 10, 12, 15, 17, 20 or 25 additional amino acid modifications at amino acid positions such as at amino acid positions 37, 38, 46, 47, 75, 76, and 85-88. Other amino acid modifications that may be included are those at positions 30, 31, 33, 35, 49, 50, 67, 69, 71, 73, 89 and 91.

In certain embodiments, at least or at most 10, 20, 30, 40, 50, or 50 amino acids of a design sequence is not varied, e.g., is not varied by substitution. For example, one or more of the following amino acids are retained as the amino acid from the wildtype human $^{10}$Fn3 molecule: amino acids at positions 1-29, 32, 34, 36, 48, 51-66, 68, 70, 72, 88, 90 and 92-101.

"Front" Binders

In some embodiments, the polypeptides provided herein comprise a Fn3, e.g., $^{10}$Fn3, domain comprising a solubility enhancing mutation, e.g., a T58 mutation, and having modifications in the CD, DE and, in some cases, EF loops, wherein the loop modifications all contribute to target binding. These polypeptides are referred to as "front binders." The front binders may additionally comprise modifications in one or more scaffold regions, particularly in scaffold regions that flank or are adjacent to a modified loop region. For example, the front binders may comprise a scaffold modification in one or more of β-strand C, β-strand D, and/or β-strand E relative to the sequences of the corresponding β-strands of the wildtype Fn3 domain, e.g., human $^{10}$Fn3 domain (SEQ ID NO: 1 or 5). Preferably the hydrophobic core residues are not modified relative to the wildtype sequence. Exemplary scaffold modifications that may be present in front binders, include modifications at one or more positions corresponding to amino acid positions 36, 49, 58 and/or 50 of SEQ ID NO: 1 or 5. Such scaffold modifications may contribute to binding to the target together with the modified loops. In certain embodiments, the front binders may comprise clusters of modifications spanning several loop and strand regions of the Fn3, e.g., $^{10}$Fn3, domain. In particular, the front binders may comprise modifications in at least 15, 20, 24, 25, or 27 of the 31 residues between the amino acids corresponding to residues 36 through 66 of the wildtype Fn3, e.g., human $^{10}$Fn3, domain (SEQ ID NO: 1 or 5). The loop and/or strand modifications may include amino acid substitutions, deletions and/or insertions, or combinations thereof. In exemplary embodiments, the CD loop is extended in length or reduced in length relative to the CD loop of the Fn3, e.g., wildtype human $^{10}$Fn3, domain (SEQ ID NO: 1 or 5).

"Back" Binders

In some embodiments, the polypeptides provided herein comprise a Fn3, e.g., $^{10}$Fn3, domain comprising a solubility enhancing mutation, e.g., a T58 mutation, and having modifications in the EF and FG loops, wherein the loop modifications contribute to binding the same target. These polypeptides are referred to as "back binders" herein. The back binders may comprise additional modifications in other loop and/or scaffold regions. For example, a back binder may contain modifications in at least a portion of the AB loop, preferably the N-terminal portion of the AB loop. In an exemplary embodiment, the first two amino acids of the AB loop (i.e., corresponding to amino acid residues 14 and 15 of the wildtype $^{10}$Fn3 domain) are modified relative to the wildtype sequence. In certain embodiments, a back binder may also contain one or more scaffold modifications, particularly modifications in one or more scaffold regions that are adjacent to a modified loop region. For example, back binders may contain one or more modifications in one or more of β-strand A, β-strand G, the N-terminal region, and/or the C-terminal region. Preferably the hydrophobic core residues are not modified relative to the wildtype sequence. Exemplary scaffold modifications include modifications at one or more positions corresponding to amino acid positions 1-7, 9-13, 89, 91, 93 and/or 94 of SEQ ID NO: 1 or 5. One or more of the additional loop and/or scaffold modifications may contribute to binding to the target along with the modified EF and FG loops. Suitable loop and/or scaffold region modifications include amino acid substitutions, deletions and/or insertions, or combinations thereof. In certain embodiments, the amino acid sequence of the FG loop is extended in length or reduced in length relative to the FG loop of the wildtype human $^{10}$Fn3 domain (SEQ ID NO: 1 or 5).

In certain embodiments, a back binder may comprise a cluster of modified amino acid residues over a contiguous span of several regions in the $^{10}$Fn3 domain. For example, at least 14 of the first 15 amino acid residues of the Fn3, e.g., $^{10}$Fn3, domain may be modified relative to the corresponding residues in the wildtype Fn3, e.g., human $^{10}$Fn3 domain (SEQ ID NO: 1 or 5), and/or at least 15 of the 18 residues between the amino acids corresponding to residues 80 through 97 (or 94) of the wildtype Fn3, e.g., human $^{10}$Fn3, domain (SEQ ID NO: 1 or 5) may be modified relative to the corresponding residues in the wildtype sequence.

"South Pole" Binders

In certain embodiments, the application provides polypeptides comprising a Fn3, e.g., $^{10}$Fn3, domain, wherein the $^{10}$Fn3 domain comprises a solubility enhancing mutation, e.g., a T58 mutation, and modifications in the amino acid sequences of β-strand A, loop AB, β-strand B, loop CD, β-strand E, loop EF, and β-strand F, relative to the sequences of the corresponding regions of the wildtype sequence. These polypeptides are referred to as "south pole binders" or "SP binders" herein. The modified loops and strands contribute to binding to the same target. The amino acid sequence of the CD loop may be extended in length or reduced in length relative to the CD loop of the wildtype Fn3, e.g., human $^{10}$Fn3, domain (SEQ ID NO: 1 or 5). The south pole binders may comprise additional modifications in β-strand G and/or the C-terminal region relative to the sequence of the corresponding region of the wildtype sequence. In exemplary embodiments, the south pole binders may comprise one or more modifications at amino acids corresponding to positions 11, 12, 19, 60, 61, 69, 91, 93 and 95-97 of the wildtype sequence.

"Northwest" Binders

In some embodiments, the application provides polypeptides comprising a Fn3, e.g., $^{10}$Fn3, domain comprising a solubility enhancing mutation, e.g., a T58 mutation, and comprising modified BC, DE and FG loops, as compared to the corresponding BC, DE and FG loop sequences set forth in SEQ ID NO: 1 or 5, as well as additional modifications in one or more of β-strand C, β-strand D, β-strand F and β-strand G strand residues. The β-strand and loop region modifications together contribute to binding to the target. These proteins are referred to as "Northwest binders", or "NW binders", herein. In exemplary embodiments, the NW binders comprise one or more scaffold modifications at any one of, or combination of, amino acid positions corresponding to scaffold region positions R33, T49, Y73 and S89 of SEQ ID NO: 1 or 5. Suitable modifications in loop and scaffold regions include amino acid substitutions, deletions and/or insertions, or combinations thereof. In certain embodiments, one or more of the BC, DE and FG loops are extended in length or reduced in length, or combinations thereof, relative to the wildtype sequence. In one embodiment, each of the BC, DE and FG loops are extended in length or reduced in length, or combinations thereof, relative to the wildtype sequence (e.g., SEQ ID NO: 1 or 5). In certain embodiments, only a portion of the BC loop is modified, particularly the C-terminal portion, relative to the wildtype sequence. For example, the BC loop may be modified only at amino acid residues corresponding to amino acids 27-31 of the wildtype BC loop, whereas the rest of the BC loop (i.e., corresponding to residues 23-26 of the wildtype loop) are left unmodified.

"Northeast" Binders

In some embodiments, the application provides polypeptides comprising a Fn3, e.g., $^{10}$Fn3, domain comprising a solubility enhancing mutation, e.g., a T58 mutation, and comprising a modified BC, DE and FG loop as well as one or more additional modifications in any one of, or combination of, the N-terminal region, β-strand A, β-strand B and/or β-strand E. These proteins are referred to as "Northeast binders", or "NE binders", herein. In exemplary embodiments, the NE binders are modified at any one of, or combination of, amino acids corresponding to scaffold region positions 1-7, E9, L19, S21 and/or T58 of the wildtype sequence (SEQ ID NO: 1 or 5). The combination of modified loop and scaffold regions contributes to binding to the target.

"South Front" Binders

In some embodiments, the application provides polypeptides comprising a Fn3, e.g., $^{10}$Fn3, domain comprising a solubility enhancing mutation, e.g., a T58 mutation, and comprising modifications in one or more of the AB, CD, DE and EF loops, as well as additional modifications in one or more of β-strand B, β-strand D and/or β-strand E. These proteins are referred to as "South Front binders" herein. The combination of modified loop and strand residues contributes to binding to the target. In exemplary embodiments, a South Front binder may be modified at one or more amino acid positions corresponding to scaffold region positions L19, T49, T58, S60, and/or G61 of SEQ ID NO: 1 or 5 and/or at one or more amino acid positions corresponding to loop region positions T14-S17, P51, T56, G40-E47, and/or K63-G65 of SEQ ID NO: 1 or 5. In exemplary embodiments, a South Front binder may be extended in length or reduced in length in the AB loop, between amino acids corresponding to residues 18 and 20 of the wildtype sequence, and/or in the CD loop.

"AG" Binders

In some embodiments, the application provides polypeptides comprising a Fn3, e.g., $^{10}$Fn3, domain comprising a solubility enhancing mutation, e.g., a T58 mutation, and comprising a modified β-strand A and β-strand G, as compared to the corresponding strand of SEQ ID NO: 1 or 5. These proteins are referred to as "AG Binders" or "AG Strand" binders herein. In certain embodiments, the AG strand binders comprise clusters of modifications at the N-terminal and C-terminal portions of the Fn3, e.g., $^{10}$Fn3, domain, whereas the middle portion of the Fn3 remains unmodified. For example, an AG strand binder may comprise modifications at 16 out of 19 of the first 19 amino acids in the $^{10}$Fn3 domain (i.e., corresponding to amino acid positions 1-19 of SEQ ID NO: 1 or 5) and modifications at 13-17 out of 18 of the last 18 amino acids in the $^{10}$Fn3 domain (i.e., corresponding to amino acid positions 84-101 of SEQ ID NO: 1) or at 14-18 out of 22 of the last 22 amino acids in the $^{10}$Fn3 domain (i.e., corresponding to amino acid positions 80-101 of SEQ ID NO: 1). In exemplary embodiments, an AG binder may comprise modifications at one or more positions corresponding to positions 1-7, 9, 11-17, 19, 84-89 and 91-97 of SEQ ID NO: 1. Preferably the modified regions in an AG binder contribute to binding to the same target.

"Southwest" Binders

In some embodiments, the application provides polypeptides comprising a Fn3, e.g., $^{10}$Fn3, domain comprising a solubility enhancing mutation, e.g., a T58 mutation, and comprising a modified CD and EF loop, as well as additional modifications in any one of, or combination of residues corresponding to positions 69 or 91-97 of SEQ ID NO: 1. These proteins are referred to as "Southwest binders", or "SW binders", herein. The modified loop and scaffold regions contribute to binding to the target.

Proteins Having Reduced Immunogenicity

In certain embodiments, the application provides polypeptides having reduced immunogenicity comprising a $^{10}$Fn3 domains wherein a portion of the BC loop is left as wildtype. Preferably such polypeptides have lower immunogenicity relative to an equivalent polypeptide with modifications in a greater portion of the BC loop. In exemplary embodiments, the N-terminal portion of the BC loop is left as wildtype. For example, the first 1, 2, 3, 4, 5, or 5 residues of the BC loop may be left as wildtype, while the remaining C-terminal residues of the BC loop can be modified. In Fn3 designs having at least a portion of the N-terminal region of the BC loop as wildtype, it may be desirable to leave all or a portion of β-strand B and/or β-strand C unmodified relative to the wildtype sequence as well, particularly the portions of β-strand B and/or β-strand C that are adjacent to the BC loop (i.e., the C-terminal portion of β-strand B and/or the N-terminal portion of β-strand C). In exemplary embodiments, Fn3 domains having the wildtype sequence in an N-terminal portion of the BC loop and reduced immunogenicity may not have any modifications in the N-terminal region, β-strand A, AB loop, and β-strand B. In Fn3 designs with a portion of the BC loop as wildtype, the modified portion of the BC loop may contribute to target binding along with modifications in other regions of the $^{10}$Fn3 domain.

In certain embodiments, the application provides polypeptides having reduced immunogenicity comprising Fn3 domains, wherein the strong HLA anchor in the region of β-strand B/BC loop/β-strand C (the "BC anchor") has been removed or destroyed (e.g., modified relative to the wildtype sequence in a manner that reduces binding affinity to one or more HLA receptors). For example, the BC anchor may be removed or destroyed by modifying the Fn3, e.g., $^{10}$Fn3, domain at one or more positions corresponding to positions L19, S21, R33 and/or T35 of SEQ ID NO:1 or 5. When the BC anchor has been removed or destroyed, it is possible to modify the sequence of the BC loop without significantly increasing the immunogenic potential of the BC region. Accordingly, many such Fn3 designs have modifications in the BC loop in addition to the modifications in β-strand B and/or β-strand C. The BC loop may contribute to target binding, optionally in combination with modifications in other regions of the Fn3 domain. The modifications in β-strand B and/or β-strand C may or may not contribute to target binding.

Fn3 Solubility Enhancing Mutations

In some embodiments, a modified Fn3 domain comprises an amino acid sequence that is based on a sequence selected from SEQ ID NOs:1-29 and 65-66, wherein the Fn3 domain comprises a solubility enhancing mutation. A solubility enhancing mutation may be in a loop or a non-loop region. For example, a solubility enhancing mutation may be at a location corresponding to at least one of residues 24, 27, 54, 58, 78, 80 and 83 of SEQ ID NO: 1. In some embodiments, a solubility enhancing mutation is located in a non-loop region, such as a β-strand. For example, a solubility enhancing mutation may be located in β-strand E, such as at Threonine (T) 58.

In some embodiments, a solubility enhancing mutation, e.g., a mutation at residue 58, in a Fn3 domain that binds specifically to a target, does not contribute to the binding of the Fn3 domain to the target. In some embodiments, the amino acid that is mutated to enhance the solubility, e.g., T58, does not contribute to the binding of the Fn3 domain to its target. In some embodiments, the amino acid that is mutated to enhance the solubility, e.g., T58, is not in contact with the target.

In some embodiments, a solubility enhancing mutation, e.g., a mutation at residue 58, in a Fn3 domain that binds specifically to a target, contributes to the binding of the Fn3 domain to the target. In some embodiments, the amino acid that is mutated to enhance the solubility, e.g., T58, contributes to the binding of the Fn3 domain to its target. In some embodiments, the amino acid that is mutated to enhance the solubility, e.g., T58, is in contact with the target.

In some embodiments, the solubility of the modified Fn3 domain may be enhanced relative to the solubility of a Fn3 domain comprising an amino acid sequence wherein the amino acid corresponding to residue 58 of SEQ ID NO: 1 is not mutated. In some embodiments, the solubility of the modified Fn3 domain may be enhanced relative to the solubility of a Fn3 domain comprising the same amino acid sequence except that the amino acid corresponding to residue 58 of SEQ ID NO: 1 is not mutated.

In some embodiments, the modified Fn3 domain may comprise an amino acid sequence that is based on a sequence selected from SEQ ID NOs:1-29 and 65-66, wherein the amino acid corresponding to residue 58 of SEQ ID NO: 1 is mutated and wherein the solubility of the modified Fn3 domain is enhanced relative to the solubility of a Fn3 domain wherein the amino acid corresponding to residue 58 of SEQ ID NO: 1 is not mutated.

In some embodiments, the modified Fn3 domain may comprise an amino acid sequence that is 75%, 80%, 85%, 90%, 95%, or 98% identical to an amino acid sequence selected from SEQ ID NOs:1-29 and 65-71.

In some embodiments, the modified Fn3 domain may comprise an amino acid sequence selected from SEQ ID NOs:17-29, wherein the amino acid corresponding to residue 58 of SEQ ID NO: 1 is mutated and wherein the solubility of the modified Fn3 domain is enhanced relative to the solubility of a Fn3 domain wherein the amino acid corresponding to residue 58 of SEQ ID NO: 1 is not mutated. In some embodiments, the modified Fn3 domain may comprise an amino acid sequence selected from SEQ ID NOs: 17-29, wherein the amino acid corresponding to residue 58 of SEQ ID NO: 1 is mutated to Glu (E) or Asp (D). and wherein the solubility of the modified Fn3 domain is enhanced relative to the solubility of a Fn3 domain wherein the amino acid corresponding to residue 58 of SEQ ID NO: 1 is not mutated.

In some embodiments, the modified Fn3 domain may comprise an amino acid sequence selected from SEQ ID NOs:67-68, wherein the amino acid corresponding to residue 58 of SEQ ID NO: 1 is mutated and wherein the solubility of the modified Fn3 domain is enhanced relative to the solubility of a Fn3 domain wherein the amino acid corresponding to residue 58 of SEQ ID NO: 1 is not mutated. In some embodiments, the modified Fn3 domain may comprise an amino acid sequence selected from SEQ ID NOs: 69-71.

In some embodiments, the modified Fn3 domain described herein may be based on a $^{10}$Fn3 domain (e.g. any one of human $^{10}$Fn3 domains of SEQ ID NO:1-16, or any one of human $^{10}$Fn3 domains of SEQ ID NO:17-29), a $^{7}$Fn3 domain (e.g. human $^{7}$Fn3 domain of SEQ ID NO:65), or a $^{14}$Fn3 domain (e.g. human $^{14}$Fn3 domain SEQ ID NO:66), wherein the amino acid corresponding to residue 58 of SEQ ID NO: 1 may be mutated. In some embodiments, the modified Fn3 domain may be a modified $^{10}$Fn3 domain wherein the amino acid corresponding to residue 58 of SEQ ID NO: 1 may be mutated.

In some embodiments, the amino acid corresponding to residue 58 of SEQ ID NO: 1 may be mutated to any amino acid except Thr (T). In some embodiments, the amino acid corresponding to residue 58 of SEQ ID NO: 1 may be mutated to a hydrophilic amino acid. In some embodiments, the amino acid corresponding to residue 58 of SEQ ID NO: 1 may be mutated to an amino acid selected from Gln (Q), Glu (E), and Asp (D). In some embodiments, the amino acid corresponding to residue 58 of SEQ ID NO: 1 may be mutated to an amino acid selected from Glu (E) and Asp (D). In some embodiments, the amino acid corresponding to residue 58 of SEQ ID NO: 1 may be mutated to Glu (E) in a $^{10}$Fn3 domain. In some embodiments, the amino acid corresponding to residue 58 of SEQ ID NO: 1 may be mutated to Asp (D) in a $^{10}$Fn3 domain.

In some embodiments, in the modified Fn3 domain, the amino acid corresponding to residue 58 of SEQ ID NO: 1 is not mutated to Ala (A). In some embodiments, the amino acid corresponding to residue 58 of SEQ ID NO: 1 is not mutated to Ile (I). In some embodiments, the amino acid corresponding to residue 58 of SEQ ID NO: 1 is not mutated to Arg (R), His (H), or Lys (K). In some embodiments, the amino acid corresponding to residue 58 of SEQ ID NO: 1 is not mutated to Ser (S) or Asn (N). In some embodiments, the amino acid corresponding to residue 58 of SEQ ID NO: 1 is not mutated to Cys (C), Gly (G), or Pro (P). In some embodiments, the amino acid corresponding to residue 58 of SEQ ID NO: 1 is not mutated to Val (V), Leu (L), Met (M), Phe (F), Tyr (Y), or Trp (W).

In some embodiments, if the amino acid corresponding to residue 58 of SEQ ID NO: 1 is mutated to Ile (I), at least one of the amino acids corresponding to residues 23-29, 52-54 and 56 of SEQ ID NO:1 is the same as the corresponding residue of SEQ ID NO: 1.

In some embodiments, if the amino acid corresponding to residue 58 of SEQ ID NO: 1 is mutated to Ala (A), at least one of the amino acids corresponding to residues 23, 24, 26, 29, 52-54, and 56 of SEQ ID NO:1 is the same as the corresponding residue of SEQ ID NO: 1.

In some embodiments, if the amino acid corresponding to residue 58 of SEQ ID NO: 1 is mutated to Ala (A), three or more residues of the BC loop are the same as the corresponding residues in the BC loop of SEQ ID NO:1, or two or more residues of the DE loop are the same as the corresponding residues in the DE loop of SEQ ID NO:1.

In some embodiments, if the amino acid corresponding to residue 58 of SEQ ID NO: 1 is mutated to Ala (A) or Ile (I), the first two residues of the BC loop are the same as the corresponding residues in the BC loop of SEQ ID NO:1.

In some embodiments, if the amino acid corresponding to residue 58 of SEQ ID NO: 1 is mutated to Ala (A) or Ile (I), the first three residues of the BC loop are the same as the corresponding residues in the BC loop of SEQ ID NO:1.

In some embodiments, if the amino acid corresponding to residue 58 of SEQ ID NO: 1 is mutated to Ala (A) or Ile (I), the first four residues of the BC loop are the same as the corresponding residues in the BC loop of SEQ ID NO:1.

In some embodiments, if the amino acid corresponding to residue 58 of SEQ ID NO: 1 is mutated to Ala (A) or Ile (I), the first five residues of the BC loop are the same as the corresponding residues in the BC loop of SEQ ID NO:1.

In some embodiments, if the amino acid corresponding to residue 58 of SEQ ID NO: 1 is mutated to Ala (A) or Ile (I), the BC loop has the amino acid sequence of the corresponding loop of SEQ ID NO:1.

In some embodiments, a Fn3 domain comprises a solubility enhancing mutation at residue 58, and comprises an amino acid at position 19, 21 and/or 50 that corresponds to the wildtype residue at that position, e.g., Leu for residue 19, Ser for residue 21 and Ser for residue 60. In some embodiments, a Fn3 domain comprises a solubility enhancing mutation at residue 58, and an amino acid sequence wherein 1, 2, 3 or 4 of amino acids at positions 63-66 correspond to the wildtype residue at that position (e.g. K for residue 63, P for residue 64, G for residue 65, V for residue 66). In certain embodiments, a Fn3 domain may comprise a solubility enhancing mutation at residue 58, and an amino acid sequence wherein at least 1, 2, 3, 4, or 5 of the residues of loops AB, CD, DE EF or of the N-terminal 7 amino acids correspond to the wildtype residue at that position.

In certain embodiments, a Fn3 domain protein comprising a solubility enhancing mutation does not comprise an amino acid modification in loop AB relative to the amino acid sequence of the wildtype Fn3 domain. In certain embodiments, a Fn3 domain protein comprising a solubility enhancing mutation does not comprise an amino acid modification in loop BC relative to the amino acid sequence of the wildtype Fn3 domain. In certain embodiments, a Fn3 domain protein comprising a solubility enhancing mutation does not comprise an amino acid modification in loop CD relative to the amino acid sequence of the wildtype Fn3 domain. In certain embodiments, a Fn3 domain protein comprising a solubility enhancing mutation does not comprise an amino acid modification in loop DE relative to the amino acid sequence of the wildtype Fn3 domain. In certain embodiments, a Fn3 domain protein comprising a solubility enhancing mutation does not comprise an amino acid modification in loop EF relative to the amino acid sequence of the wildtype Fn3 domain. In certain embodiments, a Fn3 domain protein comprising a solubility enhancing mutation does not comprise an amino acid modification in loop FG relative to the amino acid sequence of the wildtype Fn3 domain. In certain embodiments, a Fn3 domain protein comprising a solubility enhancing mutation does not comprise an amino acid modification in a non-loop region, e.g., a β-strand relative to the amino acid sequence of the wildtype Fn3 domain. In certain embodiments, a Fn3 domain protein comprising a solubility enhancing mutation does not comprise an amino acid modification in the N-terminal or C-terminal domains relative to the amino acid sequence of the wildtype Fn3 domain. In certain embodiments, a Fn3 domain protein comprising a solubility enhancing mutation does not comprise an amino acid modification in β-strand A relative to the amino acid sequence of the wildtype Fn3 domain. In certain embodiments, a Fn3 domain protein comprising a solubility enhancing mutation does not comprise an amino acid modification in β-strand B relative to the amino acid sequence of the wildtype Fn3 domain. In certain embodiments, a Fn3 domain protein comprising a solubility enhancing mutation does not comprise an amino acid modification in β-strand C relative to the amino acid sequence of the wildtype Fn3 domain. In certain embodiments, a Fn3 domain protein comprising a solubility enhancing mutation does not comprise an amino acid modification in β-strand D relative to the amino acid sequence of the wildtype Fn3 domain. In certain embodiments, a Fn3 domain protein comprising a solubility enhancing mutation does not comprise an amino acid modification in β-strand E relative to the amino acid sequence of the wildtype Fn3 domain. In certain embodiments, a Fn3 domain protein comprising a solubility enhancing mutation does not comprise an amino acid modification in β-strand F relative to the amino acid sequence of the wildtype Fn3 domain. In certain embodiments, a Fn3 domain protein comprising a solubility enhancing mutation does not comprise an amino acid modification in β-strand G relative to the amino acid sequence of the wildtype Fn3 domain. In certain embodiments, a Fn3 domain protein comprising a solubility enhancing mutation does not comprise an amino acid modification in either of two loops, two strands, two loops and one strand, two loops and two strands, or one loop and two strands relative to the amino acid sequence of the wildtype Fn3 domain.

In certain embodiments, the BC loop of an Fn3 domain protein comprising a solubility enhancing mutation has the amino acid sequence of the corresponding loop of the wildtype human Fn3 domain, e.g., $^{10}$Fn3 domain (SEQ ID NO: 1). In certain embodiments, the first 2 residues of the BC loop of an Fn3 domain protein comprising a solubility enhancing mutation are the same as the corresponding residues in the BC loop of the wildtype human Fn3 domain, e.g., $^{10}$Fn3 domain (SEQ ID NO: 1). In certain embodiments, the first 3 residues of the BC loop of an Fn3 domain protein comprising a solubility enhancing mutation are the same as the corresponding residues in the BC loop of the wildtype human Fn3 domain, e.g., $^{10}$Fn3 domain (SEQ ID NO: 1). In certain embodiments, the first 4 residues of the BC loop of an Fn3 domain protein comprising a solubility enhancing mutation are the same as the corresponding residues in the BC loop of the wildtype human Fn3 domain, e.g., $^{10}$Fn3 domain (SEQ ID NO: 1). In certain embodiments, the first 5 residues of the BC loop of an Fn3 domain protein comprising a solubility enhancing mutation are the same as the corresponding residues in the BC loop of the wildtype human Fn3 domain, e.g., $^{10}$Fn3 domain (SEQ ID NO: 1).

Amino acid changes in loop and/or non-loop regions of a Fn3 domain that are made to enhance the solubility of a Fn3 domain preferably do not significantly affect the biological activity of the Fn3 domain. For example, a solubility enhancing mutation preferably does not significantly reduce the affinity of binding (e.g., Kd) of the Fn3 domain to its desired target. In some embodiments, a solubility enhancing mutation, e.g., a T58 mutation, may reduce the affinity of binding (Kd) of an Fn3 domain by less than 1%, 3%, 5%, 10%, 20%, 30%, 50%, 70%, or 90%. In some embodiments, a solubility enhancing mutation may not significantly reduce the stability (e.g., Tm) of a Fn3 domain or protein comprising a Fn3 domain. In some embodiments, a solubility enhancing mutation, e.g., a T58 mutations, may reduce the stability (e.g., Tm) of a Fn3 domain or protein comprising a Fn3 domain by less than 1%, 3%, 5%, 10%, 20%, 30%, 50%, 70%, or 90%, or regarding Tm, by less than 0.1° C., 0.3° C., 0.5° C., 0.7° C., 1° C., 2° C., 3° C., 4° C., 5° C., 6° C., 7° C., 8° C., 9° C., 10° C., 11° C., 12° C., or 13° C. In some embodiments, a solubility enhancing mutation does not significantly reduce either the stability or binding affinity of an Fn3 protein.

In some embodiments, in a Fn3 domain, the amino acid corresponding to residue 58 of SEQ ID NO: 1 may be mutated to a hydrophilic amino acid, wherein the solubility of the modified Fn3 domain may be enhanced relative to the solubility of the Fn3 domain wherein the amino acid corresponding to residue 58 of SEQ ID NO: 1 is not mutated, and wherein the mutation may reduce the stability (e.g., Tm) of the Fn3 domain by less than 1%, 3%, 5%, 10%, 20%, 30%, or 50%, or regarding Tm, by less than 1° C., 2° C., 3° C., 4° C., 5° C., 6° C., 7° C., 8° C., 9° C., 10° C., 11° C., 12° C., or 13° C. In some embodiments, in a Fn3 domain, the amino acid corresponding to residue 58 of SEQ ID NO: 1 may be mutated to an amino acid selected from Gln (Q), Glu (E), and Asp (D), wherein the solubility of the modified Fn3 domain may be enhanced relative to the solubility of the Fn3 domain wherein the amino acid corresponding to residue 58 of SEQ ID NO: 1 is not mutated, and wherein the mutation may reduce the stability (e.g., Tm) of the Fn3 domain by less than 1%, 3%, 5%, 10%, 20%, 30%, or 50%, or regarding Tm, by less than 1° C., 2° C., 3° C., 4° C., 5° C., 6° C., 7° C., 8° C., 9° C., 10° C., 11° C., 12° C., or 13° C. In some embodiments, in a Fn3 domain, the amino acid corresponding to residue 58 of SEQ ID NO: 1 may be mutated to Glu (E), wherein the solubility of the modified Fn3 domain may be enhanced relative to the solubility of the Fn3 domain wherein the amino acid corresponding to residue 58 of SEQ ID NO: 1 is not mutated, and wherein the mutation may reduce the stability (e.g., Tm) of the Fn3 domain by less than 5% 10% or 15%, or regarding Tm, by less than 1° C., 2° C., 3° C., 4° C., 5° C. or 10° C. In some embodiments, in a Fn3 domain, the amino acid corresponding to residue 58 of SEQ ID NO: 1 may be mutated to Asp (D), wherein the solubility of the modified Fn3 domain may be enhanced relative to the solubility of the Fn3 domain wherein the amino acid corresponding to residue 58 of SEQ ID NO: 1 is not mutated, and wherein the mutation may reduce the stability (e.g., Tm) of the Fn3 domain by less than 15% or 20%, or regarding Tm, by less than 5° C., 10° C. or 15° C.

In certain embodiments, the mutations described herein enhance the solubility of a protein that is a multivalent protein that comprises two or more Fn3 domains, e.g., $^{10}$Fn3 domains. For example, a multivalent protein may comprise 2, 3 or more Fn3 domains, e.g., $^{10}$Fn3 domains, that are covalently associated. In exemplary embodiments, the protein may be a bispecific or dimeric protein comprising two $^{10}$Fn3 domains. A solubility enhancing mutation, e.g., a mutation at T58, may be present in one or more of the Fn3 domains of a multimeric Fn3 protein. In certain embodiments, each Fn3 domain of a multimeric Fn3 protein may comprise a solubility enhancing mutation, e.g., a mutation at T58.

In some embodiments, the polypeptide described herein further comprise at least one pharmacokinetic (PK) moieties selected from: a polyoxyalkylene moiety, a human serum albumin binding protein, sialic acid, human serum albumin, transferrin, IgG, an IgG binding protein, and an Fc (or fragment thereof). In some embodiments, the PK moiety is the polyoxyalkylene moiety. In some embodiments, the polyoxyalkylene moiety is polyethylene glycol (PEG). In some embodiments, the PEG moiety is covalently linked to the polypeptide via a Cys or Lys amino acid. In some embodiments, the PEG is between about 0.5 kDa and about 100 kDa. In some embodiments, the PK moiety is an Fc fragment.

As described herein, the modified Fn3 domains may be used to bind to any target of interest for treatment of diseases or disorders. The diseases or disorders that may be treated will be dictated by the binding specificity of the Fn3 domains. In some embodiments, the polypeptide may specifically bind to a target that is not bound by a wildtype Fn3 domain (e.g., a human Fn3 domain of SEQ ID NO:1-16, 65, or 66). Exemplary targets include, for example, TNF-alpha, VEGFR2, PCSK9, IL-23, EGFR, IGF1R, DLL4, IL-17 and PXR. Merely as an example, modified Fn3 domains that bind to TNF-alpha may be used to treat autoimmune disorders such as rheumatoid arthritis, inflammatory bowel disease, psoriasis, and asthma. Modified Fn3 domains that bind to IL-17 may be used to treat asthma; and modified Fn3 domains that bind to DLL4 or EGFR may be used to treat hyperproliferative disorders or diseases associated with unwanted angiogenesis, such as cancers or tumors.

The application also provides methods for administering the polypeptides described herein to a subject. In some embodiments, the subject is a human. In some embodiments, the proteins are pharmaceutically acceptable to a mammal, in particular a human. A "pharmaceutically acceptable" composition refers to a composition that is administered to an animal without significant adverse medical consequences.

In certain embodiments, the application provides pharmaceutically acceptable compositions comprising the polypeptide described herein. In some embodiments, the composition is essentially pyrogen free. In some embodiments, the composition is substantially free of microbial contamination making it suitable for in vivo administration. The composition may be formulated, for example, for intravenous (IV), intraperitoneal (IP) or subcutaneous (SubQ) administration. In some embodiments, the composition comprises a physiologically acceptable carrier. In some embodiments, the pH of the composition is between 2-9, 3-8, 4-7.5, 4-7, 4-6.5, or between 4-5.5, or is about 4.0, 4.5, 5.0, or 5.5. In some embodiments, the concentration of the polypeptide is 1-1000, 1-500, 1-200, 1-100, 1-50, 1-20, 1-10, 1-5, or 0.5-2 mg/ml in the composition.

In certain embodiments, the application provides a nucleic acid encoding the polypeptides as described herein. Vectors containing polynucleotides for such polypeptides are included as well. Suitable vectors include, for example, expression vectors. A further aspect of the application provides for a cell, comprising a polynucleotide, vector, or expression vector, encoding a polypeptide described herein. Sequences are preferably optimized to maximize expression in the cell type used. In some embodiments, expression is in a bacterial cell, such as *E. coli*. In other embodiments, expression is in a mammalian cell. In one embodiment, the cell expresses a polypeptide comprising a modified Fn3 domain as described herein. In certain embodiments, the polynucleotides encoding polypeptides described herein are codon optimized for expression in the selected cell type. Also provided are methods for producing a polypeptide as described herein, comprising culturing a host cell comprising a nucleic acid, vector, or expression vector encoding the polypeptide described and recovering the expressed polypeptide from the culture.

In certain embodiments, the application provides libraries comprising a plurality of the polypeptides described herein. The libraries provided herein may comprise, for example, at least $10^4$, $10^5$ $10^6$ $10^7$, $10^8$, $10^9$, $10^{10}$, $10^{11}$, $10^{12}$, $10^{13}$, or $10^{14}$, or more polypeptides, each optional comprising a different amino acid sequence. Also provided are methods for identifying a polypeptide that binds to a target of interest from one of the libraries described herein. For example, a library screening method may comprise, for example, contacting a library of the polypeptides described herein with a target of interest, and isolating members of the library that bind to the target (e.g., with a particular affinity or under suitable wash conditions). The isolation step may be carried out using any suitable method, such as phage display or mRNA display. Similarly, target binding may be conducted using any suitable method such as immobilizing the target on a solid support (e.g., a column, chip, bead, etc.) and mixing the immobilized target with the library under conditions suitable to allow protein binding. The bound library members may then be separated from unbound library members to yield an isolated Fn3 protein that binds to the target. In certain embodiments, the isolation method may involve repeated rounds of target binding and isolation steps.

Provided are also isolated polypeptides identified by a method described herein. In some embodiments, the isolated polypeptide may bind to the target with a $K_d$ of less than 1500 nM (1.5 µM), 1000 nM (1 µM), 500 nM, 400 nM, 300 nM, 200 nM, 100 nM, 50 nM, 20 nM, 10 nM, 5 nM, 1 nM, 500 pM, 100 pM or less. In some embodiments, the polypeptide may bind to the target with a $K_d$ between 1 pM and 1 µM, between 100 pM and 500 nM, between 1 nM and 500 nM, or between 1 nM and 100 nM.

EXEMPLARY SEQUENCES

WT $^{10}$Fn3 Domain:
(SEQ ID NO: 1)
VSDVPRDLEVVAATPTSLLISWDAPAVTVRYYRITYGETGGNSPVQEF
TVPGSKSTATISGLKPGVDYTITVYAVTGRGDSPASSKPISINYRTEI
DKPSQ $^{10}$Fn3 Domain of SEQ ID NO: 1 with D97E:
(SEQ ID NO: 2)
VSDVPRDLEVVAATPTSLLISWDAPAVTVRYYRITYGETGGNSPVQEF
TVPGSKSTATISGLKPGVDYTITVYAVTGRGDSPASSKPISINYRTEI
EKPSQ WT $^{10}$Fn3 Domain Core Sequence version 1:
(SEQ ID NO: 3)
LEVVAATPTSLLISWDAPAVTVRYYRITYGETGGNSPVQEFTVPGSKS
TATISGLKPGVDYTITVYAVTGRGDSPASSKPISINY WT $^{10}$Fn3 Domain Core Sequence version 2:
(SEQ ID NO: 4)
EVVAATPTSLLISWDAPAVTVRYYRITYGETGGNSPVQEFTVPGSKST
ATISGLKPGVDYTITVYAVTGRGDSPASSKPISINYRT -continued

EXEMPLARY SEQUENCES

WT $^{10}$Fn3 Domain Core Sequence version 3:
(SEQ ID NO: 5)
VSDVPRDLEVVAATPTSLLISWDAPAVTVRYYRITYGETGGNSPVQEF
TVPGSKSTATISGLKPGVDYTITVYAVTGRGDSPASSKPISINYRT WT $^{10}$Fn3 Domain Core Sequence version 4:
(SEQ ID NO: 6)
VSDVPRDLEVVAATPTSLLISWDAPAVTVRYYRITYGETGGNSPVQEF
TVPGSKSTATISGLKPGVDYTITVYAVTGRGDSPASSKPISINYRTE WT $^{10}$Fn3 Domain Core Sequence version 5:
(SEQ ID NO: 7)
VSDVPRDLEVVAATPTSLLISWDAPAVTVRYYRITYGETGGNSPVQEF
TVPGSKSTATISGLKPGVDYTITVYAVTGRGDSPASSKPISINYRTEI WT $^{10}$Fn3 Domain Core Sequence version 6:
(SEQ ID NO: 8)
VSDVPRDLEVVAATPTSLLISWDAPAVTVRYYRITYGETGGNSPVQEF
TVPGSKSTATISGLKPGVDYTITVYAVTGRGDSPASSKPISINYRTEI
D $^{10}$Fn3 Domain Core Sequence version 7
(version 6 with D97E):
(SEQ ID NO: 9)
VSDVPRDLEVVAATPTSLLISWDAPAVTVRYYRITYGETGGNSPVQEF
TVPGSKSTATISGLKPGVDYTITVYAVTGRGDSPASSKPISINYRTEI
E WT $^{10}$Fn3 Domain Core Sequence version 8:
(SEQ ID NO: 10)
VSDVPRDLEVVAATPTSLLISWDAPAVTVRYYRITYGETGGNSPVQEF
TVPGSKSTATISGLKPGVDYTITVYAVTGRGDSPASSKPISINYRTEI
DK $^{10}$Fn3 Domain Core Sequence version 9
(version 8 with D97E):
(SEQ ID NO: 11)
VSDVPRDLEVVAATPTSLLISWDAPAVTVRYYRITYGETGGNSPVQEF
TVPGSKSTATISGLKPGVDYTITVYAVTGRGDSPASSKPISINYRTEI
EK WT $^{10}$Fn3 Domain Core Sequence version 10:
(SEQ ID NO: 12)
VSDVPRDLEVVAATPTSLLISWDAPAVTVRYYRITYGETGGNSPVQEF
TVPGSKSTATISGLKPGVDYTITVYAVTGRGDSPASSKPISINYRTEI
DKP $^{10}$Fn3 Domain Core Sequence version 11
(version 10 with D97E):
(SEQ ID NO: 13)
VSDVPRDLEVVAATPTSLLISWDAPAVTVRYYRITYGETGGNSPVQEF
TVPGSKSTATISGLKPGVDYTITVYAVTGRGDSPASSKPISINYRTEI
EKP WT $^{10}$Fn3 Domain Core Sequence version 12:
(SEQ ID NO: 14)
VSDVPRDLEVVAATPTSLLISWDAPAVTVRYYRITYGETGGNSPVQEF
TVPGSKSTATISGLKPGVDYTITVYAVTGRGDSPASSKPISINYRTEI
DKPS $^{10}$Fn3 Domain Core Sequence version 13
(version 12 with D97E):
(SEQ ID NO: 15)
VSDVPRDLEVVAATPTSLLISWDAPAVTVRYYRITYGETGGNSPVQEF
TVPGSKSTATISGLKPGVDYTITVYAVTGRGDSPASSKPISINYRTEI
EKPS WT $^{10}$Fn3 Domain with D80E Substitution
(SEQ ID NO: 16)
VSDVPRDLEVVAATPTSLLISWDAPAVTVRYYRITYGETGGNSPVQEF
TVPGSKSTATISGLKPGVDYTITVYAVTGRGESPASSKPISINYRTEI
DKPSQ Degenerate WT $^{10}$Fn3 Domain Core Sequence:
(SEQ ID NO: 17)
VSDVPRDLEVVAA(X)$_u$LLISW(X)$_v$YRITY(X)$_w$FTV(X)$_x$ATISGL
(X)$_y$YTITVYA(X)$_z$ISINYRT

| EXEMPLARY SEQUENCES |
|---|
| (SEQ ID NO: 18)<br>VSDVPRDLEVVAA(X)$_u$LLISW(X)$_v$YRITY(X)$_w$FTV(X)$_x$ATISGL(X)$_y$YTITVYA(X)$_z$ISINYRTE |
| (SEQ ID NO: 19)<br>VSDVPRDLEVVAA(X)$_u$LLISW(X)$_v$YRITY(X)$_w$FTV(X)$_x$ATISGL(X)$_y$YTITVYA(X)$_z$ISINYRTEI |
| (SEQ ID NO: 20)<br>VSDVPRDLEVVAA(X)$_u$LLISW(X)$_v$YRITY(X)$_w$FTV(X)$_x$ATISGL(X)$_y$YTITVYA(X)$_z$ISINYRTEID |
| (SEQ ID NO: 21)<br>VSDVPRDLEVVAA(X)$_u$LLISW(X)$_v$YRITY(X)$_w$FTV(X)$_x$ATISGL(X)$_y$YTITVYA(X)$_z$ISINYRTEIE |
| (SEQ ID NO: 22)<br>VSDVPRDLEVVAA(X)$_u$LLISW(X)$_v$YRITY(X)$_w$FTV(X)$_x$ATISGL(X)$_y$YTITVYA(X)$_z$ISINYRTEIDK |
| (SEQ ID NO: 23)<br>VSDVPRDLEVVAA(X)$_u$LLISW(X)$_v$YRITY(X)$_w$FTV(X)$_x$ATISGL(X)$_y$YTITVYA(X)$_z$ISINYRTEIEK |
| (SEQ ID NO: 24)<br>VSDVPRDLEVVAA(X)$_u$LLISW(X)$_v$YRITY(X)$_w$FTV(X)$_x$ATISGL(X)$_y$YTITVYA(X)$_z$ISINYRTEIDKP |
| (SEQ ID NO: 25)<br>VSDVPRDLEVVAA(X)$_u$LLISW(X)$_v$YRITY(X)$_w$FTV(X)$_x$ATISGL(X)$_y$YTITVYA(X)$_z$ISINYRTEIEKP |
| (SEQ ID NO: 26)<br>VSDVPRDLEVVAA(X)$_u$LLISW(X)$_v$YRITY(X)$_w$FTV(X)$_x$TISGL(X)$_y$YTITVYA(X)$_z$ISINYRTEIDKPS |
| (SEQ ID NO: 27)<br>VSDVPRDLEVVAA(X)$_u$LLISW(X)$_v$YRITY(X)$_x$FTV(X)$_x$ATISGL(X)$_y$YTITVYA(X)$_z$ISINYRTEIEKPS |
| (SEQ ID NO: 28)<br>VSDVPRDLEVVAA(X)$_u$LLISW(X)$_v$YRITY(X)$_w$FTV(X)$_x$ATISGL(X)$_y$YTITVYA(X)$_z$ISINYRTEIDKPSQ |
| (SEQ ID NO: 29)<br>VSDVPRDLEVVAA(X)$_u$LLISW(X)$_v$YRITY(X)$_w$FTV(X)$_x$ATISGL(X)$_y$YTITVYA(X)$_z$ISINYRTEIEKPSQ |
| (SEQ ID NO: 30)<br>MGVSDVPRDL |
| (SEQ ID NO: 31)<br>GVSDVPRDL |
| (SEQ ID NO: 32)<br>X$_n$SDVPRDL |
| (SEQ ID NO: 33)<br>X$_n$DVPRDL |
| (SEQ ID NO: 34)<br>X$_n$VPRDL |
| (SEQ ID NO: 35)<br>X$_n$PRDL |
| (SEQ ID NO: 36)<br>X$_n$RDL |
| (SEQ ID NO: 37)<br>X$_n$DL |
| (SEQ ID NO: 38)<br>MASTSG |
| (SEQ ID NO: 39)<br>EIEK |

| EXEMPLARY SEQUENCES |
|---|
| (SEQ ID NO: 40)<br>EGSGC |
| (SEQ ID NO: 41)<br>EIEKPCQ |
| (SEQ ID NO: 42)<br>EIEKPSQ |
| (SEQ ID NO: 43)<br>EIEKP |
| (SEQ ID NO: 44)<br>EIEKPS |
| (SEQ ID NO: 45)<br>EIEKPC |
| (SEQ ID NO: 46)<br>HHHHHH |
| (SEQ ID NO: 47)<br>EIDK |
| (SEQ ID NO: 48)<br>EIDKPCQ |
| (SEQ ID NO: 49)<br>EIDKPSQ |
| (FibconB; SEQ ID NO: 50)<br>MPAPTDLRFTNETPSSLLISWTPPRVQITGY1IRYGPVGSDGRVKEFTVPPSVSSATITGLKPGTEYTISVIALKDNQESEPLRGRVTTGG |
| (SEQ ID NO: 51)<br>TPSS |
| (SEQ ID NO: 52)<br>TPPRVQI |
| (SEQ ID NO: 53)<br>VGSDGR |
| (SEQ ID NO: 54)<br>PSVS |
| (SEQ ID NO: 55)<br>GLKPG |
| (SEQ ID NO: 56)<br>KDNQESEP |
| (SEQ ID NO: 57)<br>LDAPTDLQVTNVTDTSITVSWTPPSATITGYRITYTPSNGPGEPKELTVPPSSTSVTITGITPGVEYVVSVYALKDNQESPPLVGTCTT |
| (SEQ ID NO: 58)<br>LPAPKNLVVSEVTEDSLRLSWTAPDAAFDSFLIQYQESEKVGEAINLTVPGSERSYDETGLKPGTEYTVSIYGVKGGHRSNPLSAEFTT |
| (SEQ ID NO: 59)<br>TEDS |
| (SEQ ID NO: 60)<br>TAPDAAF |
| (SEQ ID NO: 61)<br>SEKVGE |
| (SEQ ID NO: 62)<br>GSER |
| (SEQ ID NO: 63)<br>GLKPG |
| (SEQ ID NO: 64)<br>KGGHRSN |

EXEMPLARY SEQUENCES

Wildtype <sup>7</sup>Fn3 domain:
(SEQ ID NO: 65)
PLSPPTNLHLEANPDTGVLTVSWERSTTPDITGYRITTTPTNGQQGNS
LEEVVHADQSSCTFDNLSPGLEYNVSVYTVKDDKESVPISDTIIP Wildtype <sup>14</sup>Fn3 domain:
(SEQ ID NO: 66)
NVSPPRRARVTDATETTITISWRTKTETITGFQVDAVPANGQTPIQRT
IKPDVRSYTITGLQPGTDYKIYLYTLNDNARSSPVVIDAST EGFR#8 <sup>10</sup>Fn3 domain:
(SEQ ID NO: 67)
MGVSDVPRDLEVVAATPTSLLISWDSGRGSYQYYRITYGETGGNSPVQ
EFTVPGPVHTATISGLKPGVDYTITVYAVTDHKPHADGPHTYHESPIS
INYRTEIDKPSQ EGFR#4 <sup>10</sup>Fn3 domain:
(SEQ ID NO: 68)
MGVSDVPRDLEVVAATPTSLLISWYWEGLPYQYYRITYGETGGNSPV
QEFTVPRDVNTATISGLKPGVDYTITVYAVTDWYNPDTHEYIYHTIP
ISINYRTEIDKPSQ EGFR#8-T58E <sup>10</sup>Fn3 domain:
(SEQ ID NO: 69)
MGVSDVPRDLEVVAATPTSLLISWDSGRGSYQYYRITYGETGGNSPVQ
EFTVPGPVHTAEISGLKPGVDYTITVYAVTDHKPHADGPHTYHESPIS
INYRTEIDKPSQ EGFR#8-T58D <sup>10</sup>Fn3 domain:
(SEQ ID NO: 70)
MGVSDVPRDLEVVAATPTSLLISWDSGRGSYQYYRITYGETGGNSPVQ
EFTVPGPVHTADISGLKPGVDYTITVYAVTDHKPHADGPHTYHESPIS
INYRTEIDKPSQ EGFR#4-T58E <sup>10</sup>Fn3 domain:
(SEQ ID NO: 71)
MGVSDVPRDLEVVAATPTSLLISWYWEGLPYQYYRITYGETGGNSPV
QEFTVPRDVNTAEISGLKPGVDYTITVYAVTDWYNPDTHEYIYHTIP
ISINYRTEIDKPSQ

EXAMPLES

The invention described herein will be more readily understood by reference to the following examples which are included merely for purposes of illustration of certain aspects and embodiments of the present disclosure, and are not intended to limit the invention in any way.

Example 1

Proteins Solubility Based on a Kosmotrope-Based Assay

This example describes aggregation propensity of proteins based on their relative solubility in ammonium sulfate (AS).

The effect of AS on protein solubility has been known for more than 80 years (Green, A. A., 1931, J. Biol. Chem. 93, 495-516), where it has most commonly been used for protein fractionation and purification. The mechanism of AS-induced protein precipitation or "salting out," is believed to involve the strong binding of water molecules by the polar kosmotropic sulfate anion, which dehydrates the protein surfaces, increases the chemical potential of the protein and causes the protein molecules to aggregate into an amorphous precipitate (Baldwin, R. L., 1996, Biophys J. 71:2056-63). Because the hydrophobic surfaces on the protein are preferentially dehydrated over the polar surfaces, AS-induced protein self-association is driven by the interaction of exposed hydrophobic surfaces, similar to the forces that drive aggregation in the absence of AS (Young, L. et al., 1994, Protein Sci. 3, 717-29; Arunachalam, J. and Gautham, N., 2008, Proteins. 71, 2012-25; Fink, A. L. 1998, Fold Des. 3, R9-23).

Described in this example is a method around this concept and its application in analyzing solubility or aggregation propensity of protein therapeutics of several different formats including single domain adnectins, multi-domain/multi-specific adnectins, adnectin-Fc fusions (Adn-Fcs), domain antibody (dAb) Fc-fusions (dAb-Fcs), and monoclonal antibodies (mAbs). The AS solubility data correlated with the protein aggregation propensity observed by other established methods (see Yamniuk, A. P. et al, 2013, J Pharm. Sci. 102, 2424-2439).

Materials and Methods

Proteins:

Single domain anti-EGFR adnectins, anti-EGFR/IGF1R bispecific tandem adnectins (EI-tandems), and PEGylated anti-EGFR/IGFR bispecific tandem adnectins were expressed and purified as previously described (Emanuel, S. L. et al., 2011, MAbs 3, 38-48). Adnectin-Fc and dAb-Fc fusions, as well as mAbs were expressed in HEK293-6E or CHO—S cells and purified by standard protein A affinity chromatography followed by preparative size exclusion chromatography (SEC). The Adn-Fc fusion proteins Adn-Fc-a, Adn-Fc-b, and Adn-Fc-e were over-expressed in *E. coli*, and each protein was refolded by resuspending the insoluble lysate fraction in 6 M Guanadinium HCl at pH 10.0 followed by dialysis against neutral pH buffer. The resulting refolded protein was purified as described above for the mammalian expressed fusions. All proteins were >95% pure as judged by SDS-PAGE.

Bench Scale Ammonium Sulfate Solubility Assay:

Bench-scale AS solubility studies were conducted at room temperature, and unless otherwise specified, the buffer was 10 mM $NaPO_4$, 130 mM NaCl pH 7.1. Samples were prepared by mixing protein stock solution with buffer and 3.5 M AS in matched buffer and pH, to produce a series of 8-12 samples of identical [protein] and increasing [AS] over a desired range. As observed in other studies (Trevino, S. R. et al., 2007, J Mol Biol. 366, 449-60; Schein, C. H., 1990, Biotechnology 8, 308-17), protein precipitation was rapid (<5 min), largely reversible upon dilution, and the soluble protein concentration remained stable for hours to days following removal of precipitated protein by centrifugation or filtration. In some instances the reversibility of precipitation was taken advantage of by generating samples of a given protein concentration at the lowest and highest desired AS concentrations, and mixing these two samples in appropriate volumes to generate the intermediate AS concentrations of the titration series. Samples were incubated for ~10 minutes at room temperature, followed by either centrifugation or filtration to remove precipitated protein, and protein concentration was determined using absorbance at 280 nm ($A_{280}$) of 2-3 ul of sample on a NanoDrop 2000 (Thermo Scientific) instrument.

Automated Ammonium Sulfate Solubility Assay:

Samples for the automated AS solubility assay were prepared using a Tecan Genesis Freedom 200 instrument at room temperature. First, 125 ul of protein stock solution was aspirated from a stock tube or plate, and 15 ul was dispensed into each of 8 wells in a 384 well plate (Whatman Uniplate #7701-5101). Next, 40 ul of 8 different AS solutions in buffer were aspirated from a 96 deep well plate and 35 ul was dispensed into the 8 protein wells with immediate gentle mixing. Following preparation of the last sample in a given set, all samples were incubated for an additional 5 minutes at room temperature. Then, samples were gently mixed and 47 ul of the protein/AS mixture was aspirated and 45 ul dispensed into a 384-well filter plate (PALL AcroPrep384 100 ul 0.45 um GHP # PN5071) placed on top of 384 well corning clear flat bottom UV plate (Corning UV 384 well #3675). Precipitated protein was filtered by centrifuging for 5 min at 21° C. Soluble protein was detected using a SpectroMax M5 plate reader, by measuring either the absorbance at 280 nm ($A_{280}$), or intrinsic fluorescence using an excitation wavelength of 280 nm and emission wavelength of 350 nm. Both detection methods generally gave comparable results, but $A_{280}$ detection was implemented as the default method for analysis.

Ammonium Sulfate Solubility Data Analysis and Curve Fitting:

The solubility of a protein in AS within the salting out region can be described by the linear relationship (Eq. 1) (Green, A. A., 1931, J. Biol. Chem. 93, 495-516):

$$\log S = \beta - K_s [AS] \quad (1)$$

where S is the protein solubility (protein concentration), β is the theoretical solubility at zero molar AS, Ks is the salting out constant, and [AS] is the AS concentration. Theoretically, the solubility of different proteins can be evaluated by comparing β values extrapolated from data in the salting out region. However, at the low protein concentrations and volumes desired for high throughput screening, there was limited data within the salting out region and therefore considerable uncertainty in the extrapolation, making β value comparison unreliable. Therefore, the salting out data were fitted to a sigmoidal curve function (Eq. 2):

$$Y = \frac{A_1 - A_2}{1 + e^{(x - ASm)/dx}} + A_2 \quad (2)$$

where $A_1$ is the initial Y value (absorbance or fluorescence), A2 is the final Y value, dx is the slope, and ASm is the salting out midpoint value. ASm analysis enabled a rapid quantitative comparison of the relative solubility of different proteins using either $A_{280}$ or fluorescence detection, and eliminated the necessity of converting the data to units of protein concentration. In general, calculated curve-fitting errors were in a similar range as the typical standard deviation for multiple independent measurements of a given protein (~0.01-0.04 M). The analysis of ASm values is also similar to the determination of PEGmidpoint values recently described by Gibson, T. J. et at (2011, J Pharm Sci. 100, 1009-21)

Accelerated Stability Studies:

Accelerated stability (forced degradation) studies were carried out for several adnectin-Fc molecules by incubating 1 mg/ml protein samples in 50 mM sodium phosphate ($NaH_2PO_4$) pH 7.0 and/or 50 mM sodium succinate ($Na_2C_4H_4O_4$) pH 6.0 for 2-4 weeks at temperatures ranging from 30-37° C. In all cases the incubation temperatures were at least 15° below the melting temperature (Tm) of the molecules as determined by either differential scanning calorimetry or thermal scanning fluorescence, in order to minimize non-native state degradation pathways. At various time points during the incubation, aliquots were removed and subjected to analytical size exclusion chromatography (SEC) analysis to determine the percentage of monomer, high molecular weight (HMW) and low molecular weight (LMW) species.

Ultrafiltration:

Ultrafiltration studies with anti-EGFR adnectin molecules were performed in VivaSpin 3000 MWCO concentrators at room temperature. 0.5-1.0 mg/ml protein in PBS pH 7.1 were slowly concentrated using centrifugal force to a target of 30-40 mg/ml with periodic mixing to avoid gradient formation, and then samples were incubated at 4° C. for 5 days. Precipitated protein was removed by centrifugation, and the soluble protein concentration was measured by A280 on a Nanodrop 2000 instrument, with the aggregation state measured by DLS as described below. Ultrafiltration studies for adnectin-Fc or dAb-Fc molecules were performed at 4° C. in VivaSpin 10,000 MWCO concentrators using positive pneumatic pressure regulated at 15 psi. To minimize gradient formation the concentrators were placed on a rocker plate set to 60 rpm for continual mixing, and samples were periodically removed and gently mixed by pipette. Typically starting samples were 1-7 mg/ml protein and were concentrated to ~50 mg/ml or higher over the course of 6-8 hours. 20-40 ul aliquots were removed at various time points and stored overnight at 4° C., followed by centrifugation to remove any precipitates, and then protein concentration was determined by A280 and the aggregation state of undiluted samples characterized by analytical SEC.

Dynamic Light Scattering:

Dynamic light scattering (DLS) studies were performed on a Wyatt DynaPro plate reader in 384 well plates at 25° C., using protein samples in 10 mM $NaPO_4$, 130 mM NaCl pH 7.1. Typical experimental parameters were 20 acquisitions of 5 s each per measurement, and measurements were recorded at least in triplicate and averaged to give the reported values. Intensity autocorrelation functions were fitted using the "Regularization" algorithm in the Dynamics software (Wyatt Technologies).

Results

Ammonium Sulfate Solubility of Adnectins:

Initial AS solubility studies were performed at bench scale using a set of single domain adnectin molecules (monoadnectins) with loops engineered to specifically bind to the EGFR receptor (EGFR #1-7), or IGF1R receptor (IGFR #1) (Emanuel, S. L. et al., 2011, MAbs 3, 38-48). An example salting out curve for 1 mg/ml IGF1R #1 is shown in FIG. 2. At low [AS], the measured [protein] was the same as the [protein] that was tested (1 mg/ml) indicating that no precipitation has occurred. However, at higher [AS], the solubility of IGFR #1 decreased resulting in precipitation or "salting out", and a corresponding decrease in the measured [protein]. The data were fit to a sigmoidal curve function to obtain the salting out midpoint value (ASm), as described in Material and Methods.

Salting out curves for EGFR #1-7 as well as IGFR #1 are shown in FIG. 3A, and ASm values together with other biophysical data are summarized in Table 1. Despite being monomeric proteins of similar size and structure, the adnectins each had unique salting out properties with ASm values ranging from 0.67 M for the least soluble adnectin (EGFR #4, SEQ ID NO:68), to ASm=2.01 M for the most soluble adnectin (EGFR #6). To determine whether these ASm values were predictive of the aggregation propensity observed using other methods, small scale ultrafiltration experiments was performed by concentrating each EGFR adnectin to a target concentration of 30-40 mg/ml. The soluble protein concentration was measured by $A_{280}$ and the aggregation state evaluated using DLS. These data showed that the adnectins with lower ASm values also had lower solubility limits (EGFR #2, EGFR #3, EGFR #4) and/or higher aggregation levels (EGFR #2, EGFR #4, EGFR #5)

at elevated protein concentrations (Table 1). In contrast, the solubility data showed no correlation with biophysical parameters such as thermal stability, or with parameters predicted from the amino acid sequence such as pI, charge, or hydropathy.

Figure 3B:
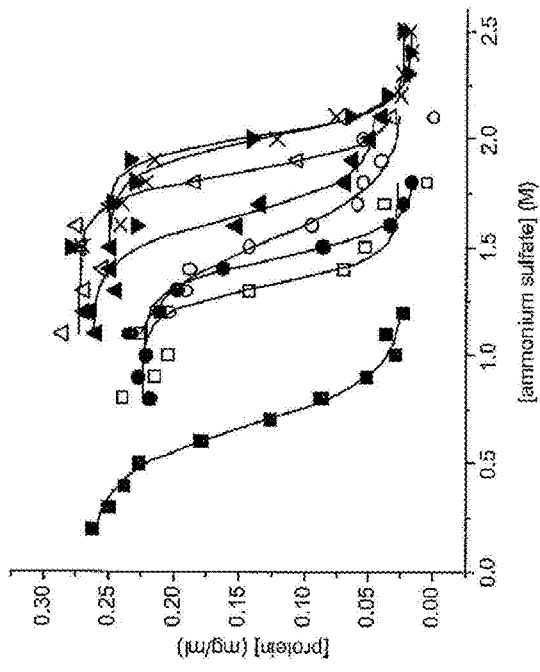
Figure 3C:
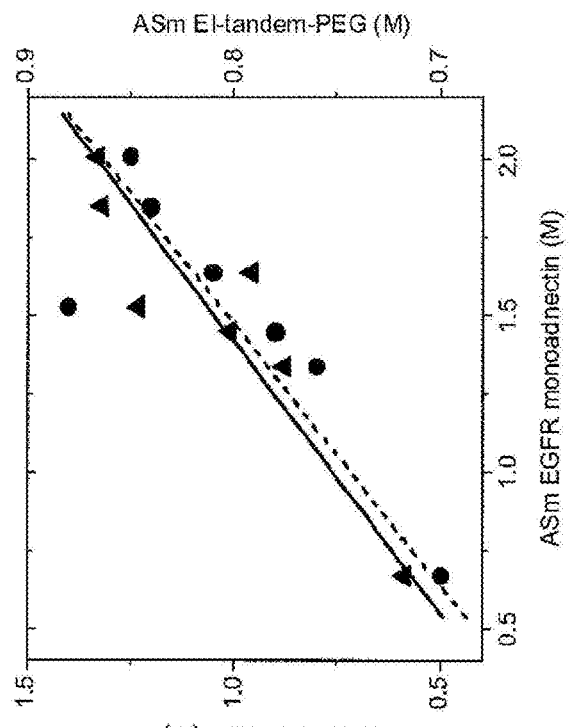
Figure 3D:
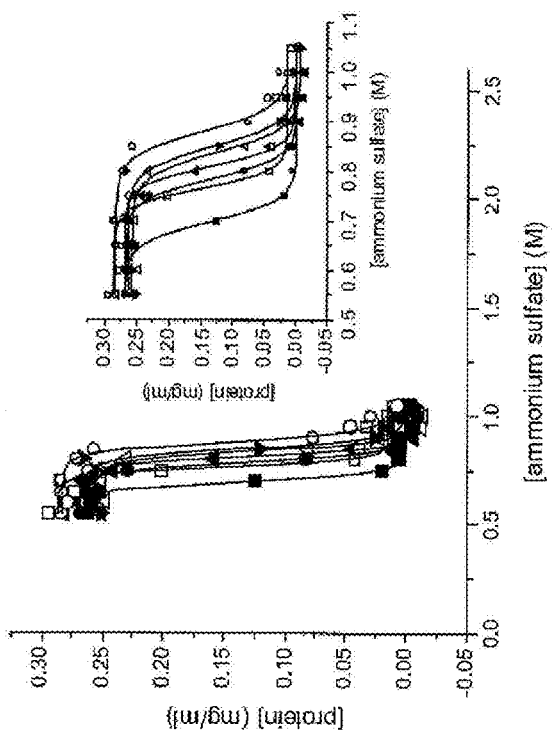
Figure 4:
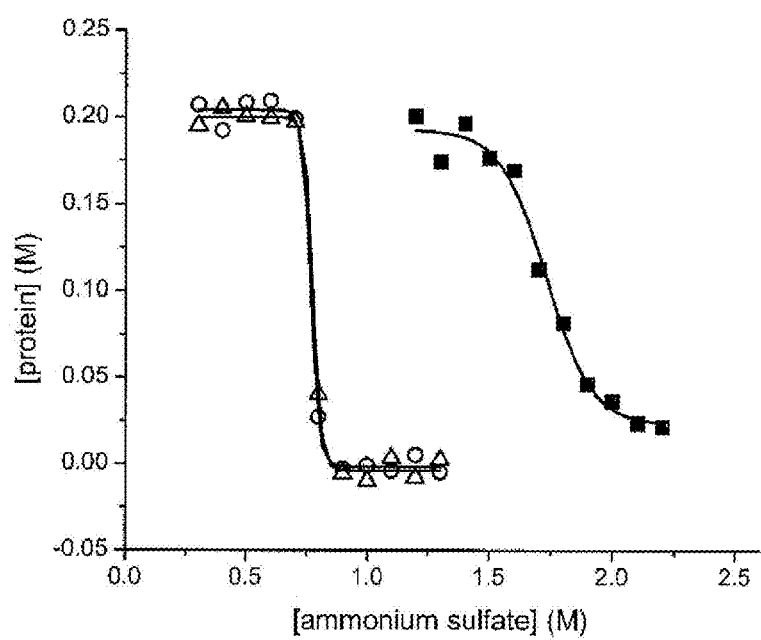
FIG. 4. Effect of PEGylation on the salting out of a domain antibody. A) Salting out curve for domain antibody molecule dAb1 (closed squares ■) or dAb1 PEGylated on a free cystine residue with 30 kDa linear PEG (open circles ○) or with 40 kDa single branched PEG (open up triangles Δ).

Similar bench scale salting out studies were performed using each of the EGFR #1-7 adnectins fused in-line with IGF1R #1 (EI-tandems), as well as for the EI-tandems covalently linked with a 40 kDa branched polyethylene glycol on the C-terminus (EI-tandem-PEG) which was done to extend serum half life (Emanuel et al., 2011, mAbs 3, 38-48). The slope of the salting out curves for the EI-tandems was similar to the monoadnectins (FIG. 3B). However, the PEGylated EI-tandems all salted out over a very narrow [AS] range of ~0.7-0.9 M and had much steeper salting out transitions (FIG. 3C). Similar behavior was also noted for other PEGylated proteins (FIG. 4), which may be likely due to additional volume exclusion effects from the attached PEG moiety (Stevenson, C. L. and Hageman, M. J., 1995, Pharm Res. 12, 1671-6). Interestingly, despite the differences in absolute AS solubility values for the different adnectin formats, the relative solubility ranking based on the identity of the anti-EGFR adnectin domain was largely conserved between formats (FIG. 3D), suggesting that the AS solubility of the monoadnectins is predictive of the solubility for the more complex multi-domain bispecific or PEG-formatted molecules.

Figure 5A:
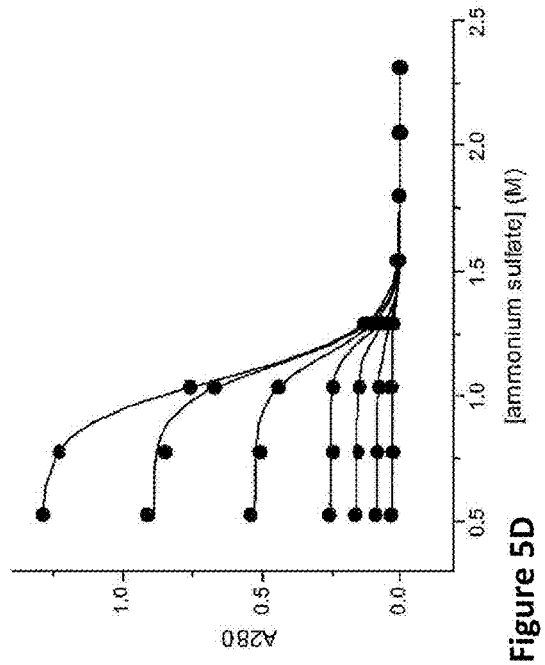
FIGS. 5A-5D show ammonium sulfate salting out data for Fc-fusion molecules using the automated method.
Figure 5B:
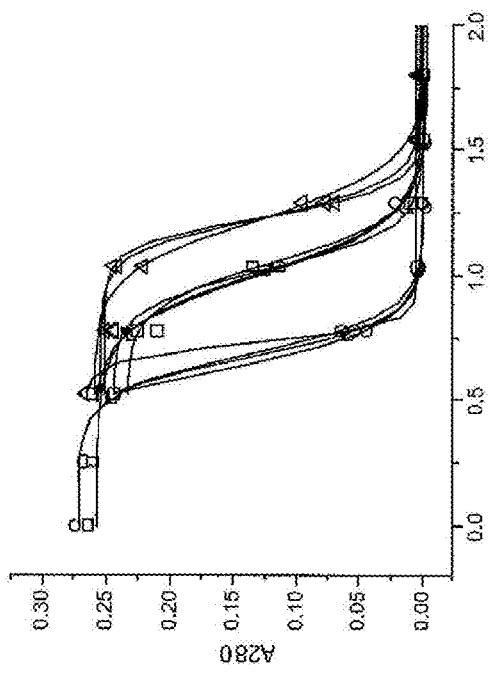
Figure 5C:
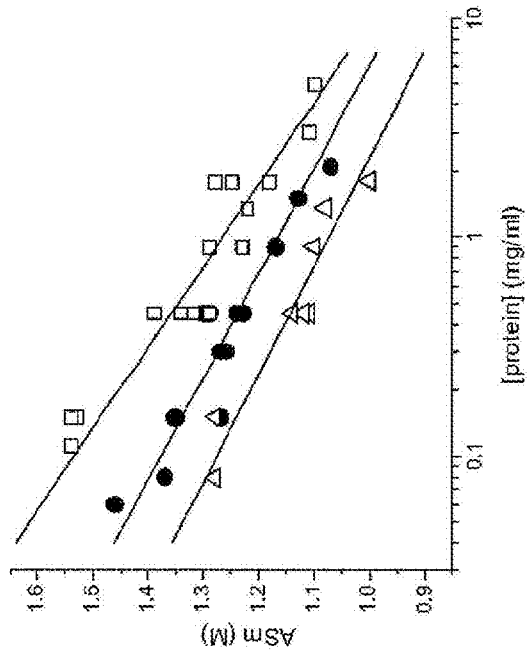
Figure 5D:
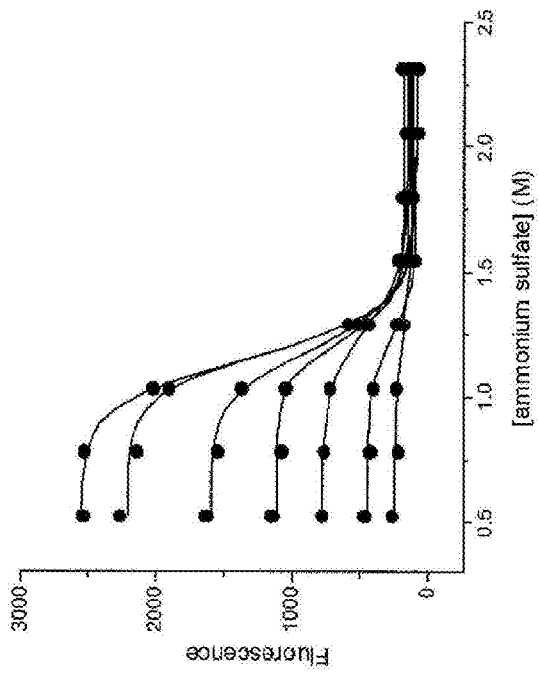

Ammonium Sulfate Solubility of Adnectin-Fc Fusions:

To determine if the AS solubility was predictive of the aggregation propensity of other protein therapeutic formats such as Fc-fusions, an automated, plate-based AS solubility method was used to generate salting out curves using either UV absorbance (A280) or fluorescence detection using as little as 50 micrograms of protein to generate an 8-point curve (FIGS. 5B and C). The relative solubility comparisons described below for Adn-Fcs, dAb-Fcs and mAbs were all performed using identical protein concentrations of 0.45 mg/ml.

Figure 6A:
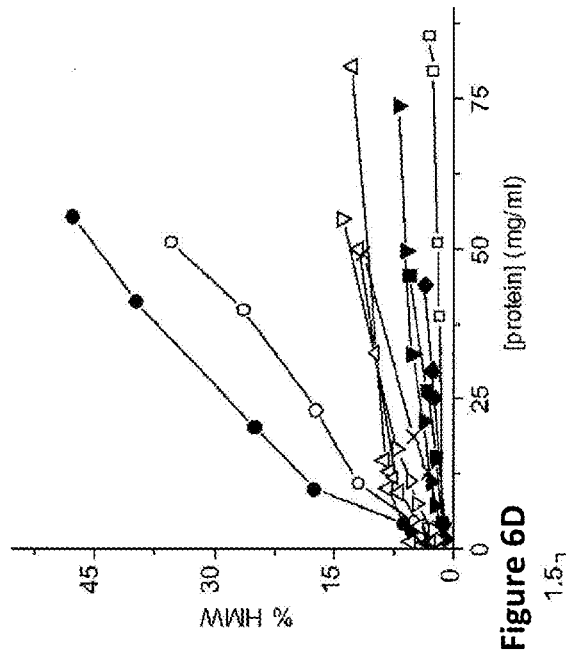
FIGS. 6A-6D. Solubility and stability data for Adn-Fcs.
Figure 6B:
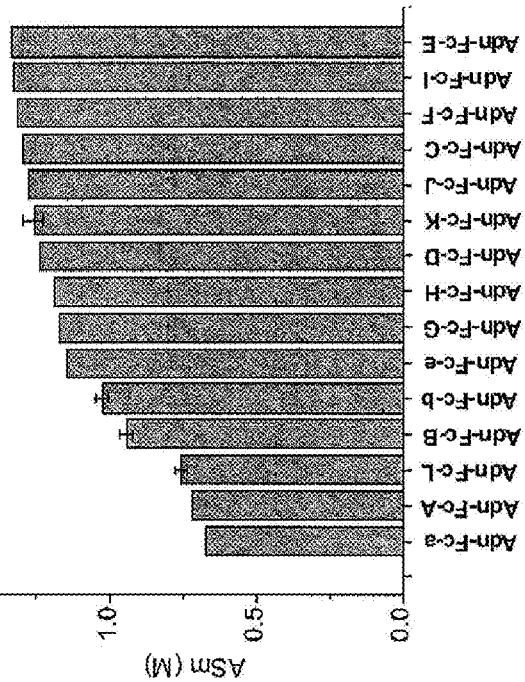

The automated AS solubility method was applied to a series of Adn-Fc molecules with diverse binding loops specifically selected to bind different therapeutic target proteins, each of which was fused to a human IgG1 Fc-domain (Adn-Fcs). Most Adn-Fcs were produced in mammalian cells and are indicated with upper case letters (i.e., Adn-Fc-A), but a few molecules were also produced in E. coli, and are indicated with lower case letters (i.e., Adn-Fc-a). The aggregation propensity of many of these Adn-Fc molecules had been previously characterized at low concentration (1 mg/ml) under accelerated conditions of thermal stress, where three molecules (Adn-A, Adn-a, and Adn-L) were shown to have a significantly higher aggregation propensity than the others (FIG. 6A). Those molecules that demonstrated low aggregation propensity in the accelerated stability study were scaled up and concentrated by ultrafiltration, and the levels of soluble high molecular weight (HMW) were measured by SEC at elevated protein concentration. These experiments identified two additional molecules Adn-B and Adn-b with significantly higher aggregation propensity compared to the others (FIG. 6B).

Figure 6C:
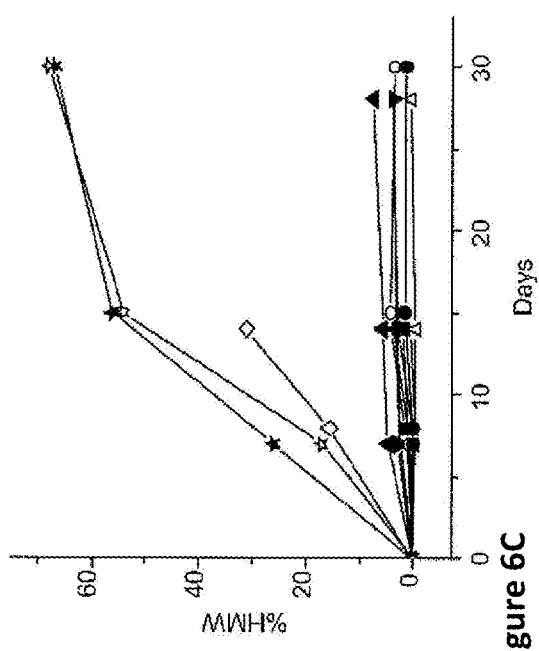
Figure 6D:
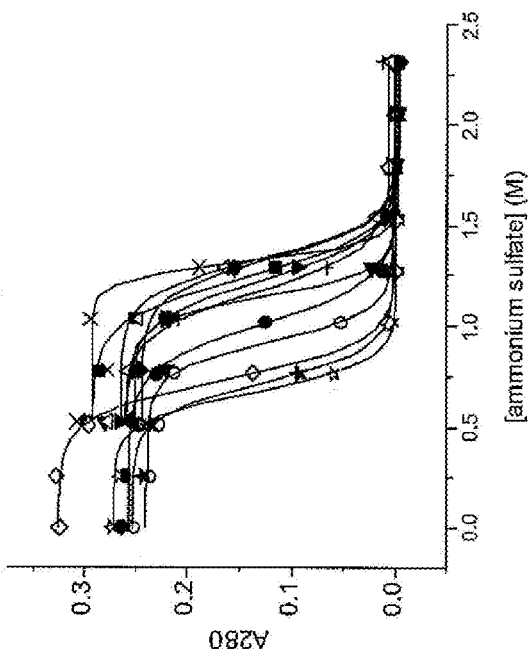

The salting out properties of the Adn-Fc molecules were characterized using the automated method, and the salting out behavior was compared to the accelerated stability and ultrafiltration data. The Adn-Fc molecules were found to salt out over a fairly broad range of [AS], with ASm values of 0.67-1.33 M (FIGS. 6C and D). Molecules produced in HEK and CHO cells had indistinguishable salting out curves (not shown). However, E. coli produced proteins were found to be of either higher (Adn-Fc-b), lower (Adn-Fc-e), or similar (Adn-Fc-a) solubility compared to mammalian-produced molecules, Adn-Fc-B, Adn-Fc-E and Adn-Fc-A respectively (FIG. 6D). The three molecules (Adn-Fc-A, Adn-Fc-a, Adn-Fc-L) with the highest aggregation propensity in the accelerated stability studies, also had the lowest ASm values (ASm=0.67-0.76 M). Adn-Fc-B and Adn-Fc-b also had lower AS solubility (ASm=0.94-1.03 M) compared to the other molecules tested (ASm=1.15-1.33 M), which is consistent with the higher aggregation levels observed for these molecules at higher protein concentrations. Therefore, the AS solubility assay was able to rapidly identify the same "high aggregation propensity" Adn-Fc molecules that were identified in the accelerated stability and ultrafiltration studies.

Solubility of dAb-Fc Fusions:

To determine if the AS solubility method was predictive of the relative solubility of protein therapeutics other than adnectins, a series of domain antibody Fc-fusion (dAb-Fc) molecules were tested using the automated method. The dAbs were from several different sequence families with binding loops specifically selected to bind different therapeutic targets. The nomenclature for these molecules includes an identifier for the sequence family (ex. "3" in dAb3-1) as well as for the specific sequence variant within the family (example, "1" in dAb3-1). The dAb molecules were produced as fusions to either human IgG4 Fc domain containing a hinge stabilizing S228P mutation (Newman, R. et al., 2001, Clin Immunol. 98, 164-74) (referred to as IgG4), or fused to one of several modified human IgG1 Fc domains which are identified with asterisks, for example IgG1*, IgG1, IgG1*, etc. Many of these dAb-Fc molecules (dAb3, dAb5, dAb6, dAb9 families) could be purified as stable monomers as judged by SEC-MALS (not shown) or DLS (FIGS. 7B and C), whereas other families demonstrated undesirable properties including higher aggregation (dAb2 and dAb8 families) (FIGS. 7B and C), and/or interaction with several different analytical SEC columns (dAb2, dAb8 and dAb9 families).

Figure 7A:
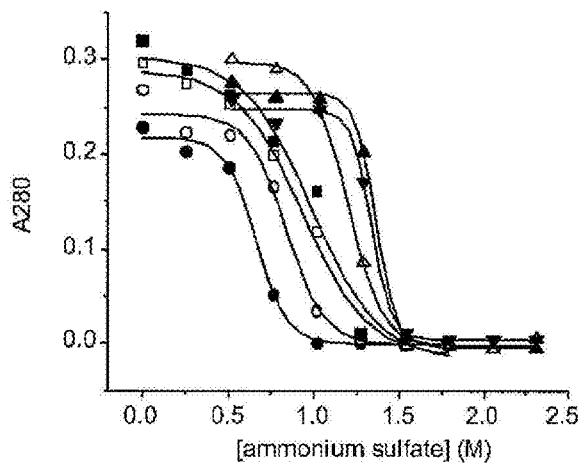
FIGS. 7A-7C. Solubility and oligomeric state of dAb-Fc molecules.
Figure 7B:
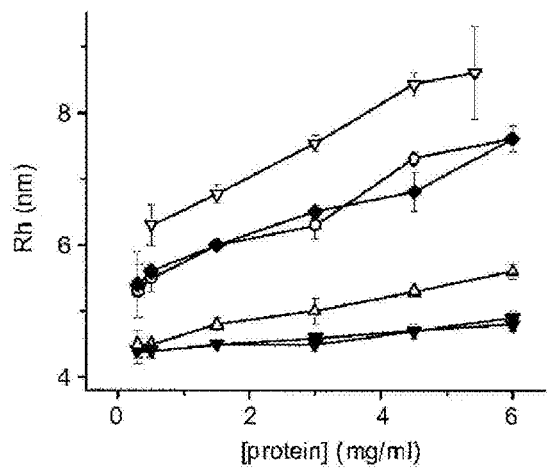
Figure 7C:
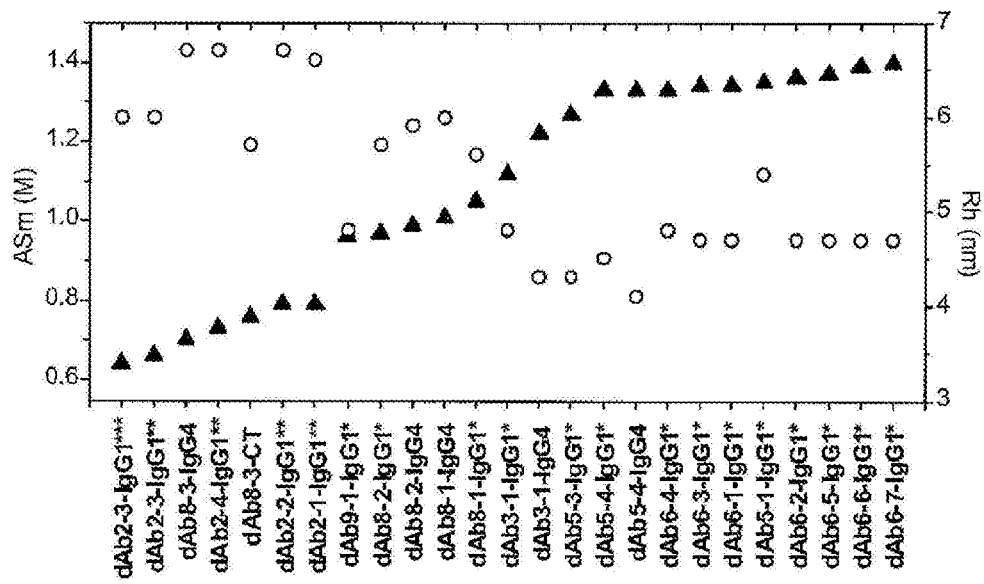
Figure 8:
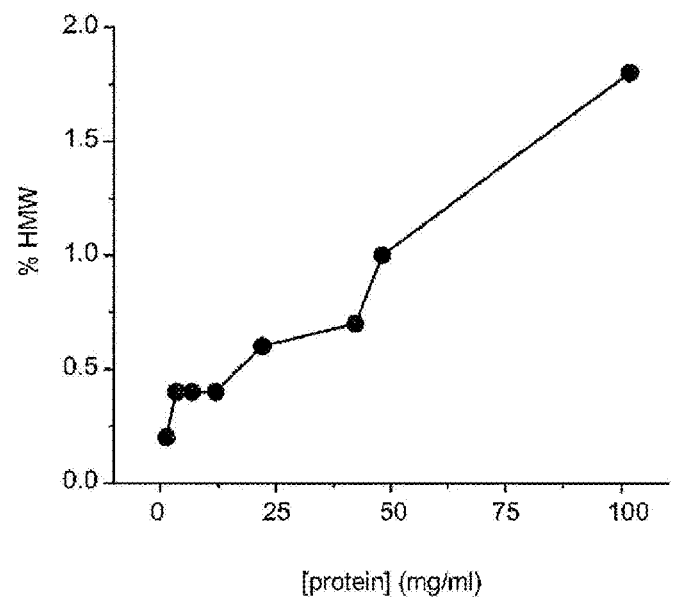
FIG. 8. % HMW for dAb-5-5-IgG1* at elevated protein concentrations as determined by analytical SEC.

Example salting out curves for representative dAb-Fc molecules are shown in FIG. 7A, protein concentration-dependent hydrodynamic radius (Rh) data for selected molecules is shown in FIG. 7B, and the ASm values are compared to the Rh measured at 1 mg/ml protein concentration in FIG. 7C. Like the Adn-Fcs described above, the dAb-Fcs were found to have a wide range of salting out properties, with ASm values of 0.64-1.40 M. Comparing the data for molecules containing the same dAb but different Fc domains (dAb3, dAbS and dAb8 families) shows that the salting out properties are primarily dependent on the identity of the dAb domain and largely independent of the Fc domain (FIG. 7C). The monomeric dAb-Fc molecules from the dAb3, dAbS and dAb6 families had the highest a ASm values (1.11-1.40 M), including the seven molecules from the dAb6-Fc family (ASm=1.33-1.40 M) which had high sequence identity (98.6-99.7%) and very similar biophysical properties. On the other hand, all of the dAb-Fc molecules from the dAb2, dAb8 and dAb9 families which demonstrated higher aggregation and/or "stickiness" toward analytical SEC columns, were found to have lower ASm values (0.64-1.05 M) (FIG. 7C). One of the monomeric dAbs-Fcs with favorable AS solubility (dAb5-4-IgG1*) was produced at large scale to generate sufficient material for ultrafiltration solubility studies, and the low aggregation propensity was confirmed, with less than 2% HMW species observed at concentrations as high as 100 mg/ml (FIG. 8).

Figure 9:
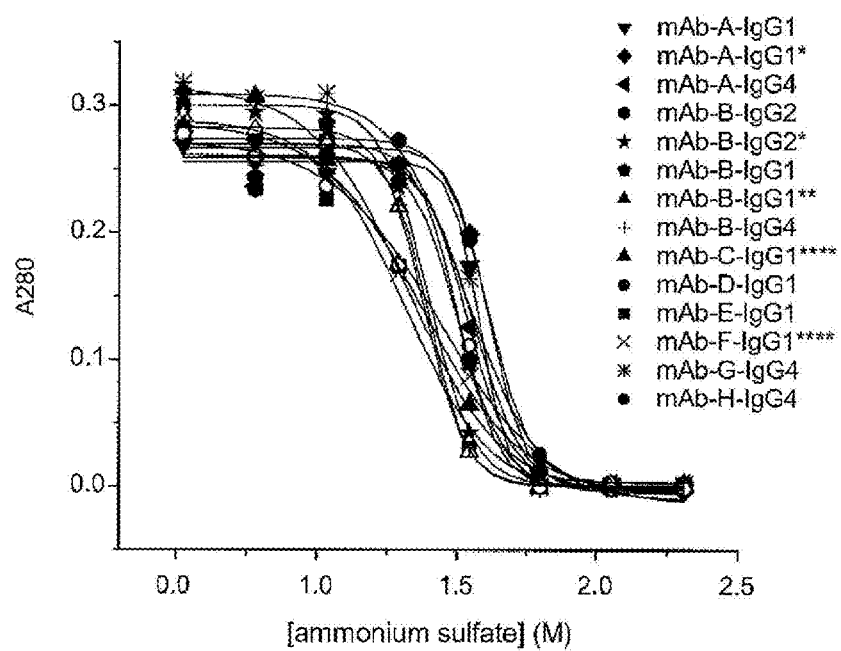
FIG. 9. Example salting out data for mAbs with different Fc domains or different Fab domains.

Solubility of Monoclonal Antibodies:

The AS solubility of a panel of monoclonal antibodies (mAbs) were tested which had either the same Fc domain but different target binding Fab domains, or the same Fab domains fused to different Fc domains. The Fc domains in this sample set included wild type IgG1, various modified IgG1 Fc domains (IgG1*, IgG1, IgG1*), IgG4-S228P (identified as IgG4), IgG2a, or a modified IgG2a (identified as IgG2a*). The salting out data for the mAbs is shown in FIG. 9, and the ASm values and Fab/Fc identifiers are listed in Table 2. Compared to the adnectins, Adn-Fcs and dAb-Fcs, the mAbs were all found to salt out over a narrower AS range, with ASm values of 1.31-1.62 M. Despite this narrow range there were clear and reproducible differences in solubility of different molecules, which were largely dependent on the identity of Fab domains, and less dependent on the Fc domain. For example, the ASm values for mAb-A having 3 different Fc domains were all 1.54-1.62 M, and mAb-B having 5 different Fc domains were all 1.38-1.51 M (Table 2). This implies that mAb aggregation may be driven by self-association of the Fab domains and likely the target binding CDRs which are the most variable regions of these molecules.

Application of Ammonium Sulfate Solubility Assay in Drug Optimization:

As described herein, an Alanine scanning approach was used to examine the contribution of binding loop residues to the interaction energy for an adnectin binding to the EGFR receptor (referred to as EGFR #8, comprising a $^{10}$Fn3 domain of SEQ ID NO:67). All residues in the BC, DE and FG target binding loops were individually replaced with Ala, and the effects on target binding were evaluated. In addition, one residue adjacent to the DE loop, T58, was also identified based on molecular modeling as a site at which binding energy might be modified through mutation. Thus three additional mutants (T58→E, T58→D, T58→Q) were created and studied for target binding. Those Ala and T58 mutants were also tested to determine whether any of the mutations could enhance the solubility of EGFR #8.

Figure 10:
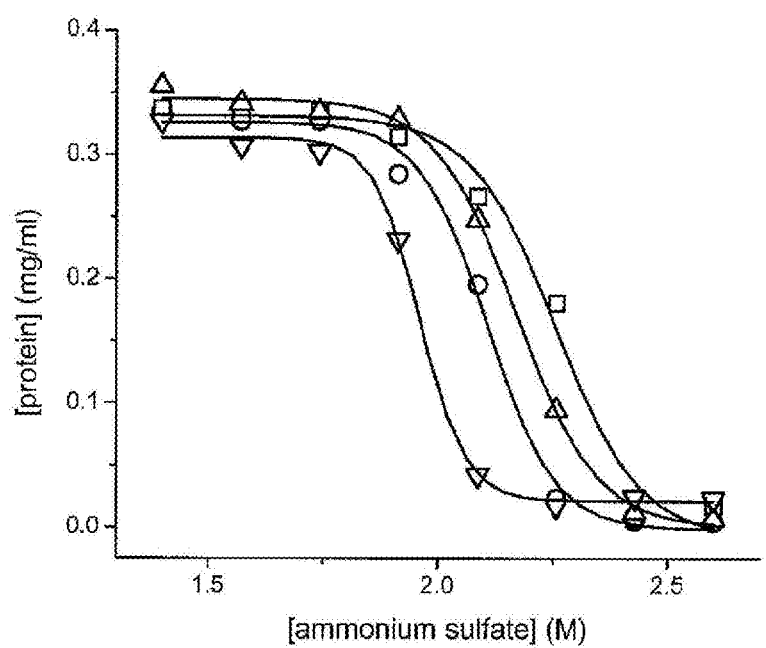
FIG. 10. Example salting out data anti-EGFR adnectin mutants. Symbols represent the data for wild type EGFR #8, $AS_m$=2.11 M (open circle ○), and mutants V54→A, $AS_m$=2.25 M (open square □), T58→E, $AS_m$=2.17 M (open up-triangle Δ), and D77→A, $AS_m$=1.96 M (open down triangle ▽).
Figure 11A:
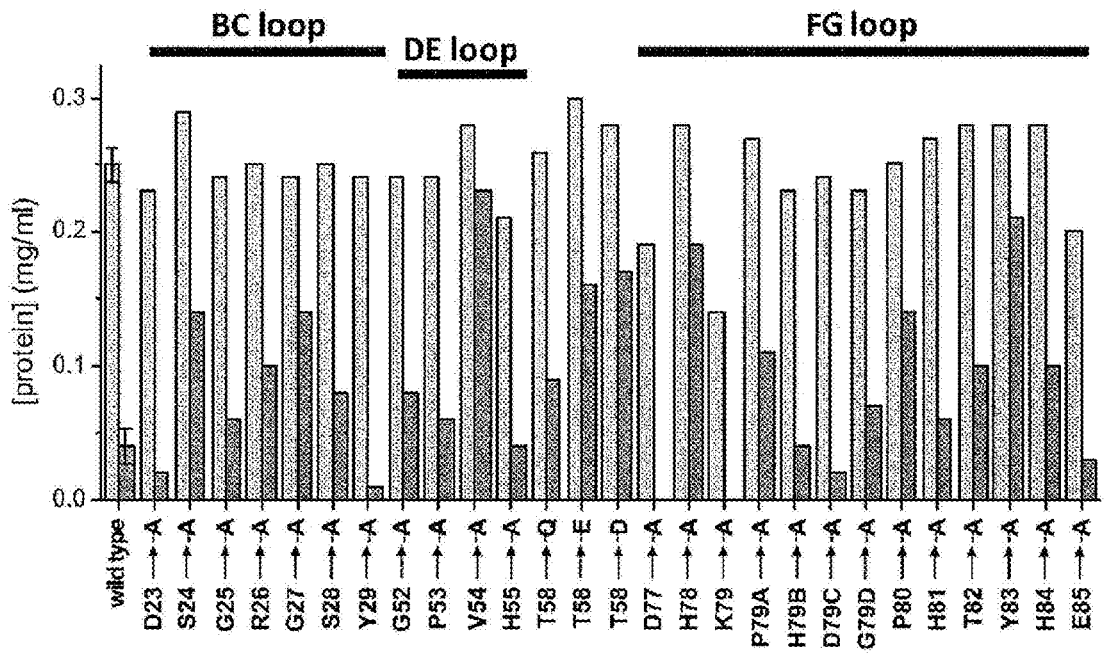
FIGS. 11A and 11B. Measured and predicted solubility of EGFR #8 adnectin mutants.

Wild type EGFR #8 Adnectin (SEQ ID NO:67), tested at 0.33 mg/ml, was found to salt out between ~1.9-2.3 M AS, with ASm=2.1 M (FIG. 10). Initial studies with selected mutants indicated that the mutants generally salted out over a similar range as the wild type protein. Therefore, to rapidly screen the mutants with minimal protein consumption, each protein was only tested at an [AS] near the onset (2.0 M), and near the base (2.2 M) of the salting out transition for wild type EGFR #8, where the data at 2.0 M could report primarily on molecules with reduced solubility, and the data at 2.2 M could identify molecules with higher solubility. This experiment identified mutants with lower solubility such as D77→A, K79→A, and E85→A, and mutants with higher solubility including S24→A, G27→A, V54→A, T58→E, T58→D, H78→A, P80→A, and Y83→A, as compared to wild type EGFR #8 Adnectin (FIG. 11A). The trends in solubility for a subset of these molecules were confirmed by generating complete titration curves (FIG. 10). The mutations which decreased solubility were generally those of hydrophilic residues such as Asp, Glu or Lys to Ala, whereas those that improved solubility were generally mutations of more hydrophobic residues to Ala, or introduction of a hydrophilic Glu or Asp residue in place of T58.

Figure 11B:
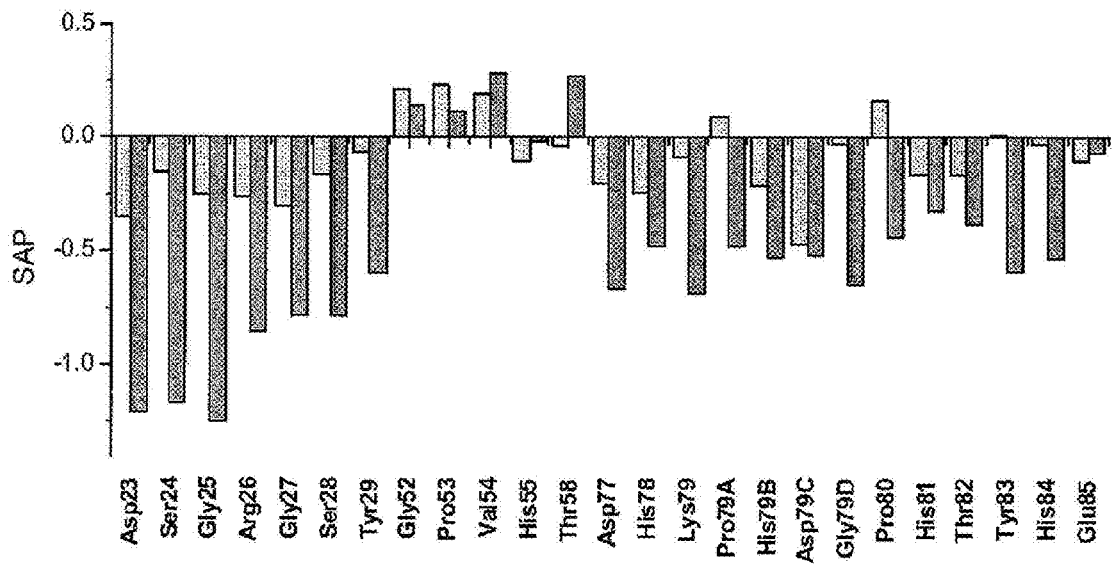

Since the structure of EGFR #8 was determined, the residue-specific aggregation propensities were calculated for all mutated residues in the protein using the "spatial-aggregation-propensity" (SAP) algorithm (Chennamsetty, N. et al., 2009, Proc. Natl. Acad. Sci. USA. 106, 11937-42). SAP values were calculated at high resolution using a radius of 5 Å to identify specific aggregation-prone residues, as well as at low resolution with R=10 Å to identify larger aggregation-prone hydrophobic patches. The SAP data for the mutated residues are shown in FIG. 11B. While the majority of the adnectin was found to be highly hydrophilic (negative SAP values), the DE binding loop is predicted to have a moderate hydrophobic character (positive SAP values) and potentially prone to aggregation. Of the residues in this hydrophobic patch, the mutations that were predicted to reduce hydrophobicity and thus aggregation the most (e.g. V54→A, T58→E and T58→D), did indeed significantly increase the solubility of EGFR #8 in the AS solubility assay (FIG. 11A and FIG. 10). The measured solubility data also identified additional mutations such as H78→A or Y83→A at which solubility could be enhanced by mutation, which was not predicted by SAP alone. In view of the structure-based target binding data (Example 2), some of the solubility-enhancing mutations (V54→A, H78→A, Y83→A) resulted in undesirable reductions in affinity/potency, likely due to the removal of important hydrophobic interactions with the EGFR target protein. However, some other solubility-enhancing mutations (S24→A, G27→A, T58→E, and T58→D) resulted in unchanged or improved binding/potency, suggesting that these mutations may be useful modifications to optimize both the solubility and potency of the Adnectin.

TABLE 1

Summary of experimental data and theoretical properties of anti-EGFR adnectins.

| EGFR Adnectin | ASm (M)[1] | Conc (mg/ml) | Rh (nm)[2] | Conc (mg/ml)[3] | Rh (nm)[2] | Tm (° C.)[4] | "GRAVY" score Hydropathy[5] | Theoretical pI | Theoretical charge at pH 7 |
|---|---|---|---|---|---|---|---|---|---|
| EGFR#1 | 1.85 | 0.9 | 1.7 ± 0.1 | 33 | 2.3 ± 0.2 | 71 | −0.58 | 5.9 | −4.2 |
| EGFR#2 | 1.64 | 1.0 | 1.9 ± 0.1 | 22* | 5.9 ± 0.7 | 59 | −0.54 | 6.2 | −2.3 |
| EGFR#3 | 1.34 | 1.1 | 1.8 ± 0.5 | 14* | 2.5 ± 1.5 | 82 | −0.57 | 6.0 | −3.3 |
| EGFR#4 | 0.67 | 0.6 | 1.9 ± 0.1 | 4.9* | 3.0 ± 0.1 | 77 | −0.50 | 5.4 | −6.3 |
| EGFR#5 | 1.45 | 1.4 | 2.0 ± 0.1 | 40 | 4.4 ± 0.0 | 78 | −0.43 | 5.9 | −3.4 |
| EGFR#6 | 2.01 | 0.9 | 1.9 ± 0.0 | 36 | 2.5 ± 0.0 | 74 | −0.56 | 5.9 | −4.2 |
| EGFR#7 | 1.53 | 1.2 | 1.7 ± 0.1 | 35 | 2.7 ± 0.1 | n.d.[6] | −0.48 | 5.9 | −4.2 |

[1]at protein concentration of 0.28 mg/ml.
[2]Rh determined by dynamic light scattering
[3]values with an asterisk (*) indicate an apparent solubility limit
[4]Tm = melting temperature
[5]GRAVY hydropathy score calculate for variable target binding loop residues. All scaffold residues were identical in each adnectin.
[6]not determined

TABLE 2

ASm values for mAbs having different Fab or Fc domains.

| Antibody | Fab | Fc | ASm[1] |
|---|---|---|---|
| mAb-A-IgG1 | A | IgG1 | 1.59 ± 0.01 |
| mAb-A-IgG1* | A | IgG1* | 1.62 |
| mAb-A-IgG4 | A | IgG4 | 1.54, 1.56 |
| mAb-B-IgG1 | B | IgG1 | 1.50 |
| mAb-B-IgG1** | B | IgG1** | 1.38 |
| mAb-B-IgG2 | B | IgG2 | 1.51 |
| mAb-B-IgG2* | B | IgG2* | 1.40 |
| mAb-B-IgG4 | B | IgG4 | 1.40 |
| mAb-C-IgG1**** | C | IgG1**** | 1.32, 1.33 |
| mAb-D-IgG1 | D | IgG1 | 1.61 |
| mAb-E-IgG1 | E | IgG1 | 1.31 |
| mAb-F-IgG1**** | F | IgG1**** | 1.38 |
| mAb-G-IgG4 | G | IgG4 | 1.53 |
| mAb-H-IgG4 | H | IgG4 | 1.43 ± 0.05 |

[1]ASm values for experiments performed three or more times are represented average ± standard deviation.

Example 2

Structure of Adnectin/Protein Complex

Adnectins that specifically bound epidermal growth factor receptor (EGFR) or interleukin 23 (IL-23), two therapeutically-validated targets, were generated using the mRNA display technique described previously (Xu et al., 2002, Chem. Biol. 9, 933-942). These Adnectins inhibit the binding of their target to the target's cognate receptor or ligand and also block intracellular signaling of the target/ligand interactions in cell-based assays. A representative Adnectin that blocked each target was selected for co-crystallization with its target to identify the nature of the contacts.

Analysis of the structures of EGFR- and IL-23-binding Adnectins yields multiple insights into the molecular interactions between $^{10}$Fn3-based variants and their targets. Many of the diversified loop residues contact the target. More interestingly, not all the residues in the three diversified loops (FIG. 12C) were at or near the 10 Fn3-based domain/target interface. Conversely, several wildtype residues outside of the diversified loops interact with the target protein. Main chain conformations of the two target-binding Adnectins and wildtype $^{10}$Fn3 were similar, but conformations of the three diversified loops and the N-terminus were different from wildtype to facilitate binding to the respective target protein's surface.

Experimental Procedures

Adnectin Selection

Initial Adnectin binders against EGFR and IL-23 were obtained using PROfusion (Xu et al., 2002, Chem. Biol. 9, 933-942; Getmanova et al., 2006, Chem. Biol. 13, 549-556), also known as mRNA display. Starting $^{10}$Fn3 libraries were designed to randomize the underlined positions indicated in FIG. 15A using trimer phosphoramidites (Glen Research). All positions were randomized with a mix of trimers representing 10% Tyr and equal amounts of all the other amino acids except Trp, Phe, and Cys, which were omitted from the mix. Subsequent screening identified a parental anti-EGFR Adnectin and a parental anti-IL-23 Adnectin of interest. The parental anti-EGFR Adnectin contained an R30Q mutation, a position that was not randomized in the original library design. Optimization libraries based on the parental leads were then generated where each loop was re-randomized with the above mix of codons while holding the other two loops constant. PROfusion was conducted on these single loop libraries until binding to the targets was recovered, and then the randomized loops were recombined followed by additional rounds of PROfusion with lower target concentrations to obtain Adnectin 1 (SEQ ID NO:67, EGFR #8 in Example 1) and Adnectin 2. Adnectin 1 contains an FG loop that is five amino acids longer than that of 10Fn3, which was not included in the optimization library design. Both the initial R30Q mutation and the longer FG loop length most likely were generated due to either errors during the PCR steps of PROfusion or in oligonucleotide synthesis.

Purification and Activity Assays.

Expression and Purification of anti-IL-23 and anti-EGFR Adnectins was analogous to that described previously (Mamluk et al., 2010, mAbs 2, 199-208). Inhibition of EGFR and IL-23 activities by these proteins was measured by competition ELISA binding assays of Interleukin-23 and native IL-23 receptor (IL-23R). Nunc Maxisorp plates (Thermo Fisher Scientific, Denmark) coated overnight with 50 μL Recombinant human IL-23R-Fc (R&D Systems, Minneapolis, Minn.), 4 μg/mL in PBS at 4° C. Plates were washed with PBS containing 0.05% w/v Tween-20 using an automated plate washer (Biotek, VT). OptEIA buffer (BD Bioscience, CA) was used as blocking agent and assay diluent. Adnectin dilutions ranging from 28 pM to 200 nM were pre-incubated with 1 nM IL-23 for an hour prior to transfer to blocked IL-23R-Fc coated plates. After a 30 minute incubation bound IL-23 was detected via anti-IL-23 (GeneTex, CA) and anti-mouse-HRP (R&D Systems, MN) followed by TMB (3,3',5,5'-tetramethylbenzidine) (BD Bioscience, CA) addition. Percent inhibition was calculated by using a known IL-23 Adnectin neutralizing standard to define 100% inhibition and a non-binding Adnectin standard as a negative control. $IC_{50}$s were generated from the average of four runs with an in-house curve fitting application. Adnectin inhibition of phosphorylation of EGFR on tyrosine 1068 was determined using an H292 cell in vitro ELISA assay as described elsewhere (Emanuel et al., 2011, mAbs 3, 38-48).

Surface Plasmon Resonance (SPR) Determination of Adnectin Binding Constants.

The $K_D$ for Adnectin 2 was determined by surface plasmon resonance (SPR) on a Biacore T100 instrument (GE Healthcare, Piscataway, N.J.), by injecting a concentration series of the Adnectin over three densities of immobilized human IL-23 in single cycle kinetics mode without regeneration of the surface.

The $K_D$ for Adnectin 1 binding to recombinant EGFR-Fc (containing amino acids 25 to 645 of human EGFR ectodomain, R&D Systems) captured on mouse anti-human IgG antibody (GE Healthcare) was assessed by SPR. Anti-human IgG was immobilized on flow cells 1-4 of CM5 sensor chips according to the manufacturer's instructions to an average of 7500-10000 RU. All kinetic measurements were conducted in HBS-P (10 mM HEPES, 150 mM NaCl, 0.05% Surfactant P20) at 37° C. with 3 M MgCl2 as regeneration solution. Kinetics of Adnectin-EGFR association were monitored for 250 seconds followed by dissociation for up to 3000 seconds with Adnectin concentrations of 0.78-100 nM. Kinetic parameters for both were calculated using Biacore T100 software.

Expression and Purification of Human IL-23.

A bi-cistronic construct for expressing the p40 and p19 subunits of IL-23 was created by cloning the p19 subunit into pFastBac Dual vector (Invitrogen) under control of the PpH promoter and the p40 subunit using hp19-pFastBac Dual under control of the Pp10 promoter. Human IL-23 was expressed in Sf9 cells which secreted the IL-23 protein into the growth media. The media containing IL-23 was concentrated and buffer exchanged into either PBS or Tris-buffered saline using tangential flow filtration. Active IL-23 was affinity purified from this concentrate by means of a novel Adnectin affinity column consisting of purified anti-IL-23 Adnectin protein covalently linked via primary amine coupling to CNBr-activated Sepharose 4 Fast Flow resin (GE Healthcare) according to the manufacturer's instructions and employing an overnight linkage incubation at 4° C. Concentrated, buffer exchanged media was passed through a column packed with this affinity resin at a linear flow rate of 20 cm/hr. The column bed was washed with five column volumes of buffer alone. Highly purified IL-23 was eluted with 0.1 M acetate, pH 4.0, 1.0 M NaCl and the eluate was immediately pH neutralized with 1/10 volume Tris HCl, pH 8.0. The sample was further purified using a preparative scale Superdex 200 size exclusion chromatography (SEC) column equilibrated and run in HBS buffer.

Purification of EGFR.

Human EGFR (residues 1-642) with a C-terminal His-tag was expressed in Sf9 cells. The secreted media containing human EGFR was concentrated and buffer exchanged into 25 mM Tris-HCl, pH 8.0, 250 mM NaCl, 5% (v/v) glycerol using tangential flow filtration. The human EGFR was purified by Ni-NTA chromatography followed by size exclusion chromatography on a Superdex 200 column (GE Healthcare) and fractions corresponding to the EGFR monomer were combined.

Preparation and Purification of EGFR/Adnectin 1 and IL-23/Adnectin 2 Complexes.

Human EGFR was mixed with anti-EGFR Adnectin at a 1:6 molar ratio and incubated on ice for 2 hours. A 1:1 EGFR: Adenectin-1 complex was purified using SEC on a Superdex 200 column equilibrated and run in 25 mM HEPES, pH 7.5, 200 mM NaCl. Purified complex was concentrated using a Vivaspin 5 kDa cutoff concentrator to 20 mg/mL.

Human IL-23/Adnectin 2 complex was purified analogously with the following modifications using IL-23 purified as described above: IL-23 and Adnectin-2 were mixed at 1:3 molar ratio and incubated overnight at 4° C.; the final complex was concentrated to 12 mg/mL.

Crystallization of Protein Complexes.

EGFR/Adnectin-1 complex was crystallized at 20° C. using hanging drop vapor diffusion method by mixing 1 μL of protein complex with 1 μL of reservoir solution containing 60% Tacsimate (Hampton Research, Aliso Viejo, Calif.). IL-23/Adnectin-2 complex with a one-fold molar excess of Adnectin-2 was crystallized in the same manner at 20° C., but used 1M tri-sodium citrate, 0.2M NaCl, 0.1M Tris, pH 7.0 for Adnectin 2. The crystal quality of IL-23/Adnectin-2 complex was improved using crystal seeding.

Data Collection and Processing.

Data for the EGFR/Adnectin 1 complex were collected at beamline 21ID-G at LS-CAT at the Advanced Photon Source at Argonne National Laboratory. The wavelength used was 0.979 Å and the detector was a Rayonix MX-300. Data were indexed, integrated, and scaled with HKL2000 (Otwinowski & Minor, 1997, Methods Enzymol. 276, 307-326). Data for IL-23/Adnectin 2 were collected at beamline 17ID at IMCA-CAT at the Advanced Photon Source at Argonne National Laboratory. The wavelength used was 1.0 Å and the detector was a MAR 165 CCD. Data were indexed, integrated, and scaled with D*TREK (Pflugrath, 1999, Acta Crystallogr. D Biol. Crystallogr. 55, 1718-1725). Space group, unit cell parameters and data collection statistics for both data sets are listed in Table 7.

Molecular Replacement.

A model for the Adnectins was derived from PDB 1FNF by deleting the BC, EF, and FG loops. The model for EGFR was based on domains of 1NQL. The model for IL-23 was a structure determined in a different crystal form from those published in the literature (3DUH, 3D87). PHASER (McCoy et al., 2007, J. Appl. Crystallogr. 40, 658-674) was used for molecular replacement. When PHASER failed to find the Adnectin in the IL-23/Adnectin 2 complex, a six-dimensional search using the AMoRe translation function was successfully used (Sheriff et al., 1999, J. Appl. Crystallogr. 32, 98-101; Navaza & Vernoslova, 1995, Acta Crystallogr. Sect. A 51, 445-449; and CCP4, 1994, Acta Crystallogr. D Biol. Crystallogr. 50, 760-763).

Model Building, Refinement and Analysis.

Figure 16A:
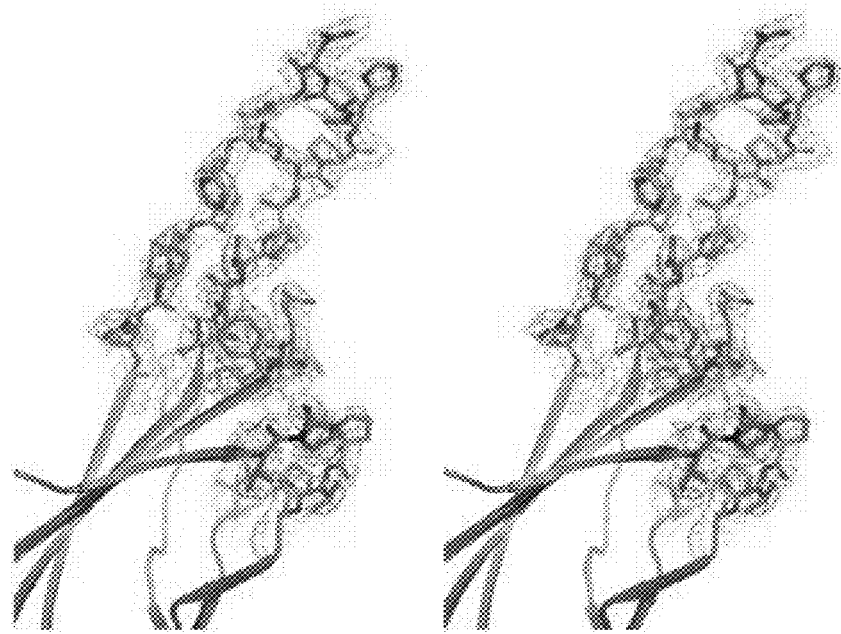
FIGS. 16A and 16B. Stereo views of the initial electron density with the final model of the diversified loops, which were not included in the initial model, of (FIG. 16A) of Adnectin 1 and (FIG. 16B) Adnectin 2.
Figure 16B:
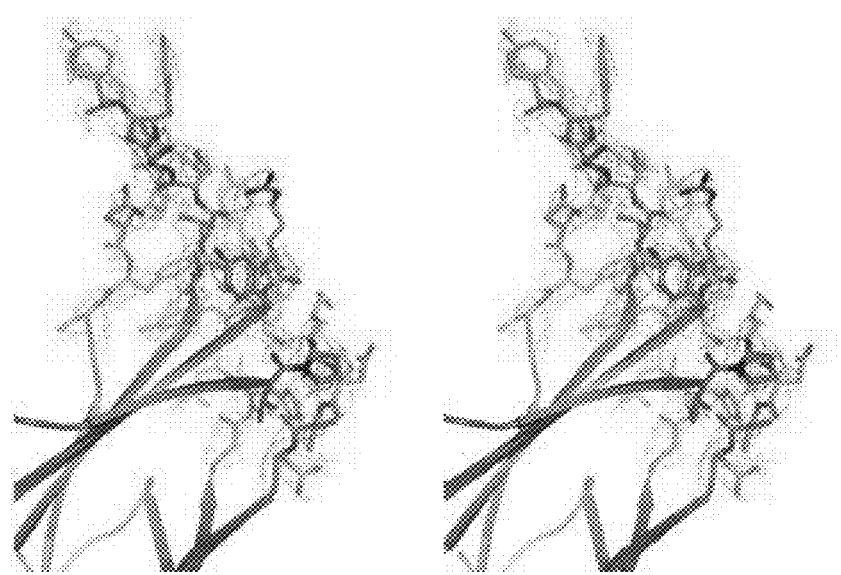

COOT (Emsley et al., 2010, Acta Crystallogr. D Biol. Crystallogr. 66, 486-501) was used for model building. Refinement was carried out with autoBUSTER (BUSTER, version 2.13.0. Cambridge, UK: Global Phasing Ltd.). Refinement statistics are listed in Table 7. Initial electron density for the diversified loops with the final model is shown in FIG. 16. Display graphics were produced with PyMOL v1.4 (Schrödinger, LLC). Buried surface area was calculated with the program MS (Connolly, 1983, J. Appl. Crystallogr. 16, 548-558) using a 1.7 Å probe sphere, contacting residues were enumerated as defined by Sheriff, 1993 (Immunomethods 3, 191-196), Sheriff et al., 1987 (J. Mol. Biol. 197, 273-296), and both use extended atomic radii as defined by Gelin & Karplus, 1979 (Biochemistry 18, 1256-1268).

Estimates of Residue Free Energies & Interaction Energies.

The atomic models of the complexes were optimized using the Protein Preparation Wizard workflow in MAESTRO 9.0.211 (Schrodinger, L L C. 2009). The estimate of Gibbs free energy was calculated as described previously (Novotny et al., 1989, Biochemistry 28, 4735-4749; Krystek et al., 1993, J. Mol. Biol. 234, 661-679) and implemented in a python script using MAESTRO (Maestro, version 9.0, Schrödinger, LLC, New York, N.Y., 2009).

Energetics Calculations

Tables 8-10 contain the calculated energies for all mutant and wild type residues. For alanine-scanning mutagenesis the interaction energies and estimates of free energy were compared to experimental values for Adnectin target binding. The change in interaction energy from wildtype to mutant is reported in Tables 3-5 along with the experimental data. For all contact residues in each complex individual homology models were created substituting all amino acids at each contact position. For each of the models energetic calculations of the interaction energy and estimates of free energy were analyzed focusing on the amino acids corresponding to contact positions within the Adnectins. The calculated values for the selected models are presented in Tables 8-10.

Estimates of Residue Free Energies & Interaction Energies.

The atomic models of the complexes were optimized using the Protein Preparation Wizard workflow in MAESTRO 9.0.211 (Schrodinger, L L C. 2009). During this process side chain protonation states, histidine tautomers and terminal Chi rotamers for histidine, asparagine and glutamine side chains are optimized. The final step in the workflow is restrained minimization of the complex (0.3 Å RMSD) which allows for subtle optimization of the complex within the OPLS 2005 force field. Protein models were created for each mutant protein using PRIME side chain refinement protocol followed by two minimization steps. The first minimization was applied to only side chains for the subset of residues that were within 5 Å of a mutation site. The final minimization step was applied to the same subset of residues but it included the backbone of the residues in the minimization.

The estimate of Gibbs free energy was calculated as described previously and implemented in a python script using MAESTRO (Maestro, version 9.0, Schrödinger, LLC, New York, N.Y., 2009). The residue interaction energies were determined using the OPLS 2005 force field as implemented in the Component Interactions script (Schrodinger, LLC) using Macromodel IMacroModel, version 9.7, Schrödinger, LLC, New York, N.Y., 2009). The script calculates the molecular mechanics interaction energy between a set of residues and outputs the individual VDW and electrostatic contribution terms. For the electrostatic component, distance-dependent dielectric was used with a constant of 4.0, similar to the free energy calculations.

Accession Numbers.

Coordinates and structure amplitudes have been deposited in the RCSB Protein Data Bank under ID codes 3QWQ (EGFR/Adnectin 1) and 3QWR (IL-23/Adnectin 2).

Results

Identification of EGFR and IL-23 Antagonistic Adnectins.

Figure 15A:
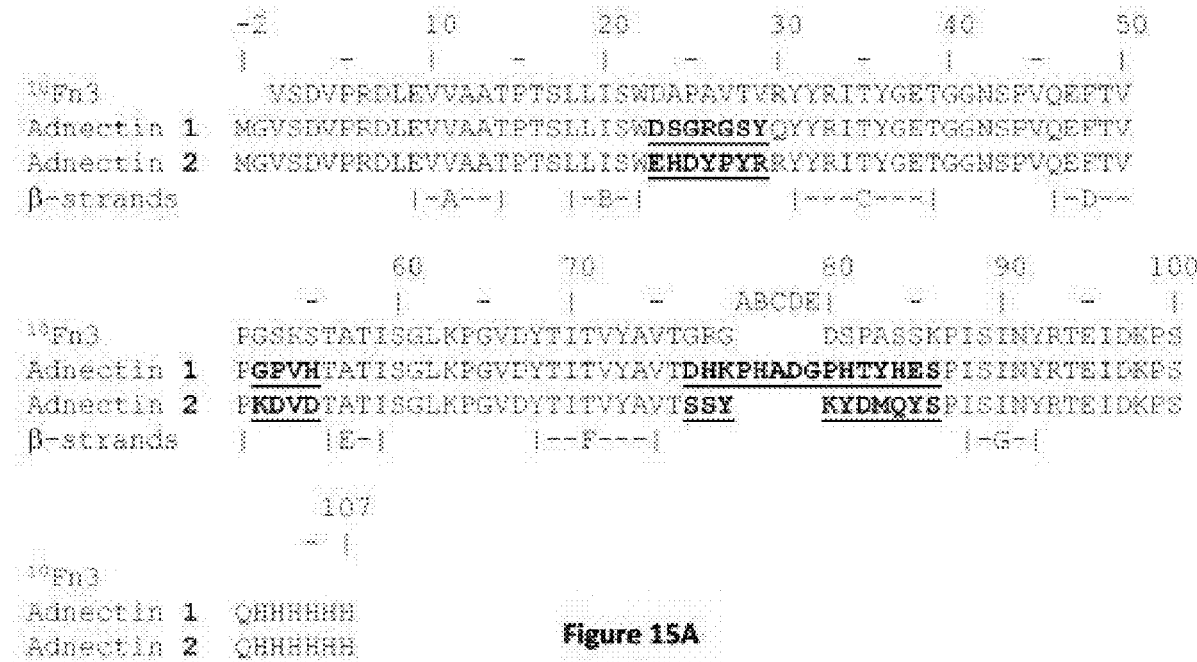
FIGS. 15A-15C. Comparison of Adnectin 1 (SEQ ID NO. 86) and Adnectin 2 (SEQ ID NO. 8) with $^{10}$Fn3 (SEQ ID NO. 14).

Adnectins that bound to and blocked activity of either EGFR (Adnectin 1) or IL-23 (Adnectin 2) were identified using the biochemical selection technique of mRNA display in which a protein was covalently attached to its coding nucleic acid sequences (Xu et al., 2002, Chem. Biol. 9, 933-942; Getmanova et al., 2006, Chem. Biol. 13, 549-556; Roberts & Szostak, 1997, Proc. Natl. Acad. Sci., USA 94, 12297-12302) (FIG. 15A and Experimental Procedures). Adnectin 1 bound the EGFR ectodomain Fc fusion with a 2 nM $K_D$ and inhibited EGF-induced EGFR phosphorylation in H292 cells with an $IC_{50}$ of ~50 nM. Adnectin 2 bound immobilized IL-23 with a 2 nM $K_D$ and competed with the IL-23/IL-23R interaction with an $IC_{50}$ of 1 nM in a biochemical receptor binding competition assay. Adnectin 1 was co-crystallized with EGFR and Adnectin 2 was co-crystallized with IL-23 to determine the structural basis of these activities.

Overview of the Structure of the EGFR/Adnectin 1 Complex.

Figure 17A:
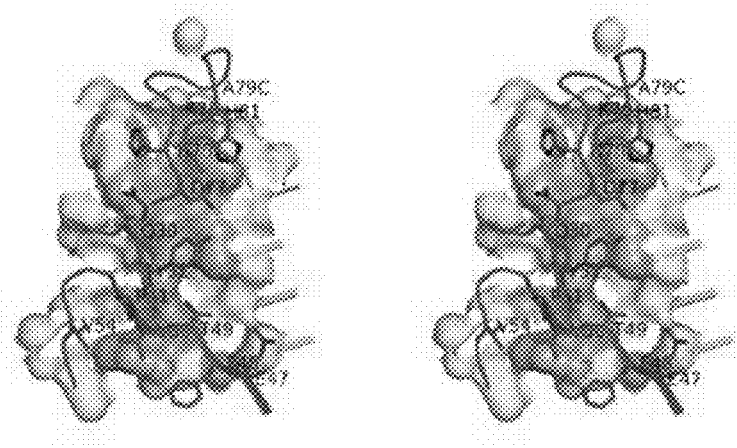
FIGS. 17A and 17B. Stereo views of parts C (FIG. 17A) and D (FIG. 17B) of FIG. 13. Both figures rotated 90° in z from their representation in FIG. 13 to accommodate an interocular distance of ~60 mm for stereo viewing.
Figure 17B:
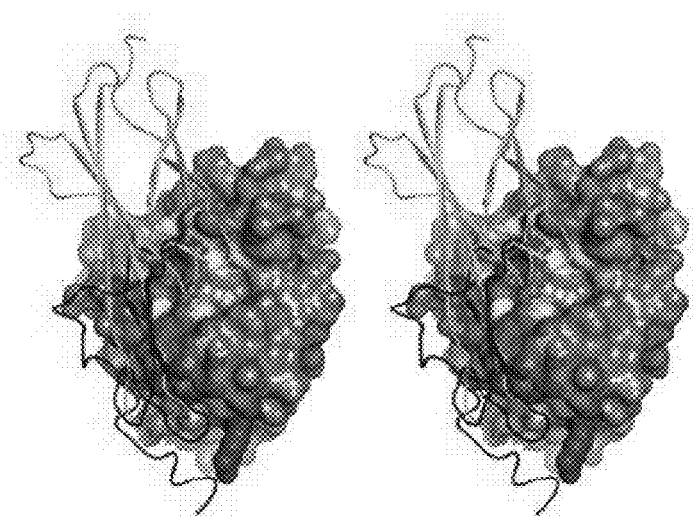

EGFR is a remarkably flexible molecule with differing interactions between the four domains. EGFR structures deposited in the PDB (1IVO, 1NQL, 1YY9) show that domains I and III are relatively rigid while parts of domains II and IV may adopt multiple conformations that orient domain III differently with respect to domain I (Ogiso et al., 2002, Cell 110, 775-787; Ferguson et al., 2003, Mol. Cell 11, 507-517; Li et al., 2005, Cancer Cell 7, 301-311). The structure of EGFR in the EGFR/Adnectin 1 complex most closely resembled 1NQL, which is a complex of EGFR with EGF at low pH and is considered to be an inactive form of the receptor. However, superimposition of domain I of the two complexes leads to centers of domain III of the two complexes being separated by ~25 Å, showing once again the remarkable flexibility of EGFR. The Adnectin bound to EGFR domain I (FIG. 13A) overlapping the binding site of EGF on EGFR domain I in either its active (1IVO) or inactive (1NQL) forms and, therefore, sterically hindered EGF binding (FIG. 13D, 17D). This site is a radically different site from antibodies that bind to EGFR on domain III. Cetuximab (1YY9) and necitumumab (3B2V) bind to essentially the same site (FIG. 13A), but are oriented differently, and matuzamab (3C09) binds to a distinct site on domain III (Li et al., 2005, Cancer Cell 7, 301-311; Li et al., 2008, Structure 16, 216-227; Schmiedel et al., 2008, Cancer Cell 13, 365-373).

Adnectin 1 described herein had an insertion of 5 residues in the FG loop. To retain a consistent numbering scheme, residues inserted in the FG loop were given insertion letters (FIG. 15A) analogous to that devised for immunoglobulins by Kabat et al., 1991 (Sequences of Proteins of Immunological Interest, $5^{th}$ ed. (Bethesda: National Institutes of Health)), and similar to that used by Gilbreth et al., 2008 (J. Mol. Biol. 381, 407-418) for the BC loop.

Specific interactions of Adnectin 1 with EGFR.

The interaction between Adnectin 1 and EGFR domain I resulted in 520 Å$^2$ on the Adnectin and ~590 Å$^2$ on EGFR domain I that were buried by the interaction (FIG. 13C, 17C). The size of these interacting surfaces was towards the smaller end typical of antibody/protein antigen interfaces (Sheriff, 1993, Immunomethods 3, 191-196). They were also smaller than those seen for other $^{10}$Fn3-based variants (Table 3; Gilbreth et al., 2008, J. Mol. Biol. 381, 407-418; Gilbreth et al., 2011, Proc. Natl. Acad. Sci., USA 108, 7751-7756; Huang et al., 2009, J. Mol. Biol. 392 1221-1231; Wojcik et al., 2010, Nature Struct. Mol. Biol. 17, 519-527), but affinities for Adnectin 1 and the antibodies surveyed were of the same order of magnitude. The relatively small size of the interaction was due to the convex surface on EGFR consisting of loops connecting the two β-sheets at one edge of a β-sandwich domain interacting with the convex surface of the Adnectin (FIG. 13C). Nevertheless, the Sc statistic (Lawrence & Colman, 1993, J. Mol. Biol. 234, 946-950), which is a measure of the complementarity of the binding surfaces, for this complex was 0.71, falling towards the lower end of the range of protease/protease inhibitors (0.71-0.76) and oligomeric interfaces (0.70-0.74) and above the range observed for antibody/antigen complexes (0.66-0.68) (Lawrence & Colman, 1993, supra) and slightly above the mean of $^{10}$Fn3-based domain/protein complexes (Table 3). This suggests that although the surface of interaction was relatively small for the Adnectin 1/EGFR complex, it was a more complementary fit than seen with antibodies and their antigens.

The principal interactions of the Adnectin occurred through the FG loop (~175 Å$^2$ of buried surface), the D strand (~175 Å$^2$), the DE loop (~70 Å$^2$), the C strand (~50 Å$^2$), and the BC loop (~40 Å$^2$) (FIG. 13C, 17C). The residues from the Adnectin with van der Waals (VDW) radii dependent contact (Sheriff, 1993; Sheriff et al., 1987a) to EGFR were: BC loop: Gln30; C strand: Tyr31; D strand: Glu47, Phe48, Thr49, Val50, Pro51; DE loop: Val54; FG loop: Asp77, His78, Lys79, Ala79C, His81 (FIGS. 13B, C, E, 17C, 18D, 18E). One feature of this interface was that the extensive interactions between the wildtype backbone sequence of the D strand in the Adnectin and the EGFR—it contributed as much surface area and as many residues as did the diversified FG loop interaction. Aromatic residues (His, Phe, Tyr) contributed ~¼ of the surface area (~120 Å$^2$) of the overall Adnectin interaction surface, but only one tyrosine (31) was involved, which was part of the Adnectin scaffold and whose side chain lay parallel to the rather flat EGFR surface. The N-terminus and most of the BC and DE loops were on the distal side of the Adnectin from the EGFR and were thus not involved in the interaction. A β-sheet like interaction occurred between Adnectin 1 and the N-terminal region of EGFR, which displayed 3 N . . . O═C hydrogen bonds and one side-chain to side-chain hydrogen bond (FIG. 13E).

Alanine-Scanning Mutagenesis of EGFR/Adnectin 1.

Single-site alanine mutants (Wells, 1991, Methods Enzymol. 202, 390-411) were made for 30 of the 101 residues of the Adnectin. All residues in the BC, DE, and FG loops that were diversified as part of the selection process were included as well as any other residue that was in contact (see above) with EGFR (Table 4, Table 8). Mutation of the following residues led to significantly diminished binding: Tyr 29, Gln 30, Tyr 31, Gly 52, Val 54, Asp 77, Lys 79, His 81, and Tyr 83. Surprisingly, Tyr 29, Gly 52, and Tyr 83 do not directly interact with EGFR. These may be explained on the basis of structural interactions within the Adnectin. Tyr29 side chain packed in the interior of the BC loop and against the F strand and mutation to Ala may be expected to disrupt the BC loop. Since Gly52 was part of a Pro-Gly-Pro turn, changing Gly to Ala might have disrupted this structural element. Tyr83 side chain formed an edge-to-face interaction with His81 side chain and a hydrogen bond with Glu85 side chain. His81 side chain in turn interacted with EGFR Thr15. The diminished activity resulted from the mutation Tyr83→Ala may be due to its helping maintain the position of His81.

Prior to the alanine-scanning mutagenesis, the energetics of the interaction was calculated on a per residue basis. These calculations correctly identified Gln 30, Tyr 31, and Asp 77 as important to the interaction, but also identified Pro 51 as being important, although mutation to Ala did not affect binding (Table 4, Table 8). The remaining residues that interacted with EGFR and were identified by alanine scanning, Val 54, Lys 79, and His 81, all showed changes in the correct direction (Table 4), but the magnitude of the change did not reach the threshold considered significant (3 kcal/mol).

Mutagenesis of Contact Residues of EGFR/Adnectin 1.

Six residues, Tyr31, Glu47, Thr49, Pro51, Thr58, and Ala79C, were targeted for additional mutation studies based upon interaction energy predictions calculated from models to explore the possibility that mutations might increase the binding affinity of Adnectin 1. Most mutations, which were typically attempts to create either hydrogen-bond or charged interactions, did not substantially change the affinity compared to the parent (Table 5, Table 9). However, the three mutations to residue 49 to increase the van der Waals interactions by converting a Thr to a Val, Ile, or Tyr, increased the affinity of the Adnectin 8-to-40 fold (Table 5, Table 9). Since the side chain of Thr49 was not in contact with EGFR, mutation to a larger side chain (Ile, Tyr) may have created additional hydrophobic contacts with residues from EGFR located in the surface depression next to Thr 49 (FIG. 13C). In the case of Thr49→Val, the substitution of a methyl for the hydroxyl which was pointing towards a hydrophobic environment, may account for the increased affinity.

Tyr 31 was mutated to Ser, Leu, and Phe to see whether the prediction that small residues (Ser) would lead to a decrease in affinity, but larger residues such as Leu and Phe, which potentially maintained VDW interactions might have a favorable effect on binding. Phe and, surprisingly, Ser had little effect, but Leu, led to much weaker binding despite modeling and energetics calculations that suggested it would be very similar to the parent.

Glu 47 side chain was not involved in interactions with EGFR, but modeling showed it to be close enough that a mutation to Arg or Lys would potentially form a salt bridge with EGFR Glu 90. Although energetics calculations suggested that this salt bridge would be favorable, experimentally neither materially affected the binding, nor did a mutation to Asp, which changed the relative position of the charge.

Pro 51 was the first residue of the DE-loop and was within VDW contact of EGFR Leu 69 side chain and the main chain carbonyl oxygen atoms of EGFR Ser 99 and Tyr 101. Modeling showed that Leu potentially improved VDW contacts or that Thr formed a hydrogen bond. Leu at position 51 was not significantly different than the parent, but Thr led to weak binding, maybe because the Pro 51-Gly 52-Pro 53 structure at the beginning of the DE-loop was disrupted.

Thr 49 side chain had no significant contacts with EGFR, but modeling suggested mutation to Ile, Val, or Tyr may allow those residues to maintain the backbone hydrogen bond and pick up additional packing interactions with EGFR residues Leu 14 and Leu 69 that form a hydrophobic surface patch. Of the three mutations Tyr was predicted to be energetically favorable compared to the parent, while Val and Ile were predicted to be similar to the parent. Nevertheless, mutation of Thr 49 to Val or Ile showed a 12 and 37-fold, respectively, increase in binding affinity while mutation to tyrosine produced an 8-fold increase in binding affinity.

Thr 58 was not in contact with EGFR in the crystal structure, but modeling suggested that replacement with an acidic residue might lead to a salt bridge with Lys 105 although the NZ atom was not placed in crystallographic model due to inadequate electron density. Despite the prediction of large favorable changes in interaction energy, none of the three substitutions (Glu, Gln, or Asp) led to any significant change in activity. However, the substitutions at this position resulted in enhanced solubility of the protein, as described herein (see Example 1).

Ala 79C was marginally in contact with EGFR, but modeling showed that a longer residue might lead to additional interactions and energetics calculations suggested considerable increase in binding affinity for five mutations (Arg, Asn, Glu, Leu, and Tyr). Nevertheless all five mutations showed a slight, but insignificant, diminution of activity.

Overview of the Structure of the IL-23/Adnectin 2 Complex.

Figure 14A:
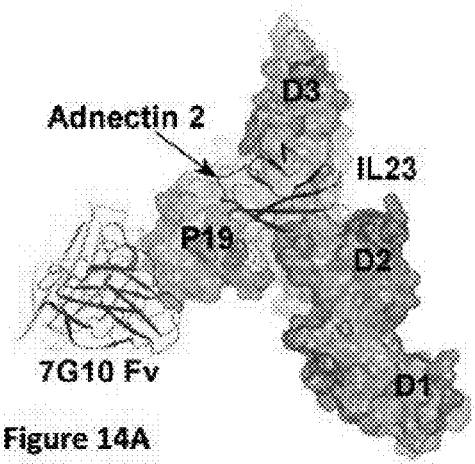
FIGS. 14A-14E. Binding of Adnectin 2 to IL-23.
Figure 14B:
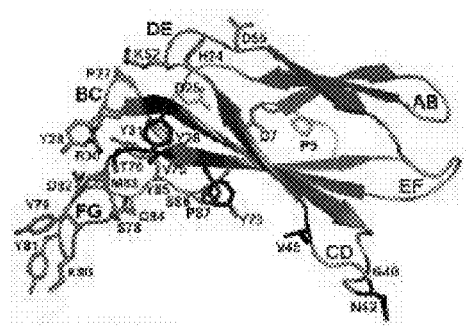

IL-23 is a two subunit protein consisting of a p40 subunit that is shared with IL-12 and a p19 subunit that is distinct from the p35 subunit of IL-12. The p40 subunit consists of three Ig-like 7 stranded β-sheet domains, while the p19 consists of a 4-helix bundle. Adnectin 2 bound at the junction of the p40 and p19 subunits making considerable interactions with both subunits including domains 2 and 3 of the p40 subunit (FIGS. 14A, C, D, E, 18C, and 18E). Despite the interactions with p40, Adnectin 2 did not inhibit IL-12 binding or signaling (data not shown). Moreover, although the diversified loops were towards the center of the interface, interactions extended along the β-strands away from the diversified loops and included the CD loop on the opposite end of the molecule. This concave site is likely inaccessible to Fvs which are much larger, consisting of two domains from separate subunits and six hypervariable loops. In fact, the Adnectin binding site was dramatically different from that of the one known antibody complex for IL-23 (PDB 3D85), which binds only to the p19 subunit (Beyer et al., 2008, J. Mol. Biol. 382, 942-955) (FIG. 14A).

Specific Interactions of Adnectin 2 with IL-23.

Figure 14C:
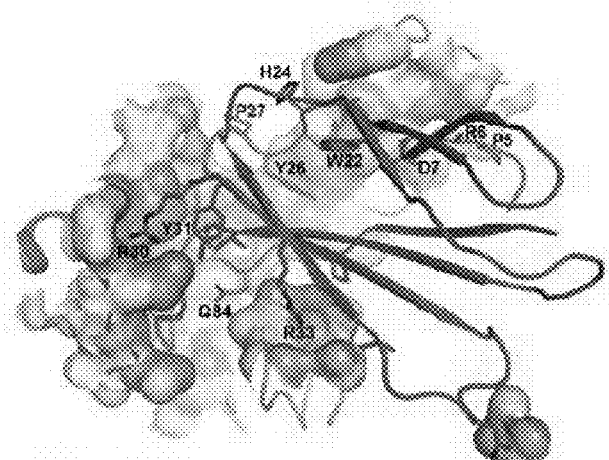
Figure 18A:
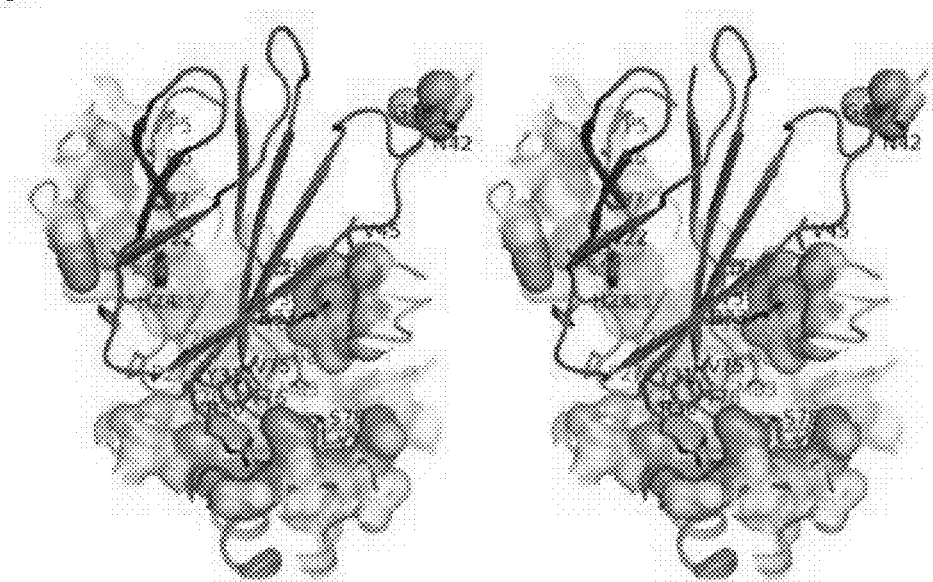
FIGS. 18A-18C. Stereo views of parts C (FIG. 18A), D (FIG. 18B), and E (FIG. 18C) of FIG. 14.
Figure 18B:
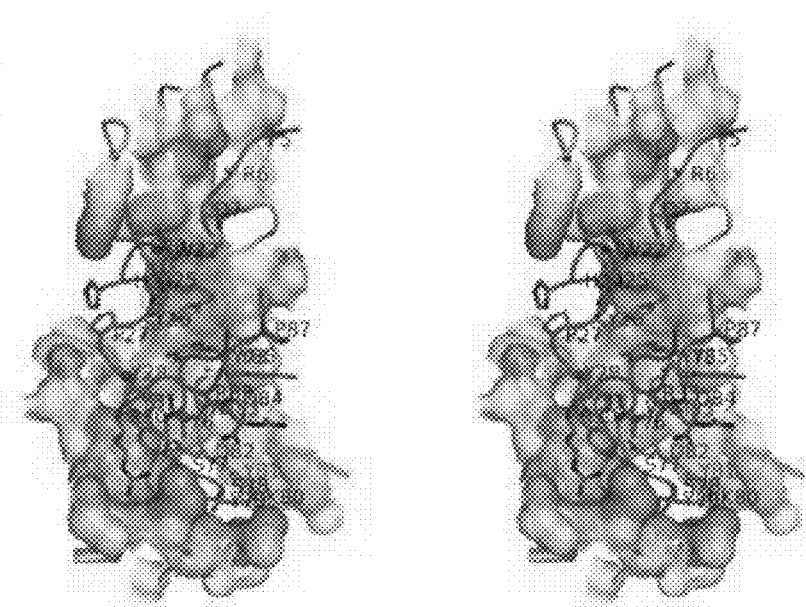
Figure 18C:
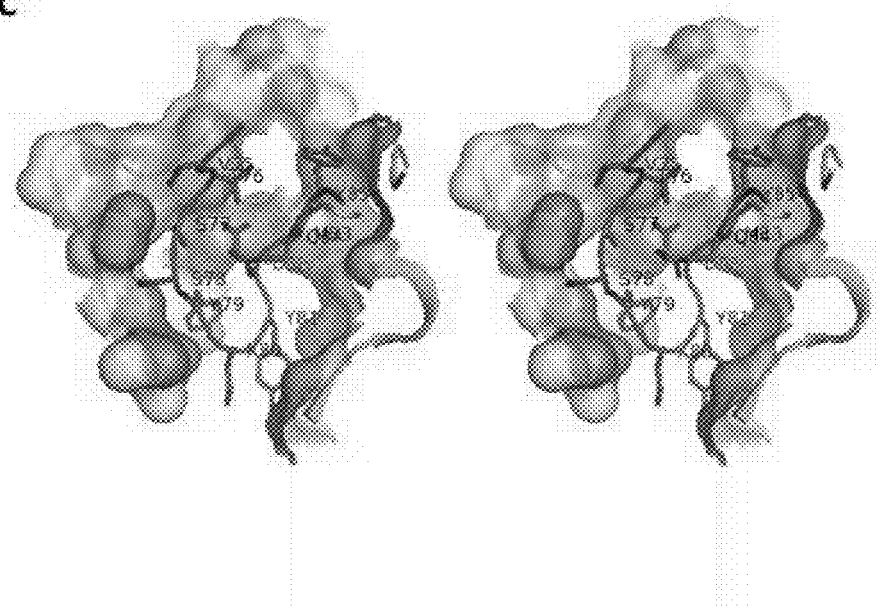

The interaction between Adnectin 2 and IL-23 was quite large, burying 1320 Å$^2$ on the Adnectin surface and ~1370 Å$^2$ on the IL-23 surface (FIGS. 14C, 18C). This amount of buried surface area was larger than most antibody/antigen interactions and, may reflect the concave nature of the binding site on IL-23. The buried surface was also much larger than for any other $^{10}$Fn3-based domain complex (Table 3). Despite the large interacting surface, the affinity of Adnectin 2 for IL-23 was the same order of magnitude as the antibodies for their protein antigens. The Sc statistic for this complex was 0.73, which suggested that it was more complementary than the antibody/antigen complexes surveyed by Lawrence & Colman, 1993 (J. Mol. Biol. 234, 946-950) and second largest of the $^{10}$Fn3-based domain/ protein complexes (Table 3).

Figure 14D:
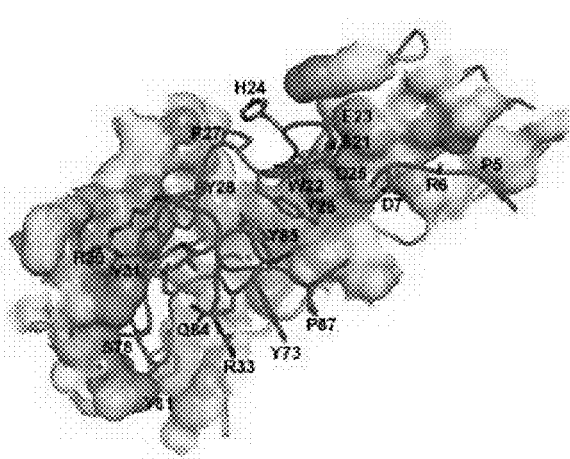
Figure 14E:
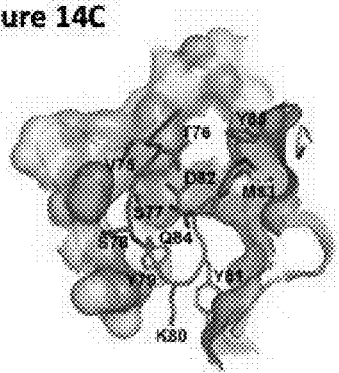

The principal interactions occurred through the FG (~610 Å$^2$) and BC (~380 Å$^2$) loops, but most segments of secondary structure had at least some surface area buried by the interaction (FIGS. 14C, 18C). The following residues from the Adnectin are found to contact IL-23: N-terminal region: Pro5, Arg6, Asp7, BC loop: Glu23, His24, Asp25, Tyr26, Pro27, Tyr28, Arg30, C strand: Tyr31, Arg33; CD loop: Gly40, Asn42, Val45; F strand: Tyr73, Val75; FG loop: Thr76, Ser77, Ser78, Tyr79, Lys80, Tyr81, Asp82, Met83, Gln84, Tyr85, Pro87 (FIGS. 14B-E, 18C-E). Four points stood out from this list. First, the number of interacting residues was large and they came from many of the β-strands and loops. Second, no contacts occurred between the diversified DE loop and IL-23. Third, a large number (7) of tyrosine residues were involved in the interaction. The frequent occurrence of tyrosine has been observed for antibodies, VH fragments, and $^{10}$Fn3-based variants interacting with antigens (Padlan, 1990, Proteins 7, 112-124; Mian et al., 1991, J. Mol. Biol. 217, 133-151; Kossiakoff & Koide, 2008, Curr. Opin. Struct. Biol. 18, 499-506; Koide & Sidhu, 2009, ACS Chem. Biol. 4, 325-334), and is presumably due to the relatively low loss of entropy due to relatively few dihedral angles that become immobilized compared to large surface area that tyrosine residues are able to contribute, which amounts to a total of ~450 Å$^2$ in this case. Moreover, several of these tyrosines (20, 79, 81, 85) appeared to fit into crevices in the IL-23 surface (FIGS. 14D-E). Fourth, a large number (11) of non-diversified residues were involved in direct interactions with IL-23. Residues in this fourth category included 2 of the 7 Tyr residues and residues at the N-terminus. Although electron density was interpretable for only part of the N-terminus, it was clear that the N-terminus did not point in the direction of the BC, DE, and FG loops as it did in the wildtype $^{10}$Fn3, but rather reversed direction and pointed towards the opposite end of the molecule.

Mutagenesis of Contact Residues of IL-23/Adnectin 2.

Four amino acids, Tyr28, Tyr73, Tyr81 and Pro87 were mutated to alanine to demonstrate that energetically important residues could be predicted. This proved to be the case for Tyr28, Tyr81, and Pro87 but not for Tyr73, which had little effect when mutated to alanine (Table 6). Tyr28 was located in the center of the BC loop and forms significant contacts with amino acids that were at the terminus of the IL-23 p19 domain A-helix, e.g. edge-to-face interactions with Trp26 and His29. Similarly, Tyr81 which was located in the center of the FG loop had significant contacts with the IL-23 p40 subunit, e.g. Ser204. Pro87, which was located at the C-terminus of the FG loop, may be required for retaining the FG loop conformation and contacted residues Gly100 and Pro101 from the IL-23 p40 subunit. Although Tyr73 was predicted to contribute ~6 kcal (Table 10) to the interaction, this was less than half that predicted for Tyr28 (~16 kcal) and Tyr81 (~13 kcal) (Table 10). In the minimized structure the Tyr73 side chain formed a hydrogen bond with IL-23 p40 subunit Lys99 carbonyl oxygen, but the Tyr73→Ala mutant showed that it was not a key energetic residue.

Interactions of Mutated Contact Residues in the IL-23/Adnectin 2Complex

Some mutations were made in an attempt to improve the affinity by specific interactions in the IL-23/Adnectin 2 complex. Four positions in ATI-000929, Thr 35, Val 45, Tyr 73, and Val 75, that were all on the same face of the β-sandwich fold (β-strands C, D, F, and G) of the Adnectin, were selected for mutagenesis in an attempt to improve the affinity through interactions with the p40 subunit (Table 6). Thr 35 and Val 45 were near each other and were mutated in an attempt to create an interaction with IL-23 p40 subunit Lys 99. At each position the same four mutations (asparagine, glutamine, aspartic acid, and glutamic acid) were made individually, in hopes of forming electrostatic interactions with Lys 99. The acidic residues were especially favored by modeling. However, no improvement in binding was seen at either position. The Thr 35→Asp mutant showed a significant decrease in binding. This may be due to unfavorable interactions that Asp 35 might have with the Adnectin Glu 49. Val 75 was mutated in an attempt to form a hydrogen bond with IL-23 p40 subunit Pro 101 carbonyl oxygen. No mutation of this residue altered binding. Tyr 73, as noted above, contacts IL-23 p40 subunit residues 99-101 as well as forming a hydrogen bond with the carbonyl oxygen of Lys 99. Modeling of Tyr 73 suggested that an arginine mutant could form an additional hydrogen bond with Glu 100 and increased contacts with IL-23 p40 subunit residues 99-101. Three mutations at this position had no effect, but Tyr 73→Gln led to a modest, ~4-fold, increase in activity.

Comparison of the Structures of Adnectin 1 and Adnectin 2 with $^{10}$Fn3.

Figure 15B:
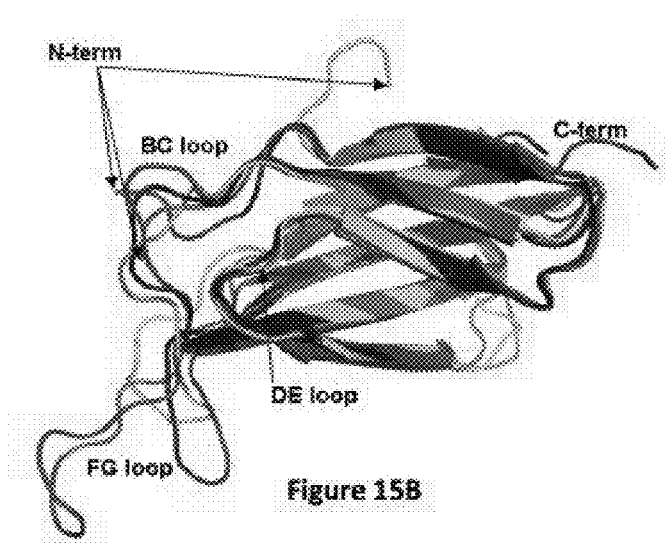
Figure 15C:
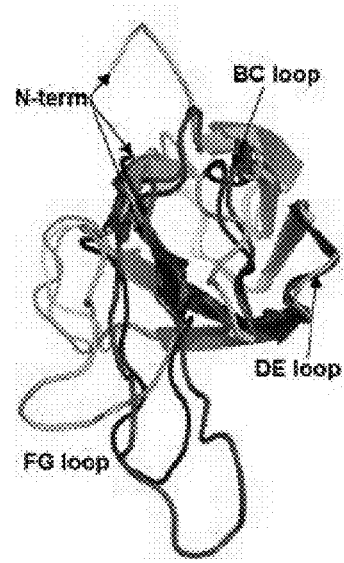
Figure 19A:
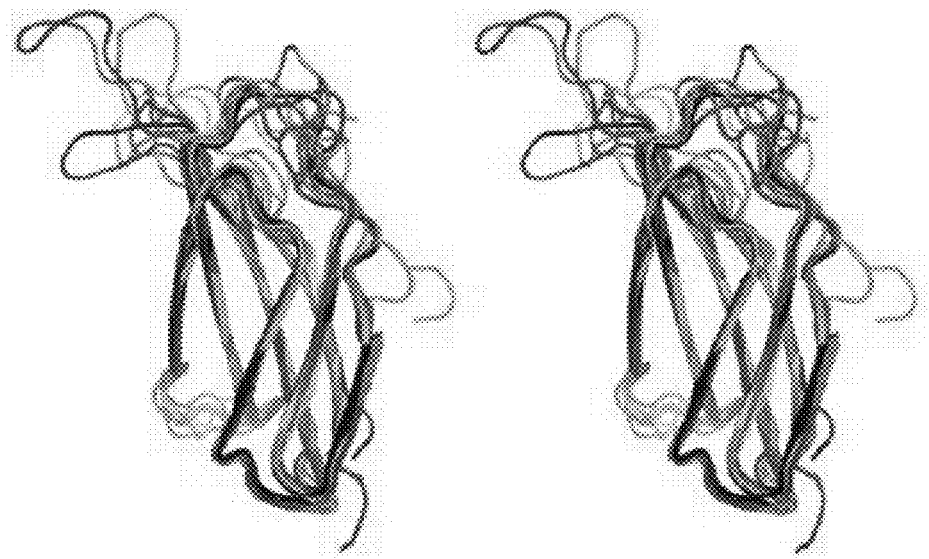
FIGS. 19A and 19B. Stereo views of the superposition of $^{10}$Fn3-based variants, related to FIG. 15, but showing additional $^{10}$Fn3-based variants.
Figure 19B:
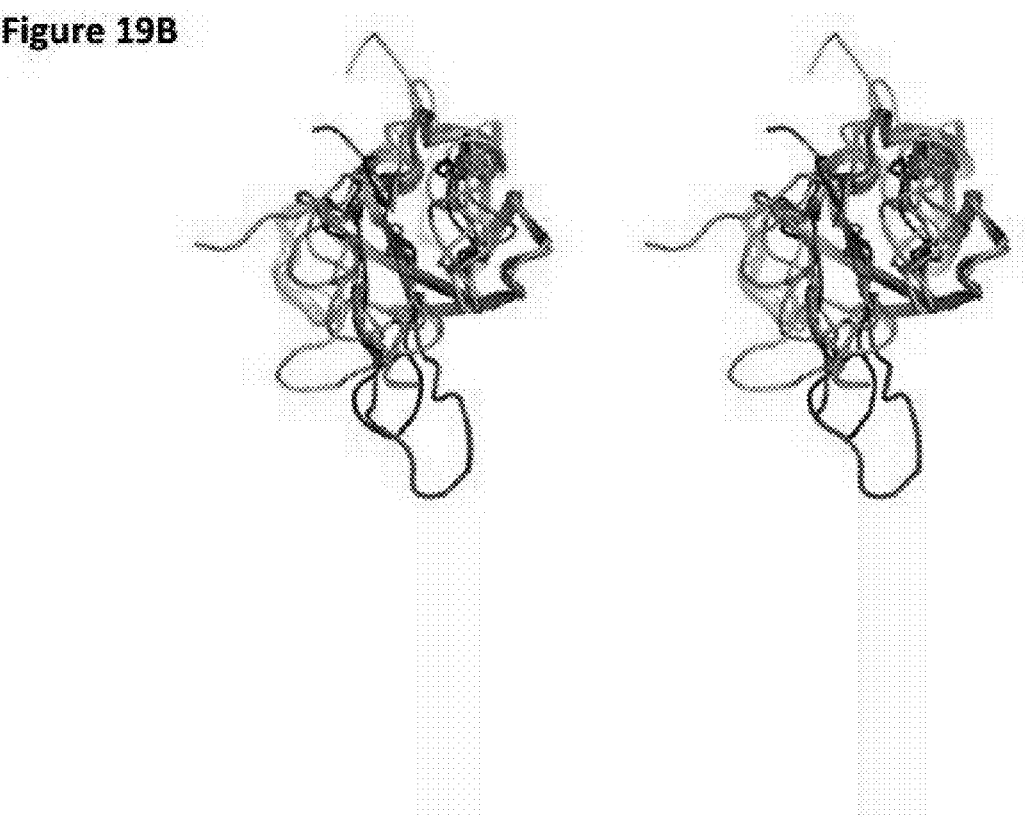

Structural comparisons showed that the wildtype molecule ($^{10}$Fn3; 1FNF residues 1416-1509) has a very similar topology to that of Adnectin 1 and Adnectin 2 when bound to their target molecules (FIGS. 14 and 19), including an excellent overlay of the core β-sheet and two of the three loops (AB and DE) distal from those which were diversified for selection (FIGS. 14A and 19A). The BC and DE loops of Adnectin 1 and Adnectin 2 were identical in length to the wildtype. In these structures the short DE loop showed minimal variation, while the BC loop showed more variation when compared to the $^{10}$Fn3 structure. Lys52 side chain in the DE loop of Adnectin 2 was close enough to the BC loop that it may be involved in stabilizing the displaced position of that loop compared to wildtype $^{10}$Fn3. The largest variations were in the FG loop, where, in the 1 FNF crystal structure, the native RGD motif was involved in a crystal contact and that contact was likely responsible for its orientation in that structure. The FG loop of Adnectin 1 was 5 residues longer than that of either $^{10}$Fn3 or Adnectin 2 and the F and G strands were extended. However, those residues involved in the extended β-strands were shown as tubes rather than arrows in FIG. 15 to emphasize the diversified residues. In Adnectin 2 the FG loop adopted yet a different conformation when bound to IL-23. Finally, the N-terminus was flexible in Adnectins. In $^{10}$Fn3, the position is dictated by the link to $^9$Fn3. In Adnectin 1 the N-terminus had a relatively similar conformation since it did not interact with EGFR. On the other hand, the N-terminus of Adnectin 2 was folded away compared to the other two N-termini maybe to avoid collision with IL-23. Thus, these structures show that Adnectin loops may adopt conformations distinct from wildtype depending upon the protein/protein interaction.

Crystallographic Data.

Space group, unit cell parameters and data collection statistics for both complexes are listed in Table 7. Initial electron density for the diversified loops, which were excluded from the molecular replacement model, is shown for the final model for both complexes in FIG. 16.

TABLE 3

Comparison of Buried Surface Area, Contacts, and Surface Complementarity for $^{10}$Fn3-based Domain Complexes

|  |  |  | Target Protein | | | $^{10}$Fn3-based Domain | | | Type of Contacts | | | |
|---|---|---|---|---|---|---|---|---|---|---|---|---|
| PDB ID | Protein | Pair | Area, Å² | # res | # atom | Area, Å² | # res | # atom | # H-bond | # Salt Links | # VDW | Sc |
| 2OCF | ERα |  | 900 | 22 | 47 | 870 | 17 | 51 | 6 | 2 | 77 | 0.66 |
| 3CSB | MBP |  | 650 | 16 | 59 | 600 | 14 | 51 | 7 | 0 | 121 | 0.70 |
| 3CSG | MBP |  | 750 | 15 | 56 | 680 | 15 | 53 | 11 | 1 | 125 | 0.64 |
| 3K2M | SH2 | AD | 570 | 16 | 47 | 580 | 10 | 48 | 11 | 2 | 105 | 0.72 |
|  |  | BC | 570 | 13 | 48 | 530 | 12 | 49 | 11 | 3 | 109 | 0.76 |
| 3QHT | ySUMO | AC | 600 | 13 | 48 | 560 | 12 | 43 | 8 | 0 | 87 | 0.71 |
|  |  | BD | 610 | 12 | 46 | 570 | 13 | 35 | 9 | 0 | 74 | 0.67 |
| 3QWQ | EGFR |  | 585 | 14 | 39 | 520 | 13 | 41 | 8 | 0 | 75 | 0.71 |
| 3QWR | IL-23 |  | 1370 | 38 | 97 | 1320 | 29 | 99 | 16 | 4 | 197 | 0.73 |

Proteins: ERα—estrogen receptor α; MBP—maltose binding protein; SH2—Src homology 2 from Abelson kinase; ySUMO—yeast small ubiquitin-related modifier
Pairs: In cases of multiple complexes per asymmetric unit all are tabulated. The letters indicates chain names in the pairs.
Area: calculated by the method of Connolly, 1983 and rounded to the nearest 10 Å².
res, # atom: Number of residues and number of atoms in contact as calculated by the method of Sheriff et al., 1987a; Sheriff, 1993.
H-bond, # Salt Links, # VDW: Number of atom pairwise hydrogen bonds and van der Waals interactions as calculated by the method of Sheriff et al., 1987a; Sheriff, 1993. Number of salt links is tabulated on a per residue basis.
Sc: Surface complementarity calculated by the method of Lawrence & Colman, 1993

TABLE 4

EGFR Alanine Scan

| Mutation | Secondary Structural Element | $K_D$, nM | Activity (parent/mutant) | pEGFR IC$_{50}$ (parent/mutant) | ΔInteraction Energy, kcal/mol |
|---|---|---|---|---|---|
| Parent |  | 1.8 | 1 | 1 | 0 |
| D23→A | BC loop | 2.4 | 0.7 | 0.3 | 0 |
| S24→A | BC loop | 1.3 | 1.4 | 0.7 | 0 |
| G25→A | BC loop | 2.0 | 0.9 | 0.3 | 0 |
| R26→A | BC loop | 2.0 | 0.9 | 0.8 | 0 |
| G27→A | BC loop | 1.1 | 1.6 | 1.4 | 0 |
| S28→A | BC loop | 1.5 | 1.2 | 0.5 | 0 |
| Y29→A | BC loop | 14 | 0.1 | 0.02 | 0 |
| Q30→A | BC loop | >50 | <0.04 | N.T. | 3 |
| Y31→A | C strand | N.D. |  | N.T. | 5 |
| F48→A | D strand | 3.9 | 0.5 | 0.1 | 1 |
| T49→A | D strand | 1.5 | 1.2 | 0.1 | −1 |
| V50→A | D strand | 3.4 | 0.5 | 0.1 | 1 |
| P51→A | D strand | 1.8 | 1 | N.T. | 3 |
| G52→A | DE loop | 14 | 0.1 | 0.04 | 0 |
| P53→A | DE loop | 2.8 | 0.6 | 0.3 | 1 |
| V54→A | DE loop | 17 | 0.1 | 0.03 | 2 |
| H55→A | DE loop | 3.0 | 0.6 | 0.6 | 0 |
| D77→A | FG loop | N.D. |  | N.D. | 6 |
| H78→A | FG loop | 5.5 | 0.3 | 0.1 | 2 |
| K79→A | FG loop | 17 | 0.1 | 0.0 | 1 |
| P79A→A | FG loop | 4.0 | 0.4 | 0.1 | 0 |
| H79B→A | FG loop | 3.9 | 0.5 | 0.1 | 0 |
| H79D→A | FG loop | 2.8 | 0.6 | 0.2 | 1 |
| G79E→A | FG loop | 4.4 | 0.4 | 0.1 | 0 |
| P80→A | FG loop | 4.2 | 0.4 | 0.1 | 0 |
| H81→A | FG loop | 10 | 0.2 | 0.0 | 1 |
| T82→A | FG loop | 6.1 | 0.3 | 0.1 | 0 |
| Y83→A | FG loop | N.D. |  | N.D. | 0 |
| H84→A | FG loop | 2.1 | 0.8 | 0.4 | 0 |
| E85→A | FG loop | 4.9 | 0.4 | 0.05 | 0 |

N.D. not detected; N.T. not tested.
pEGFR IC$_{50}$ is the inhibitory concentration at which phosphorylation of EGFR is inhibited 50%.
In the ΔInteraction Energy column bold numbers indicate what are expected to be significant losses of interaction energy.
See also Table 8.

TABLE 5

EGFR Mutants that Attempt to Improve Binding

| Mutation | Secondary Structural Element | $K_D$, nM | Activity (parent/mutant) | pEGFR IC$_{50}$ (parent/mutant) | ΔInteraction Energy, kcal/mol |
|---|---|---|---|---|---|
| Parent |  | 1.8 | 1 | 1 |  |
| Y31→F | BC loop | 2.0 | 0.9 | N.T. | 2 |
| Y31→S | BC loop | 0.70 | 2.5 | N.T. | <u>5</u> |
| Y31→L | BC loop | N.D. |  | N.D. | 2 |
| E47→R | D strand | 0.83 | 2.1 | N.T. | −4 |
| E47→K | D strand | 0.9 | 2.0 | N.T. | −6 |
| E47→D | D strand | 0.78 | 2.3 | N.T. | 0 |
| T49→I | D strand | 0.05 | 37 | 4.2 | 0 |
| T49→V | D strand | 0.14 | 12 | 3.1 | −1 |
| T49→Y | D strand | 0.21 | 8.4 | 1.0 | −3 |
| P51→T | D strand | N.D. |  | N.T. | −1 |
| P51→L | D strand | 1.5 | 1.2 | N.T. | −1 |
| T58→Q | E strand | 2.2 | 0.8 | 0.3 | 0 |
| T58→E | E strand | 1.3 | 1.3 | 0.7 | −9 |
| T58→D | E strand | 1.1 | 1.7 | 1.4 | −7 |
| A79C→L | FG loop | 4.0 | 0.4 | N.T. | −3 |
| A79C→N | FG loop | 2.3 | 0.8 | N.T. | −4 |
| A79C→Y | FG loop | 3.2 | 0.5 | N.T. | −8 |
| A79C→R | FG loop | 4.3 | 0.4 | N.T. | −11 |
| A79C→E | FG loop | 2.7 | 0.7 | N.T. | −8 |

N.D. not detected; N.T. not tested.
pEGFR IC50 is the inhibitory concentration at which phosphorylation of EGFR is inhibited 50%.

In the ΔInteraction Energy column bold numbers indicate what are expected to be significant losses of interaction energy, and underline indicates what are expected to significant gains of interaction energy.
See also Table 9.

TABLE 6

IL-23 IC$_{50}$

| Mutation | Secondary Structural Element | IC$_{50}$, nM | Activity (parent/mutant) | ΔInteraction Energy, kcal/mol |
|---|---|---|---|---|
| Parent |  | 1.0 | 1 |  |
| Y28→A | BC loop | 13 | 0.08 | <u>10</u> |
| Y73→A | F strand | 0.65 | 1.5 | <u>5</u> |
| Y81→A | FG loop | 35 | 0.03 | <u>7</u> |
| P87→A | FG loop | 8.3 | 0.1 | 2 |
| T35→N | C strand | 1.7 | 0.6 | 0 |
| T35→Q | C strand | 1.0 | 1 | −2 |

TABLE 6-continued

IL-23 IC$_{50}$

| Mutation | Secondary Structural Element | IC$_{50}$, nM | Activity (parent/mutant) | ΔInteraction Energy, kcal/mol |
|---|---|---|---|---|
| T35→E | C strand | 0.6 | 1.7 | -6 |
| T35→D | C strand | 49 | 0.02 | -7 |
| V45→N | D strand | 0.54 | 1.8 | 1 |
| V45→Q | D strand | 0.34 | 2.9 | 0 |
| V45→E | D strand | 0.51 | 1.9 | -6 |
| V45→D | D strand | 0.83 | 1.2 | -6 |
| Y73→N | F strand | 1.2 | 0.8 | 2 |
| Y73→Q | F strand | 0.26 | 3.8 | <u>3</u> |
| Y73→R | F strand | 1.2 | 0.8 | -2 |
| V75→Y | F strand | 2.2 | 0.4 | -1 |
|

TABLE 9

Energetic calculations for mutations to certain contact residues of EGFR/Adnectin 1 complex (Summarized in Table 5).

| Mutation | Mutant | | | | | Wild Type | | | | |
|---|---|---|---|---|---|---|---|---|---|---|
| | I.E. | VDW | ELE | % B | ΔG | I.E. | VDW | ELE | % B | ΔG |
| Y31→F | −3.7 | −3.8 | 0.1 | 65 | −0.8 | −6.1 | −6 | −0.1 | 78 | −1.3 |
| Y31→S | −1.5 | −1.6 | 0.1 | 93 | −0.9 | | | | | |
| Y31→L | −3.9 | −4 | 0.1 | 87 | −0.4 | | | | | |
| E47→R | −5.2 | −1.7 | −3.5 | 55 | −4.3 | −1 | −0.5 | −0.5 | 8 | −2.2 |
| E47→K | −6.7 | −1.3 | −5.4 | 27 | −7 | | | | | |
| E47→D | −0.8 | −0.4 | −0.4 | 17 | −1.6 | | | | | |
| T49→I | −5.3 | −3.3 | −2 | 67 | −2.5 | −5.2 | −2.2 | −2.9 | 70 | −3.2 |
| T49→V | −4.3 | −2.3 | −2 | 60 | −2.2 | | | | | |
| T49→Y | −5.3 | −3.3 | −2 | 67 | −2.5 | | | | | |
| P51→T | −5.3 | −3.3 | −2 | 67 | −2.5 | −6.1 | −5.8 | −0.3 | 92 | 0.5 |
| P51→A | −4.3 | −2.3 | −2 | 60 | −2.2 | | | | | |
| P51→L | −6.6 | −6.2 | −0.4 | 86 | −0.6 | | | | | |
| T58→Q | −0.2 | −0.1 | −0.1 | 1 | −1.9 | −0.6 | −0.2 | −0.4 | 2 | −1.6 |
| T58→E | −9.7 | −1.1 | −8.6 | 38 | −9.8 | | | | | |
| T58→D | −7.9 | −0.8 | −7.1 | 32 | −7.7 | | | | | |
| A79C→L | −3.7 | −3.6 | −0.1 | 66 | −0.1 | −1.1 | −1.1 | 0 | 63 | 1 |
| A79C→N | −5 | −3.2 | −1.8 | 50 | −1.5 | | | | | |
| A79C→Y | −9.7 | −8.8 | −0.9 | 77 | −1.3 | | | | | |
| A79C→R | −12.3 | −7.6 | −4.7 | 81 | −2.5 | | | | | |
| A79C→E | −9.2 | −6.7 | −2.5 | 77 | −1.4 | | | | | |

*Columns: I.E. = Interaction energy; VDW = Van der Waals interactions; ELE = electrostatic interactions; % B = % buried surface

TABLE 10

Energetic calculations for contact residues of Adnectin 2/IL-23 complex (Summarized in Table 6).

| Mutation | Mutant | | | | | Wild Type | | | | |
|---|---|---|---|---|---|---|---|---|---|---|
| | I.E. | VDW | ELE | % B | ΔG | I.E. | VDW | ELE | % B | ΔG |
| Y28→A | | | | | | | | | | |
| Y73→A | | | | | | | | | | |
| Y81→A | | | | | | | | | | |
| P87→A | | | | | | | | | | |
| T35→N | 0 | 0 | 0 | 11 | −1 | −0.8 | −0.6 | −0.2 | 25 | −0.5 |
| T35→Q | −3.2 | −1.8 | −1.4 | 77 | −2.7 | | | | | |
| T35→E | −6.4 | −1 | −5.4 | 61 | −6.7 | | | | | |
| T35→D | −7.5 | −0.5 | −7 | 78 | −8 | | | | | |
| V45→N | −0.2 | −0.3 | 0.1 | 5 | −1.1 | −0.8 | −0.6 | −0.2 | 25 | −0.5 |
| V45→Q | −0.4 | −0.3 | −0.1 | 7 | −1.9 | | | | | |
| V45→E | −7 | −0.9 | −6.1 | 42 | −7.3 | | | | | |
| V45→D | −6.9 | −0.5 | −6.4 | 42 | −6.9 | | | | | |
| Y73→N | −3.9 | −1.3 | −2.6 | 76 | −3.4 | −5.6 | −2.5 | −3.1 | 84 | −3.8 |
| Y73→Q | −2.8 | −0.6 | −2.2 | 60 | −3.4 | | | | | |
| Y73→R | −7.6 | −4.7 | −2.9 | 75 | −4.1 | | | | | |
| V75→Y | −1.3 | −1.1 | −0.2 | 20 | −1.8 | −0.7 | −0.7 | 0 | 28 | −0.6 |
| V75→Q | −1.1 | −0.7 | −0.4 | 24 | −2.1 | | | | | |
| V75→K | −1.4 | −1.5 | 0.1 | 32 | −1.7 | | | | | |

*Columns: I.E. = Interaction energy; VDW = van der Waals interactions; ELE = electrostatic interactions; % B = % buried surface Example 3

Solubility of Adnectin mutants

Experimental Procedures

EGFR #8 (SEQ ID NO:67), EGFR #8-T58E (SEQ ID NO:69), EGFR #8-T58D (SEQ ID NO:70), EGFR #4 (SEQ ID NO:68) and EGFR #4-T58E (SEQ ID NO:71) Adnectins were expressed and purified as described above in Examples 1 and 2. All proteins were dialyzed into 10 mM NaPO4, 130 mM NaCl (PBS) pH 7.1, and samples were confirmed to be >97% monomeric using analytical size exclusion chromatography on a Zenix-C SEC-300 column in buffer containing 200 mM K2HPO4, 150 mM NaCl, pH 6.8, plus 0.02% Na azide, running at 0.35 mL/min.

Analysis of the thermal stability of EGFR #8, EGFR #8-T58E, EGFR #8-T58D, EGFR #4 and EGFR #4-T58E was conducted by differential scanning calorimetry (DSC) using a MicroCal Capillary DSC instrument. To stabilize the DSC instrument baseline and obtain a consistent thermal history, multiple scans of PBS pH 7.1 buffer alone in both the sample and reference cell were recorded prior to sample analysis. Sample scans contained 1.0 mg/ml Adnectin in the sample cell and matched PBS pH 7.1 buffer in the reference cell. All scans were run from 10-100° C. at a scan rate of 60°/hr using a 15 minute pre-cycle thermostat period and no post-cycle thermostat period. Data were analyzed using MicroCal Origin analysis software.

Ammonium sulfate solubility experiments for the EGFR #4 Adnectins were performed using the automated assay method described in Example 1. Ammonium sulfate solubility experiments for the EGFR #8 proteins were performed using the benchscale method described in Example 1which enabled titration to higher ammonium sulfate concentrations than the automated method.

Small scale ultrafiltration experiments for EGFR #8, EGFR #8-T58E and EGFR #8-T58D were performed by slowly concentrating the Adnectins at 2-8° C. in VivaSpin 3000 MWCO concentrators with periodic mixing to avoid gradient formation. Volumes were visually monitored during the concentration process to enable estimation of the expected sample concentration based on volume reduction, and aliquots were removed at various points for analysis. These aliquots were incubated overnight at 2-8° C., and any insoluble material was removed by centrifugation prior to determination of soluble protein concentration by $A_{280}$, and oligomeric state by SEC using a Zenix-C SEC-300 column in buffer containing 200 mM K2HPO4, 150 mM NaCl, pH 6.8, plus 0.02% Na azide, running at 0.35 mL/min.

Initial small scale ultrafiltration experiments using EGFR #4 and EGFR #4-T58E performed at 2-8° C. were hindered by very slow rates of volume reduction. Therefore, EGFR #4 and EGFR #4-T58E were instead concentrated near room temperature (21° C.), where a faster rate of volume reduction was observed. Volumes were visually monitored during the concentration process to enable estimation of the expected sample concentration based on volume reduction, and aliquots were removed at various points for analysis. To follow up on the temperature dependent ultrafiltration rate observations, each aliquot was divided into two sister aliquots, with one set incubated overnight at 2-8° C. and the other set incubated overnight at room temperature. The following morning, insoluble material was removed by centrifugation and then the soluble protein concentration was determined by $A_{280}$, and the oligomeric state characterized by SEC using a Zenix-C SEC-300 column in buffer containing 200 mM K2HPO4, 150 mM NaCl, pH 6.8, plus 0.02% Na azide, running at 0.35 mL/min.

Accelerated stability studies for EGFR #8, EGFR #8-T58E and EGFR #8-T58D were conducted by incubating 46 mg/ml samples of each Adnectin at 40° C. for two weeks. Aliquots were removed at time zero (immediately before initiation of the 40° C. incubation), and at time 1 week and 2 weeks. Aliquots were centrifuged to remove and insoluble material and then the soluble protein concentration was determined by $A_{280}$, and the oligomeric state characterized by SEC using a Zenix-C SEC-300 column in buffer containing 200 mM K2HPO4, 150 mM NaCl, pH 6.8, plus 0.02% Na azide, running at 0.35 mL/min.

Figure 20A:
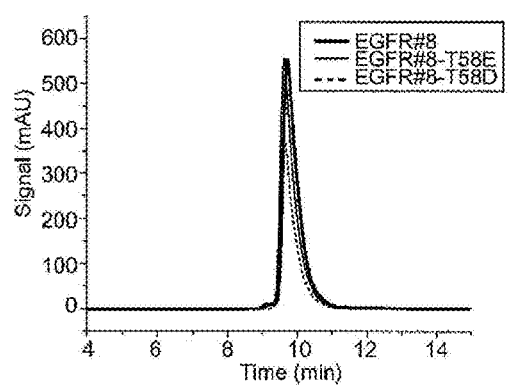
FIGS. 20A-20E. Oligomeric state and thermal stability of EGFR #8 Adnectins.
Figure 20B:
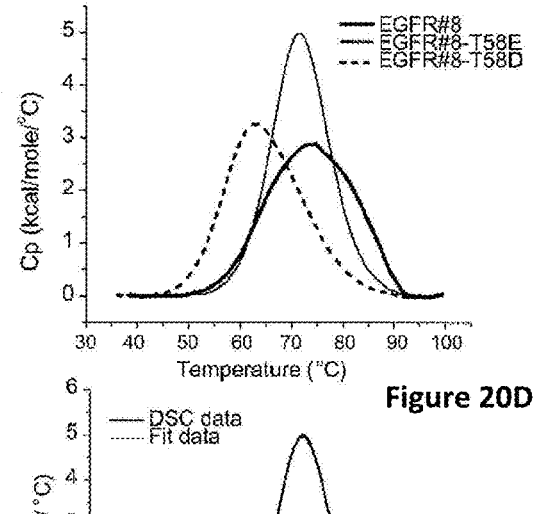
Figure 20C:
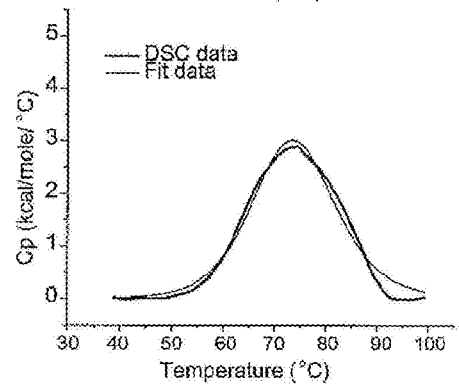
Figure 20D:
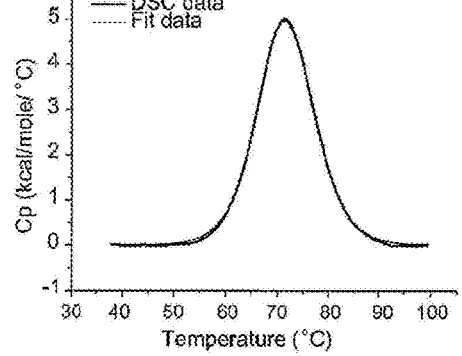
Figure 20E:
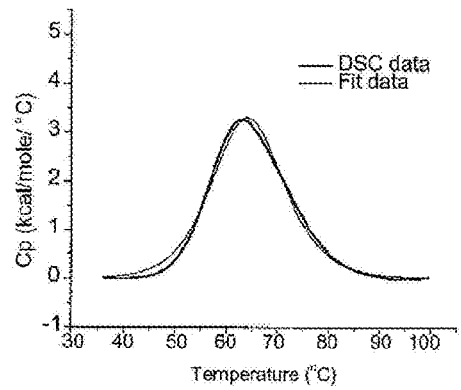

Results:

The initial ammonium sulfate solubility experiments with EGFR #8 (FIGS. 10 and 11) suggested that the T58E and T58D mutations improve the solubility of the EGFR #8 Adnectin. To further characterize the effect of these mutations, wild type EGFR #8 as well as EGFR #8-T58E and EGFR #8-T58D mutants were expressed and purified at larger scale to generate enough material for more detailed biophysical studies. The purified proteins were of suitable purity for biophysical studies, with more than 98% monomer for each sample as measured by SEC (FIG. 20A). The overall thermal stability for wild type EGFR #8 and EGFR #8-T58E were also similar, with the melting curve for EGFR #8 consisting of a broad thermal transition with $T_{onset}$ near 50° C. and $T_m$ of 74.0° C., and EGFR #8-T58E having a more symmetrical Gaussian-shaped melting profile with $T_{onset}$ near 50° C. and $T_m$ of 71.7° C. (FIG. 20B-D). However, the thermal stability of EGFR #8-T58D was considerably lower, with $T_{onset}$ near 43° C. and $T_m$ of 64.4° C. (FIGS. 20B and 20E), suggesting that the T58D mutation may cause a conformational change in the Adnectin that reduces the protein's stability.

The impact of the T58E and T58D mutations on the aggregation of EGFR #8 was next investigated using the ammonium sulfate solubility assay. Ammonium sulfate salting out curves generated using the larger scale preparations of purified Adnectin material confirmed that the solubility in ammonium sulfate was increased for each mutant compared to the wild type protein of EGFR #8 (FIG. 21).

As an orthogonal measure of aggregation propensity to the AS method, we performed small scale ultrafiltration experiments using EGFR #8, EGFR #8-T58E and EGFR #8-T58D as described above. Each of the three Adnectins were found to have high solubility (>100 mg/ml) (FIG. 22A). The good agreement between observed [protein] and expected [protein] for both EGFR #8 and EGFR #8-T58E suggests that the solubility limit for each of these molecules is greater than the concentrations achieved in this experiment. The observed concentrations for EGFR #8-T58D also tracked well with the expected concentrations except for the final (most concentrated) aliquot for which the measured concentration (112 mg/ml) was lower than the expected concentration (~150±25 mg/ml). The lower recovery for EGFR #8-T58D at elevated concentration suggests that this protein may have higher aggregation propensity than EGFR #8 and EGFR #8-T58E under these conditions, while the aggregation propensity of EGFR #8-T58E is indistinguishable from the wild type EGFR #8 Adnectin. SEC data showed similar small increases in soluble HMW for each protein as a function of protein concentration, with each protein remaining >97% monomeric (<3% HMW) even at concentrations greater than 100 mg/ml (FIG. 22B).

Because solubility differences between wild type EGFR #8 and EGFR #8-T58E were difficult to resolve in the ultrafiltration studies due to the high solubility of each molecule, we attempted to differentiate the aggregation propensity of the Adnectins using accelerated stability studies. Here, "time zero" (t0) samples of 46 mg/ml EGFR #8, EGFR #8-T58E and EGFR #8-T58D were prepared in PBS pH 7.1, and confirmed to be >98% monomer by SEC (FIG. 23C). The samples were then incubated at 40° C. for 2 weeks, and at time 1 week (1w) and 2 weeks (2w) insoluble material was removed by centrifugation and the soluble fraction was analyzed by $A_{280}$ and SEC to determine protein concentration and oligomeric state. These data showed that the concentration of wild type EGFR #8 decreased by ~60% to ~19 mg/ml after 1 week at 40° C., and then decreased to 16 mg/ml by the 2w time point (FIG. 23A). The concentration of the EGFR #8-T58D decreased even more than the wild type EGFR #8 Adnectin, to 11 mg/ml by 1 w and 9 mg/ml by 2w. On the other hand, the concentration of EGFR #8-T58E decreased to only 40 mg/ml by 1w and to 36 mg/ml by 2w (FIG. 23A). These changes in soluble protein concentration were confirmed by the integrated SEC peak area data (FIG. 23B). The SEC data also showed that the soluble fraction of each sample remained >98% monomeric, with a small reduction in % HMW over time likely indicating a higher aggregation propensity for the HMW species compared to monomeric adnectin (FIG. 23C). Collectively, these data indicate that EGFR #8-T58E is significantly more resistant to aggregation than EGFR #8 or EGFR #8-T58D under these accelerated stress conditions.

The data comparing the aggregation properties of EGFR #8 to EGFR #8-T58E (FIGS. 21-23) suggested that the T58E mutation decreases the aggregation propensity of this particular Adnectin. To determine if this T58E mutation has a similar favorable impact on the aggregation properties of other Adnectins, we expressed and purified multi-milligram quantities of wild type EGFR #4 and EGFR #4-T58E Adnectins for biophysical studies. The EGFR #4 Adnectin was selected for the study because we had earlier found this Adnectin was highly aggregation prone in both AS salting out studies (FIG. 3A) and in ultrafiltration experiments (Table 1), and therefore we anticipated that any effect of the T58E mutation would be more easily detectable for EGFR #4 than for less aggregation-prone Adnectins. Despite binding to the same EGFR target protein, the EGFR #4 adnectin had different target binding loop sequences than EGFR #8 (FIG. 24).

Figure 25B:
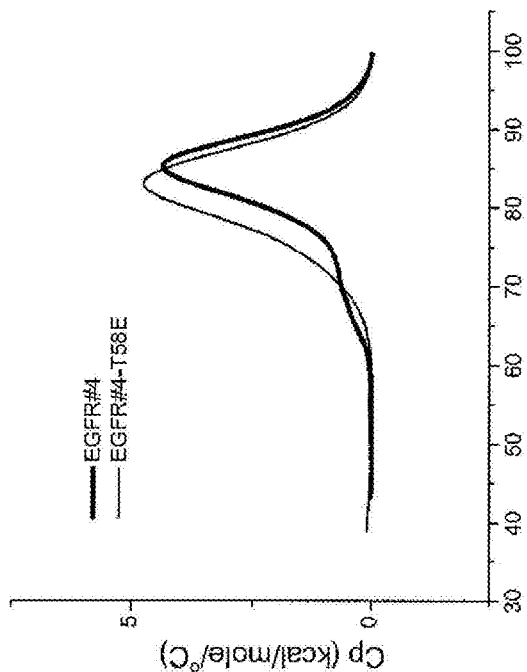
FIGS. 25A-25D. Oligomeric state and thermal stability of EGFR #4 Adnectins.
Figure 25D:
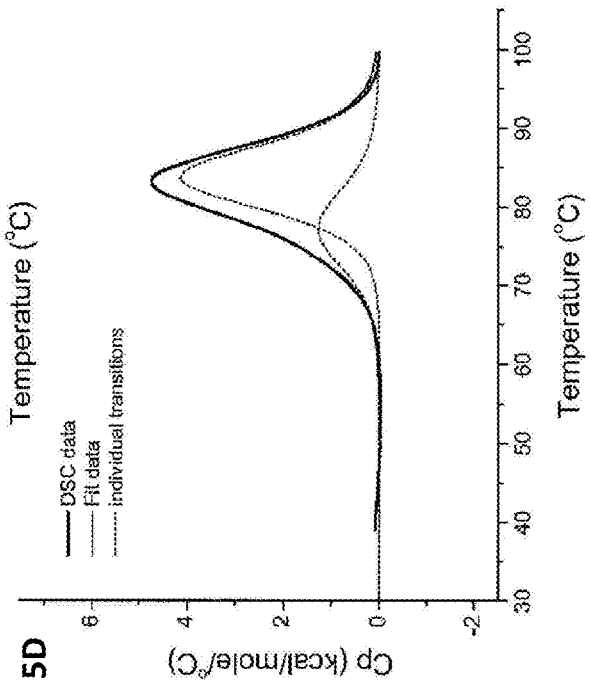
Figure 25A:
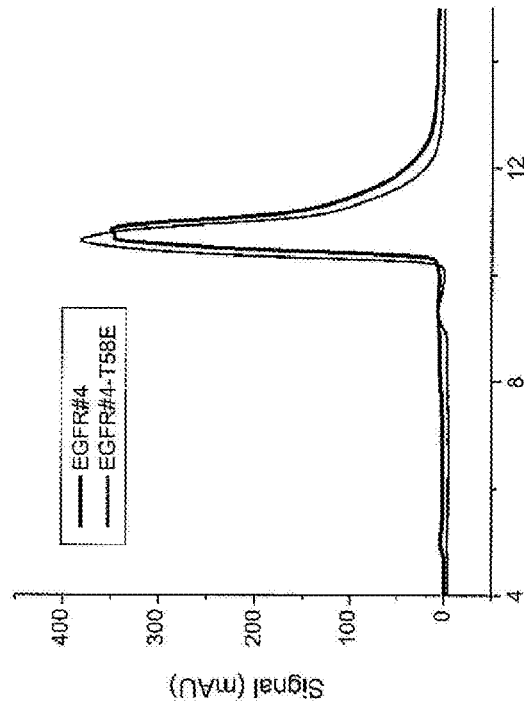
Figure 25C:
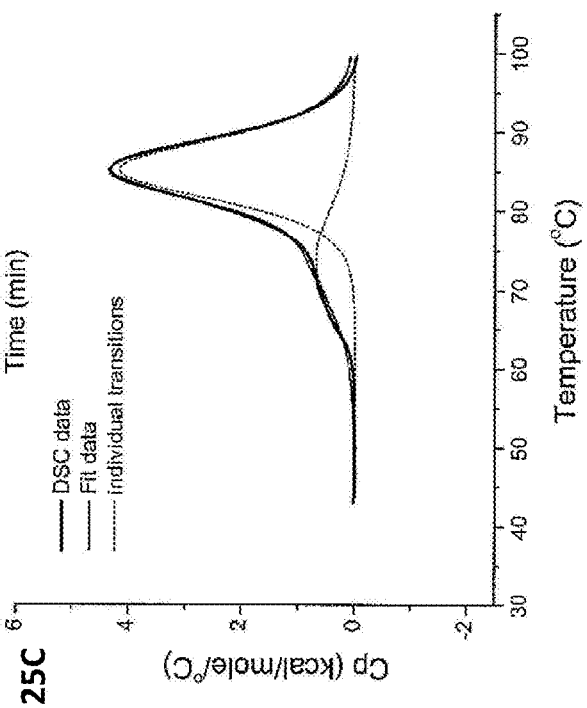

Purified EGFR #4 and EGFR #4-T58E proteins were shown by SEC to be of suitable purity for biophysical studies, with more than 97% monomer for each sample (FIG. 25A). The DSC thermogram for wild type EGFR #4 showed that the Adnectin had high thermal stability, with a $T_{onset}$ of ~60° C. with two clearly resolvable transitions; a minor transition with Tm=74.3° C. and a dominant transition with Tm=85.3° C. (FIG. 25B-C) The DSC data for EGFR #4-T58E showed a similar $T_{onset}$ near ~60° C., and the thermogram data for EGFR #4 was also best described by two overlapping transitions with a minor transition having Tm1=77.4° C. and dominant transition with Tm2=83.8° C. (FIGS. 25B and D). Therefore, like EGFR #8 (FIG. 20), the DSC data suggest that the thermal stability of EGFR #4 was not significantly reduced by the T58 E mutation.

Ammonium sulfate salting out curves for the large scale preparations of wild type EGFR #4 and EGFR #4-T58E show that the T58E mutation increases the solubility of the protein in AS, with ASm=0.865±0.014 M for wild type EGFR #4, and ASm=1.024±0.003 for EGFR #4-T58E (average and standard deviation of quadruplicate measurements), when tested at 0.3 mg/ml [protein] (FIG. 26).

Small scale ultrafiltration studies were performed with EGFR #4 and EGFR #4-T58E to examine their aggregation propensity. Initial ultrafiltration studies performed at 2-8° C. were unsuccessful for both the wild type and mutant Adnectin due to very slow rates of volume reduction, suggesting possibly high aggregation propensity of each protein at these low temperatures. However, both Adnectins concentrated at considerably faster rates when the ultrafiltration study was conducted near room temperature (21° C.). Therefore, to investigate this temperature-dependent phenomenon, samples were concentrated by ultrafiltration at room temperature and aliquots were stored at either 2-8° C. or at room temperature overnight. The next morning the insoluble material was removed by centrifugation (and 2-8° C. or room temperature respectively) and the soluble protein concentration was measured by $A_{280}$, and the oligomeric state was characterized by SEC. The data for wild type EGFR #4 showed that the majority of the protein precipitated during 2-8° C. storage, such that the highest concentration of soluble EGFR #4 after overnight storage was 5.2 mg/ml (FIG. 27A), in good agreement with our earlier study for EGFR #4 performed under similar conditions (see Table 1). EGFR #4-T58E showed a similar trend in concentration to wild type except at the highest concentration data point where slightly more EGFR #4-T58E remained in solution (7.4 mg/ml) compared to wild type. The recoveries for both proteins were significantly improved in the aliquots incubated at room temperature, and EGFR #4-T58E in particular was found to have nearly two-fold higher concentration (22 mg/ml) than wild type EGFR #4 (12 mg/ml) in the highest concentration aliquots (FIG. 27A). SEC data showed similar trends for increasing HMW as a function of protein concentration for EGFR #4 and EGFR #4-T58E (FIG. 27B). These data showed that the T58-E mutation reduced the aggregation propensity of EGFR #4.

The entire disclosure of each document cited herein (including patents, patent applications, journal articles, abstracts, laboratory manuals, books, GENBANK® Accession numbers, SWISS-PROT® Accession numbers, RCSB Protein Data Bank Accession numbers, or other disclosures) is hereby incorporated herein by reference in their entirety.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

---

The invention claimed is:

1. A polypeptide comprising a 10$^{th}$ human fibronectin type III ($^{10}$Fn3) domain comprising AB, BC, CD, DE, EF and FG loops, wherein the $^{10}$Fn3 domain comprises:
   (a) AB, CD and EF loops comprising amino acid sequences corresponding to the amino acid sequence of the AB, CD and EF loops of SEQ ID NO: 1, respectively;
   (b) one or more amino acid substitutions in
      (i) the BC loop corresponding to amino acids 23-31 of SEQ ID NO: 1,
      (ii) the DE loop corresponding to amino acids 51-56 of SEQ ID NO: 1,
      (iii) the FG loop corresponding to amino acids 75-87 of SEQ ID NO: 1, or
      (iv) a combination of two or more of the BC, DE and FG loops; and
   (c) Glu (E) at the position corresponding to residue 58 of SEQ ID NO: 1,
wherein the solubility of the $^{10}$Fn3 domain is enhanced relative to the solubility of the same $^{10}$Fn3 domain wherein the amino acid corresponding to residue 58 of SEQ ID NO: 1 is Thr (T), and wherein solubility of the polypeptide is determined using an ammonium sulfate solubility assay.

2. The polypeptide of claim 1, wherein $^{10}$Fn3 domain comprises a BC loop which has the amino acid sequence of the corresponding BC loop of the wildtype human $^{10}$Fn3 domain (SEQ ID NO:1).

3. The polypeptide of claim 1, wherein the DE loop of the $^{10}$Fn3 domain is hydrophobic.

* * * * *